United States Patent
Brown

(10) Patent No.: US 11,339,427 B2
(45) Date of Patent: May 24, 2022

(54) METHOD FOR TARGET SPECIFIC RNA TRANSCRIPTION OF DNA SEQUENCES

(71) Applicant: JumpCode Genomics, Inc., Carlsbad, CA (US)

(72) Inventor: Keith Brown, Carlsbad, CA (US)

(73) Assignee: JUMPCODE GENOMICS, INC., Carlsbad, CA (US)

( * ) Notice: Subject to any disclaimer, the term of this patent is extended or adjusted under 35 U.S.C. 154(b) by 536 days.

(21) Appl. No.: 16/101,083

(22) Filed: Aug. 10, 2018

(65) Prior Publication Data

US 2019/0153528 A1 May 23, 2019

Related U.S. Application Data

(63) Continuation-in-part of application No. PCT/US2017/017530, filed on Feb. 10, 2017.

(60) Provisional application No. 62/545,876, filed on Aug. 15, 2017, provisional application No. 62/294,875, filed on Feb. 12, 2016.

(51) Int. Cl.
  *C12Q 1/6869* (2018.01)
  *C12Q 1/6865* (2018.01)

(52) U.S. Cl.
  CPC ......... *C12Q 1/6869* (2013.01); *C12Q 1/6865* (2013.01); *C12N 2310/20* (2017.05)

(58) Field of Classification Search
  None
  See application file for complete search history.

(56) References Cited

U.S. PATENT DOCUMENTS

| | | |
|---|---|---|
| 2001/0031466 A1 | 10/2001 | Malek |
| 2005/0255089 A1 | 11/2005 | Chiorini et al. |
| 2006/0040297 A1 | 2/2006 | Leamon et al. |
| 2006/0252060 A1 | 11/2006 | Willis et al. |
| 2009/0036325 A1 | 2/2009 | McKernan et al. |
| 2009/0098548 A1 | 4/2009 | Ason et al. |
| 2009/0264299 A1 | 10/2009 | Drmanac et al. |
| 2010/0287628 A1 | 11/2010 | Ostertag et al. |
| 2011/0111409 A1 | 5/2011 | Sinicropi et al. |
| 2012/0252015 A1 | 10/2012 | Hindson et al. |
| 2012/0258892 A1 | 10/2012 | Wang |
| 2013/0203605 A1 | 8/2013 | Shendure et al. |
| 2013/0315886 A1 | 11/2013 | Gage et al. |
| 2014/0356867 A1 | 12/2014 | Peter et al. |
| 2014/0357523 A1 | 12/2014 | Zeiner et al. |
| 2015/0159174 A1 | 6/2015 | Frendewey et al. |
| 2015/0165054 A1 | 6/2015 | Liu et al. |
| 2015/0225773 A1 | 8/2015 | Farmer et al. |
| 2016/0053304 A1 | 2/2016 | Wurtzel et al. |
| 2016/0090622 A1 | 3/2016 | Liu et al. |
| 2016/0034169 A1 | 12/2016 | Brown et al. |
| 2016/0376663 A1 | 12/2016 | Brown |
| 2017/0101674 A1 | 4/2017 | So et al. |
| 2017/0247689 A1 | 8/2017 | Brown |
| 2018/0010180 A1 | 1/2018 | Zhou et al. |
| 2018/0016630 A1 | 1/2018 | Godwin et al. |
| 2018/0237950 A1 | 8/2018 | Brown |
| 2018/0273933 A1 | 9/2018 | Gunderson et al. |
| 2019/0360044 A1 | 11/2019 | Chen et al. |
| 2020/0181700 A1 | 6/2020 | Brown et al. |

FOREIGN PATENT DOCUMENTS

| | | |
|---|---|---|
| CN | 102439177 A | 5/2012 |
| JP | 2003508082 A | 3/2003 |
| WO | WO-9916908 A2 | 4/1999 |
| WO | WO-0000632 A1 | 1/2000 |
| WO | WO-2004081225 A2 | 9/2004 |
| WO | WO-2008134596 A2 | 11/2008 |
| WO | WO-2012048113 A2 | 4/2012 |
| WO | WO-2012061832 A1 | 5/2012 |
| WO | WO-2013176772 A1 | 11/2013 |
| WO | WO-2013191775 A2 | 12/2013 |
| WO | WO-2015002780 A1 | 1/2015 |
| WO | WO-2015131101 A1 | 9/2015 |
| WO | WO-2016022931 A1 | 2/2016 |
| WO | WO-2016100955 A2 | 6/2016 |
| WO | WO-2017015075 A1 | 1/2017 |
| WO | WO-2017218512 A1 | 12/2017 |
| WO | WO-2018114706 A1 | 6/2018 |

OTHER PUBLICATIONS

Adiconis, Xian et al. Comparative analysis of RNA sequencing methods for degraded or low-input samples, Nature Methods, 10(7):623-629 (May 19, 2013).
Brouns, SJ Molecular biology. A Swiss army knife of immunity. Science 337(6069):808-9 (Aug. 17, 2012).
Carpenter, et al. Pulling out the 1%: Whole-Genome Capture for the Targeted Enrichment of Ancient DNA Sequencing Libraries. The American Journal of Human Genetics 93: 852-864, 2013.
Deltcheva et al. CRISPR RNA maturation by trans-encoded small RNA and host factor RNase III. Nature 471:602-607 (2011).
Dolinsek, et al. Depletion of unwanted nucleic acid templates by selective cleavage: LNAzymes, catalytically active oligonucleotides containing locked nucleic acids, open a new window for detecting rare microbial community members. App. Environ Microbiol 79(5):1534-1544 (Mar. 2013).
European Application No. 15746731.7 Search Report dated Sep. 5, 2017.
European Application No. 15754498.2 European Search Report dated Nov. 27, 2017.

(Continued)

*Primary Examiner* — Nancy J Leith
(74) *Attorney, Agent, or Firm* — Wilson Sonsini Goodrich & Rosati

(57) ABSTRACT

Disclosed herein are methods of long range target specific amplification and sequencing using an RNA intermediate synthesized directly from the target including using hairpin adaptors having a double stranded promoter and an overhang which hybridizes with a reverse-complementary overhang on a target nucleic acid. RNA transcription eliminates clonal amplification of early synthesis errors. Approaches allow for the identification of target-adjacent sequence, such as sequence adjacent to a repeat element target. Also disclosed herein are compositions and kits for amplification and sequencing.

23 Claims, 10 Drawing Sheets

Specification includes a Sequence Listing.

(56) References Cited

OTHER PUBLICATIONS

Gao, X et al. In vivo cancer targeting and imaging with semiconductor quantum dots, Nature Biotechnology, 22(8):969-976 (Jul. 18, 2004).

Green, S.J. et al. Suicide Polymerase Endonuclease Restriction, a novel technique for enhancing PCR amplification of minor DNA templates, Applied and Environmental Microbiology, 71(8):4721-4727 (Aug. 1, 2005).

International Application No. PCT/US2015/014242 International Preliminary Report on Patentability dated Aug. 9, 2016.

International Application No. PCT/US2015/018115 International Preliminary Report on Patentability dated Aug. 30, 2016.

International Application No. PCT/US2015/018115 International Search Report and Written Opinion dated May 29, 2015.

International Application No. PCT/US2015/8014242 International Search Report and Written Opinion dated Jul. 30, 2015.

International Application No. PCT/US2016/019609 International Preliminary Report on Patentability dated Aug. 29, 2017.

International Application No. PCT/US2017/017530 International Preliminary Report on Patentability dated Aug. 23, 2018.

International Application No. PCT/US2017/017530 International Search Report and Written Opinion dated May 15, 2017.

Iskow, Rebecca C. et al. Natural Mutagenesis of Human Genomes by Endogenous Retrotransposons, Cell 141(1):1253-1261 (Jun. 1, 2010).

Jiang, W. et al. Demonstration of CRISPR/Cas9/sgRNA-mediated targeted gene modification in *Arabidopsis*, tobacco, sorghum and rice. Nucleic Acids Res. (Nov. 2013), 41(20):e188.

Jinek et al. A programmable dual-RNA-guided DNA endonuclease in adaptive bacterial immunity. Science 337:816-821 (2012).

Jinek, M. et al. A programmable dual-RNA-guided DNA endonuclease in adaptive bacterial immunity. Science 337, Supp. pp. 1-37 (2012).

Kantarjian, H.M. et al. Dose escalation of imatinib mesylate can overcome resistance to standard-dose therapy in patients with chronic myelogenous leukemia. Blood, 101(2):473-475 (Jan. 15, 2003).

Kolpashchikov, D. An Elegant Biosensor Molecular Beacon probe: Challenges and Recent Solutions, Scientifica 2012;1-17 (Dec. 3, 2012) Article ID 928783.

Laurent, ST G. III et al. A LINE-1 component to human aging: do LINE elements exact a longevity cost for evolutionary advantage? Mechanisms of Ageing and Development, 131(5):299-305 (May 1, 2010).

Lee, E. et al. Landscape of Somatic Retrotransposition in Human Cancers, Science 337(6097):967-971 (Jun. 28, 2012) Supplement.

Lerat, E. et al. Influence of the transposable element neighborhood on human gene expression in normal and tumor tissues. Gene 396:303-311 (2007).

Li, W. et al. Activation of transposable elements during aging and neuronal decline in *Drosophila*, Nature Neuroscience 16(5):529-531 (Apr. 7, 2013).

Shukla, Ruchi et al. Endogenous Retrotransposition Activates Oncogenic Pathways in Hepatocellular Carcinoma, Cell 153(1):101-111 (Mar. 1, 2013).

Soriano, V. et al. Hepatitis C virus-RNA clearance in HIV-coinfected patients with chronic hepatitis C treated with pegylated interferon plus ribavirin. Antiviral Therapy, 9:505-509 (2004).

Terns et al. CRISPR-based adaptive immune systems. Curr. Opin. Microbiol. 14:321-327 (2011).

U.S. Appl. No. 15/116,404 Non-Final Office Action dated May 23, 2018.

U.S. Appl. No. 15/121,725 Final Office Action dated Sep. 6, 2018.

U.S. Appl. No. 15/121,725 Non-Final Office Action dated Feb. 9, 2018.

Vlad, SC et al. Protective effects of NSAIDs on the development of Alzheimer disease.Neurology, 70(19):1672-1677 (May 6, 2008).

Zhang, F. et al. CRISPR/Cas9 for genome editing: Progress, Implications and challenges. Human Molecular Genetics 23(R1):R40-R46 (Mar. 20, 2014).

Bhargava et al., Technical variations in low-input RNA-seq methodologies. Scientific Reports 4:3678, 1-10 (2014).

Brouilette et al., A simple and novel method for RNA-seq library preparation of single cell cDNA analysis by hyperactive Tn5 transposase. Developmental Dynamics 241(10):1584-1590 (2012).

Gasiunas et al., Cas9-crRNA ribonucleoprotein complex mediates specific DNA cleavage for adaptive immunity in bacteria. PNAS109(39):E2579-E2586 (2012).

Gomaa et al., Programmable Removal of Bacterial Strains by Use of Genome-Targeting CRISPR-Cas Systems. mBio 5(1):e00928-e00913 (2014).

PCT/US2020/017707 International Search Report and Written Opinion dated May 21, 2020.

U.S. Appl. No. 15/121,725 Office Action dated Aug. 1, 2019.

U.S. Appl. No. 15/121,725 Final Office Action dated Apr. 13, 2020.

U.S. Appl. No. 15/553,495 Final Office Action dated May 5, 2020.

U.S. Appl. No. 15/553,495 Office Action dated Sep. 18, 2019.

PCT/US2020/052652 International Search Report and Written Opinion dated Dec. 29, 2020.

U.S. Appl. No. 15/121,725 Non-Final Office Action dated Nov. 10, 2020.

Feehery et al. A Method for Selectively Enriching Microbial DNA from Contaminating Vertebrate Host DNA. PLOS ONE 8(10):e76096. 13 pages. (Oct. 28, 2013).

Malina, et al. Repurposing CRISPR/Cas9 for in situ functional assays. Genes & development 27.23 (2013): 2602-2614.

PCT/US2021/013598 International Search Report and Written Opinion dated Apr. 2, 2021.

PCT/US2021/013701 International Search Report and Written Opinion dated Apr. 21, 2021.

Shagina, et al. Normalization of genomic DNA using duplex-specific nuclease. Biotechniques. Jun. 2010;48(6):455-9. doi: 10.2144/000113422.

U.S. Appl. No. 15/121,725 Final Office Action dated Jun. 3, 2021.

U.S. Appl. No. 16/793,908 Non-Final Office Action dated Jun. 24, 2021.

Xing et al., Mobile element biology: new possibilities with high-throughput sequencing. Trends Genet 29(5):280-289 (2013).

Zhulidov, et al. Simple cDNA normalization using kamchatka crab duplex=specific nuclease. Nucleic Acids Research Online Feb. 18, 2004. 32:3 e37.

GCTTCCGGGCCCACGGCCAAGCAACGAGGCAGACCTCTGGCGATCCCAACGTGCCACGCT
CGGCGGTCATGGCCGTCTCAATGGCCGTCCGACCGACTAGCGCTTGCT**CGACCCTTGTTA
CGAACCA**CGGTTCCTGCAACGCACACGG (SEQ ID NO: 2)

Figure 3

(CGACCCTTGTTACGAACCA)(GTTTTAGAGCTAGAAATAGCAAGTTAAAATAAGGCTAGTCCGTT
ATCAACTTGAAAAAGTGGCACCGAGTCGGTGCT) (SEQ ID NO: 3)

Figure 4

GGCCGGGCGCGGTGGCTCACGCCTGTAATCCCAGCACTTTGGGAGGCCGAGACGGGCGGA
TCACGAGGTCAGGAGATCGAGACCATCTTGGCTAACACGGTGAAACCCCGTTTCTACTAA
AAATACAAAAAATTAGCCGGGCGTGTTGGCGGGCGCCTGTAGTCCCAGCTACTTGGGAGG
CTGAGGCAGGAGAATGGCGTGAACCCGGGAGGCGGAGCTTGCAGTGAGCCGAGATTGCG
CCACCGCACTCCAACCTGGGAGACACAGCGAGACTCCGTCTCAAAAAAAAAAAAAAAAA
AAAAAAAAAA (SEQ ID NO: 4)

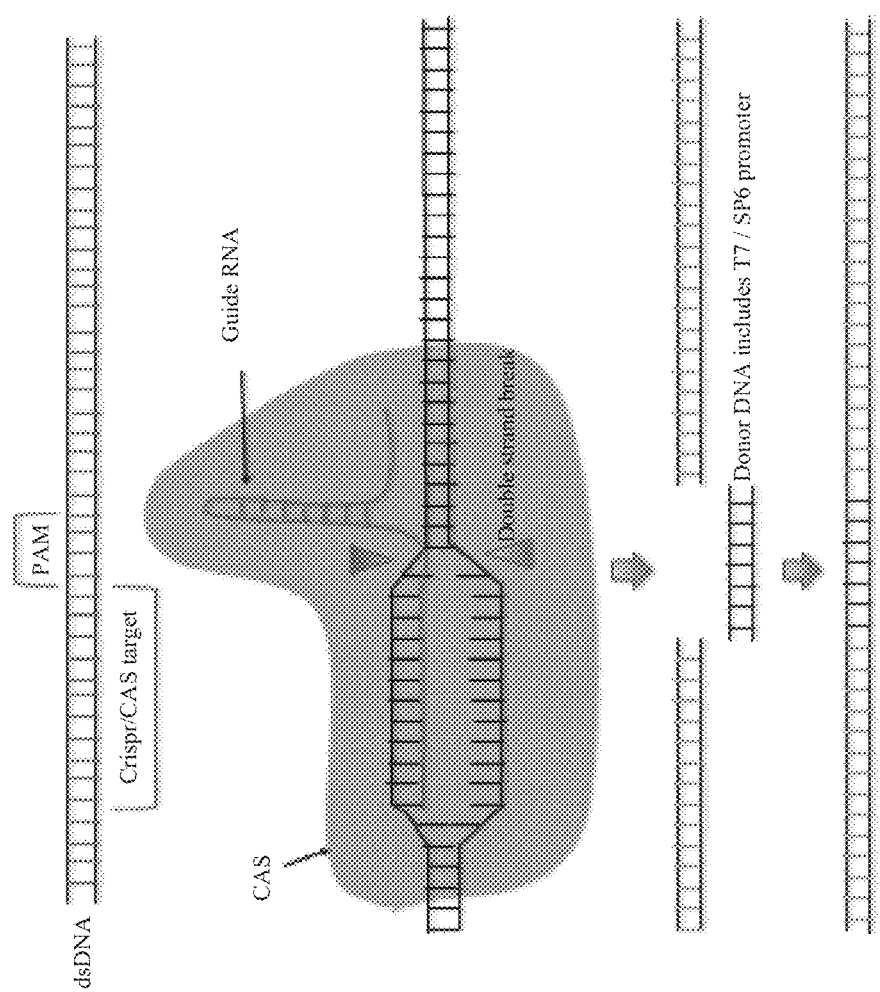

Figure 12

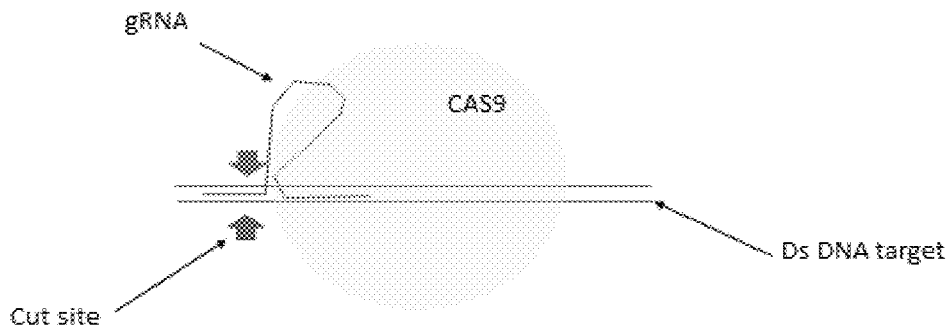

gRNA targets locus of interest, CAS 9 creates a double stranded cut at a defined location.

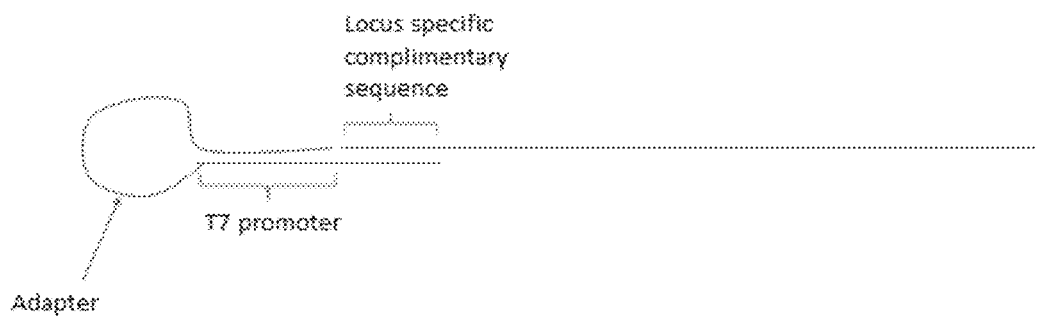

dsDNA target is denatured and T7 adapter with single stranded complementary sequence will hybridize to target sequencing flanking CRISPR cut site. Adapter is ligated to 5' end of target sequence.

IVT produces RNA copies of target DNA locus

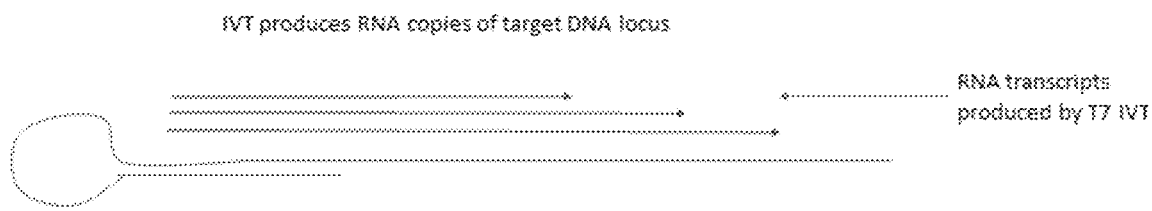

Long RNA is produced through in vitro transcription.

SEQUENCE LISTING

<160> NUMBER OF SEQ ID NOS: 524

<210> SEQ ID NO 1
<211> LENGTH: 6053
<212> TYPE: DNA
<213> ORGANISM: Homo sapiens

<400> SEQUENCE: 1

| | | | | | |
|---|---|---|---|---|---:|
| gggggaggag | ccaagatggc | cgaataggaa | cagctccggt | ctacagctcc | cagcgtgagc | 60 |
| gacgcagaag | acggtgattt | ctgcatttcc | atctgaggta | ccgggttcat | ctcactaggg | 120 |
| agtgccagac | agtgggcgca | ggccagtgtg | tgtgcgcacc | gtgcgcgagc | cgaagcaggg | 180 |
| cgaggcattg | cctcacctgg | gaagcgcaag | gggtcaggga | gttcccttc | tgagtcaaag | 240 |
| aaagggtga | cggtcgcacc | tggaaaatcg | ggtcactccc | acccgaatat | tgcgcttttc | 300 |
| agaccggctt | aagaaacggc | gcaccacgag | actatatccc | acacctggct | cggagggtcc | 360 |
| tacgcccacg | gaatctcgct | gattgctagc | acagcagtct | gagatcaaac | tgcaaggcgg | 420 |
| caacgaggct | gggggagggg | cgcccgccat | tgcccaggct | tgcttaggta | aacaaagcag | 480 |
| ccgggaagct | cgaactgggt | ggagcccacc | acagctcaag | gaggcctgcc | tgcctctgta | 540 |
| ggctccacct | ctgggggcag | ggcacagaca | acaaaaagg | cagcagtaac | ctctgcagac | 600 |
| ttaagtgtcc | ctgtctgaca | gctttgaaga | gagcagtggg | tctcccagca | cgcagctgga | 660 |
| gatctgagaa | cgggcagaca | gactgcctcc | tcaagtgggt | ccctgactcc | tgaccccga | 720 |
| gcagcctaac | tgggaggcac | cccccagcag | gggcacactg | acacctcaca | cggcagggta | 780 |
| ttccaacaga | cctgcagctg | agggtcctgt | ctgttagaag | gaaaactaac | aaccagaaag | 840 |
| gacatctaca | ccgaaaaccc | atctgtacat | caccatcatc | aaagaccaaa | agtagataaa | 900 |
| accacaaaga | tggggaaaaa | acagaacaga | aaaactggaa | actctaaaac | gcagagcgcc | 960 |
| tctcctcctc | caaaggaacg | cagttcctca | ccagcaacag | aacaaagctg | gatggagaat | 1020 |
| gattttgacg | agctgagaga | agaaggcttc | agacgatcaa | attactctga | gctacgggag | 1080 |
| gacattcaaa | ccaaaggcaa | agaagttgaa | actttgaaa | aaatttaga | agaatgtata | 1140 |
| actagaataa | ccaatacaga | gaagtgctta | aaggagctga | tggagctgaa | aaccaaggct | 1200 |
| cgagaactac | gtgaagaatg | cagaagcctc | aggagccgat | gcgatcaact | ggaagaaagg | 1260 |
| gtatcagcaa | tggaagatga | aatgaatgaa | atgaagcgag | aagggaagtt | tagagaaaaa | 1320 |
| agaataaaaa | gaaatgagca | aagcctccaa | gaaatatggg | actatgtgaa | aagaccaaat | 1380 |
| ctacgtctga | ttggtgtacc | tgaaagtgat | gtggagaatg | gaaccaagtt | ggaaaacact | 1440 |
| ctgcaggata | ttatccagga | gaacttcccc | aatctagcaa | ggcaggccaa | cgttcagatt | 1500 |
| caggaaatac | agagaacgcc | acaaagatac | tcctcgagaa | gagcaactcc | aagacacata | 1560 |
| attgtcagat | tcaccaaagt | tgaaatgaag | gaaaaaatgt | taagggcagc | cagagagaaa | 1620 |
| ggtcgggtta | ccctcaaagg | aaagcccatc | agactaacag | tggatctctc | ggcagaaacc | 1680 |
| ctacaagcca | gaagagagtg | ggggccaata | ttcaacattc | ttaaagaaaa | gaattttcaa | 1740 |
| cccagaattt | catatccagc | caaactaagc | ttcataagtg | aaggagaaat | aaaatacttt | 1800 |
| atagacaagc | aaatgttgag | agattttgtc | accaccaggc | ctgccctaaa | agagctcctg | 1860 |
| aaggaagcgc | taaacatgga | aaggaacaac | cggtaccagc | cgctgcaaaa | tcatgccaaa | 1920 |
| atgtaaagac | cattgagact | aggaagaaac | tgcatcaact | aatgagcaaa | atcaccagct | 1980 |
| aacatcataa | tgcaggatc | aaattcacac | ataacaatat | taactttaaa | tataaatgga | 2040 |
| ctaaattctg | caattaaaag | acacagactg | gcaagttgga | taaagagtca | agacccatca | 2100 |

```
gtgtgctgta ttcaggaaac ccatctcacg tgcagagaca cacataggct caaaataaaa    2160
ggatggagga agatctacca agccaatgga aaacaaaaaa aggcagggt tgcaatccta     2220 gtctctgata aaacagactt taaaccaaca aagatcaaaa gagacaaaga aggccattac    2280
ataatggtaa agggatcaat tcaacaagag gagctaacta tcctaaatat ttatgcaccc    2340
aatacaggag cacccagatt cataaagcaa gtcctgagtg acctacaaag agacttagac    2400
tcccacacat taataatggg agactttaac accccactgt caacattaga cagatcaacg    2460
agacagaaag tcaacaagga tacccaggaa ttgaactcag ctctgcacca agcagaccta    2520
atagacatct acagaactct ccaccccaaa tcaacagaat accttttt ttcagcacca     2580 caccacacct attccaaaat tgaccacata gttggaagta aagctctcct cagcaaatgt    2640
aaaagaacag aaattataac aaactatctc tcagaccaca gtgcaatcaa actagaactc    2700
aggattaaga atctcactca aagccgctca actacatgga aactgaacaa cctgctcctg    2760
aatgactact gggtacataa cgaaatgaag gcagaaataa agatgttctt tgaaaccaac    2820
gagaacaaag acaccacata ccagaatctc tgggacgcat tcaaagcagt gtgtagaggg    2880
aaatttatag cactaaatgc ctacaagaga aagcaggaaa gatccaaaat tgacacccta    2940
acatcacaat taaaagaact agaaaagcaa gagcaaacac attcaaaagc tagcagaagg    3000
caagaaataa ctaaaatcag agcagaactg aaggaaatag agacacaaaa acccttcaa    3060 aaaatcaatg aatccaggag ctggtttttt gaaaggatca caaaattga tagaccgcta    3120 gcaagactaa taaagaaaaa aagagagaag aatcaaatag acacaataaa aaatgataaa    3180
ggggatatca ccaccgatcc cacagaaata caaactacca tcagagaata ctacaaacac    3240
ctctacgcaa ataaactaga aaatctagaa gaaatggata cattcctcga cacatacact    3300
ctcccaagac taaaccagga agaagttgaa tctctgaata gaccaataac aggctctgaa    3360
attgtggcaa taatcaatag tttaccaacc aaaaagagtc caggaccaga tggattcaca    3420
gccgaattct accagaggta catggaggaa ctggtaccat tccttctgaa actattccaa    3480
tcaatagaaa aagagggaat cctccctaac tcattttatg aggccagcat cattctgata    3540
ccaaagccgg gcagagacac aaccaaaaaa gagaatttta gaccaatatc cttgatgaac    3600
attgatgcaa aaatcctcaa taaaatactg gcaaaccgaa tccattagca catcaaaaag    3660
cttatccacc atgatcaagt gggcttcatc cctgggatgc aaggctggtt caatatacgc    3720
aaatcaataa atgtaatcca gcatataaac agagccaaag acaaaaacca catgattatc    3780
tcaatagatg cagaaaaagc cttgacaaaa attcaacaac ccttcatgct aaaaactctc    3840
aataaattag gtattgatgg gacgtatttc aaaataataa gagctatcta tgacaaaccc    3900
acagccaata tcatactgaa tgggcaaaaa ctggaagcat tccctttgaa aaccggcaca    3960
agacagggat gccctctctc accgctccta ttcaacatag tgttggaagt tctggccagg    4020
gcaatcaggc aggagaagga aataaagggt attcaattag gaaaagagga agtcaaattg    4080
tccctgtttg cagacgacat gattgtatat ctagaaaacc ccatcgtctc agcccaaaat    4140
ctccttaagc tgataagcaa cttcagcaaa gtctcaggat acaaaatcaa tgtacaaaaa    4200
tcacaagcat tcttatacac caacaacaga caaacagaga gccaaatcat gggtgaactc    4260
ccattcgtaa ttgcttcaaa gagaataaaa tacctaggaa tccaacttac aagggatgtg    4320
aaggacctct tcaaggagaa ctacaaacca ctgctcaagg aaataaaaga ggacacaaac    4380
aaatggaaga acattccatg ctcatgggta ggaagaatca atatcgtgaa aatggccata    4440
```

```
ctgcccaagg taatttacag attcaatgcc atccccatca agctaccaat gactttcttc    4500
acagaattgg aaaaaactac tttaaagttc atatggaacc aaaaaagagc ccgcattgcc    4560
aagtcaatcc taagccaaaa gaacaaagct ggaggcatca cactacctga cttcaaacta    4620
tactacaagg ctacagtaac caaaacagca tggtactggt accaaaacag agatatagat    4680
caatggaaca gaacagagcc ctcagaaata atgccgcata tctacaacta tctgatcttt    4740
gacaaacctg agaaaaacaa gcaatgggga aaggattccc tatttaataa atggtgctgg    4800
gaaaactggc tagccatatg tagaaagctg aaactggatc ccttccttac accttataca    4860
aaaatcaatt caagatggat taaagattta acgttaaac ctaaaaccat aaaaacccta    4920
gaagaaaacc taggcattac cattcaggac ataggcgtgg gcaaggactt catgtcccaaa   4980 acaccaaaag caatggcaac aaaagacaaa attgacaaat gggatctaat taaactaaag    5040
agcttctgca cagcaaaaga aactaccatc agagtgaaca ggcaacctac aacatgggag    5100
aaaattttcg caacctactc atctgacaaa gggctaatat ccagaatcta caatgaactc    5160
aaacaaattt acaagaaaaa aacaaacaac cccatcaaaa agtgggtgaa ggacatgaac    5220
agacacttct caaagaaga catttatgca gccaaaaaac acatgaagaa atgctcatca    5280
tcactggcca tcagagaaat gcaaatcaaa accactatga gatatcatct cacaccagtt    5340
agaatggcaa tcattaaaaa gtcaggaaac aacaggtgct ggagaggatg cggagaaata    5400
ggaacacttt tacactgttg gtgggactgt aaactagttc aaccattgtg gaagtcagtg    5460
tggcgattcc tcagggatct agaactagaa ataccatttg acccagccat cccattactg    5520
ggtatatacc caaatgagta taaatcatgc tgctataaag acacatgcac acgtatgttt    5580
attgcggcac tattcacaat agcaaagact tggaaccaac ccaaatgtcc aacaatgata    5640
gactggatta gaaaatgtg gcacatatac accatggaat actatgcagc cataaaaaat    5700
gatgagttca tatcctttgt agggacatgg atgaaattgg aaaccatcat tctcagtaaa    5760
ctatcgcaag aacaaaaaac caaacaccgc atattctcac tcataggtgg gaattgaaca    5820
atgagatcac atggacacag gaaggggaat atcacactct ggggactgtg gtggggtcgg    5880 gggaggggg agggatagca ttgggagata tacctaatgc tagatgacac attagtgggt    5940
gcagcgcacc agcatggcac atgtatacat atgtaactaa cctgcacaat gtgcacatgt    6000
accctaaaac ttagagtata ataaaaaaaa aaaaaaaaa aaaaaaaaa aaa             6053
```

<210> SEQ ID NO 2
<211> LENGTH: 148
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 2

```
gcttccgggc ccacggccaa gcaacgaggc agacctctgg cgatcccaac gtgccacgct      60
cggcggtcat ggccgtctca atggccgtcc gaccgactag cgcttgctcg acccttgtta     120
cgaaccacgg ttcctgcaac gcacacgg                                         148
```

<210> SEQ ID NO 3
<211> LENGTH: 96
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 3
cgacccttgt tacgaaccag ttttagagct agaaatagca agttaaaata aggctagtcc    60
gttatcaact tgaaaaagtg gcaccgagtc ggtgct                              96

<210> SEQ ID NO 4
<211> LENGTH: 309
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
ggccgggcgc ggtggctcac gcctgtaatc ccagcacttt gggaggccga gacgggcgga    60
tcacgaggtc aggagatcga gaccatcttg gctaacacgg tgaaacccg tttctactaa    120 aaatacaaaa aattagccgg gcgtgttggc gggcgcctgt agtcccagct acttgggagg    180
ctgaggcagg agaatggcgt gaacccggga ggcggagctt gcagtgagcc gagattgcgc    240
caccgcactc caacctggga gacacagcga gactccgtct caaaaaaaaa aaaaaaaaa    300 aaaaaaaaa                                                            309

<210> SEQ ID NO 5
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
taatacgact cactatag                                                   18

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
ttgtagtata gtttgaagtc                                                 20

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
aaaaccctag aagaaaacct                                                 20

<210> SEQ ID NO 8
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
tctttaagaa tgttgaatat                                                 20

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
acagccaata tcatactgaa                                                 20

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
tcacatagtc ccatatttct                                                 20

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
ctacagtaac caaaacagca                                                 20

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
agcaacttca gcaaagtctc                                                 20

<210> SEQ ID NO 13
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
tgacttcaaa ctatactaca                                                 20
```

```
<210> SEQ ID NO 14
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
taagcttttt gatgtgctgc                                            20

<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
cctccctaac tcattttatg                                            20

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
gaagcattcc ctttgaaaac                                            20

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
acctgctcct gaatgactac                                            20

<210> SEQ ID NO 18
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
tgaagttgct tatcagctta                                            20

<210> SEQ ID NO 19
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 19
gagttctgta gatgtctatt                                         20

<210> SEQ ID NO 20
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
tattcacaat agcaaagact                                         20

<210> SEQ ID NO 21
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
ttgtctcttt tgatctttgt                                         20

<210> SEQ ID NO 22
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
ttgaaccagc cttgcatccc                                         20

<210> SEQ ID NO 23
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
aggattccct atttaataaa                                         20

<210> SEQ ID NO 24
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
ttgcccattc agtatgatat                                         20

<210> SEQ ID NO 25
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
gttcttttaa ttgtgatgtt                                                    20

<210> SEQ ID NO 26
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
aagatcaaaa gagacaaaga                                                    20

<210> SEQ ID NO 27
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
ttcacttatg aagcttagtt                                                    20

<210> SEQ ID NO 28
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
aaactaagct tcataagtga                                                    20

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
aaaaatcctc aataaaatac                                                    20

<210> SEQ ID NO 30
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
```
catctattga gataatcatg                                              20

<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
cccagcacca tttattaaat                                              20

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
tcctgaatac agcacactga                                              20

<210> SEQ ID NO 33
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
tgtcttgtgc cagttttcaa                                              20

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
tttgatttgc atttctctga                                              20

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
atccctttac cattatgtaa                                              20

<210> SEQ ID NO 36
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 36
tgagagattt tgtcaccacc                                                    20

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
aatctgacaa ttatgtgtct                                                    20

<210> SEQ ID NO 38
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
cagtttcagc tttctacata                                                    20

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
catatgtaga aagctgaaac                                                    20

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
aatatatatg cacccaatac                                                    20

<210> SEQ ID NO 41
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
gatggtagtt tgtatttctg                                                    20

<210> SEQ ID NO 42
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
agtctgtttt atcagagact                                              20

<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
gccagtctgt gtcttttaat                                              20

<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
cttccaacac tatgttgaat                                              20

<210> SEQ ID NO 45
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
aaactacttt aaagttcata                                              20

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
aatgtggcac atatacacca                                              20

<210> SEQ ID NO 47
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
```
cacattcaaa agctagcaga          20

<210> SEQ ID NO 48
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
cccatcagtg tgctgtattc          20

<210> SEQ ID NO 49
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
atctttcctg ctttctcttg          20

<210> SEQ ID NO 50
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
ctaagccaaa agaacaaagc          20

<210> SEQ ID NO 51
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
tcatccctgg gatgcaaggc          20

<210> SEQ ID NO 52
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
ctctttgaag caattgtgaa          20

<210> SEQ ID NO 53
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 53
gcccatgcct atgtcctgaa                                              20

<210> SEQ ID NO 54
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
tgcctccagc tttgttcttt                                              20

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
tttttccttc atttcaactt                                              20

<210> SEQ ID NO 56
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
aaactaccat cagagtgaac                                              20

<210> SEQ ID NO 57
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
aggaaaacta acaaacagaa                                              20

<210> SEQ ID NO 58
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
tcaaagagaa taaaatacct                                              20
```

```
<210> SEQ ID NO 59
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
aaatgcccac aagagaaagc                                                 20

<210> SEQ ID NO 60
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
aatgactttc ttcacagaat                                                 20

<210> SEQ ID NO 61
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
attcaccaaa gttgaaatga                                                 20

<210> SEQ ID NO 62
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
aattctgtga agaaagtcat                                                 20

<210> SEQ ID NO 63
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
attccaatca atagaaaaag                                                 20

<210> SEQ ID NO 64
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 64
cctgtcatta tgatgttagc                                               20

<210> SEQ ID NO 65
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
ccagctaaca tcataatgac                                               20

<210> SEQ ID NO 66
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
tgacccagcc atcccattac                                               20

<210> SEQ ID NO 67
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
taccattcag gacataggca                                               20

<210> SEQ ID NO 68
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
ctgttctttt acatttgctg                                               20

<210> SEQ ID NO 69
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
gatctgtcta atgttgacag                                               20

<210> SEQ ID NO 70
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 70
gttctagttt gattgcactg                                                   20

<210> SEQ ID NO 71
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ttccctcttt ttctattgat                                                   20

<210> SEQ ID NO 72
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
ttaaaaagtc aggaaacaac                                                   20

<210> SEQ ID NO 73
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
acacaacata ccagaatctc                                                   20

<210> SEQ ID NO 74
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
aggaagatct accaagcaaa                                                   20

<210> SEQ ID NO 75
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
gtaaactagt tcaaccattg                                                   20
```

```
<210> SEQ ID NO 76
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
gtgcaatcaa actagaactc                                                  20

<210> SEQ ID NO 77
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
actcctattc aacatagtgt                                                  20

<210> SEQ ID NO 78
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
gcagagctga gttcaattcc                                                  20

<210> SEQ ID NO 79
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
ccatctcaca ccagttagaa                                                  20

<210> SEQ ID NO 80
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
ccttcacatc ccttgtaagt                                                  20

<210> SEQ ID NO 81
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 81
tatctcaata gatgcagaaa                                          20

<210> SEQ ID NO 82
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
ttaagggcag ccagagagaa                                          20

<210> SEQ ID NO 83
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
ctaaaaactc tcaataaatt                                          20

<210> SEQ ID NO 84
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
tatgtaccca gtagtcattc                                          20

<210> SEQ ID NO 85
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
gcttatccac catgatcaag                                          20

<210> SEQ ID NO 86
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
tggagaggat gtggagaaat                                          20

<210> SEQ ID NO 87
<211> LENGTH: 20
<212> TYPE: DNA
```

```
-continued

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
ctgcagagtg ttttccaact                                              20

<210> SEQ ID NO 88
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
tcagagattc aacttcttcc                                              20

<210> SEQ ID NO 89
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
tctctgaata gaccaataac                                              20

<210> SEQ ID NO 90
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
gaatctgggt gctcctgtat                                              20

<210> SEQ ID NO 91
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
caagttggaa aacactctgc                                              20

<210> SEQ ID NO 92
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
tagatcccat ttgtcaattt                                              20
```

```
<210> SEQ ID NO 93
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
tgaagcccac ttgatcatgg                                               20

<210> SEQ ID NO 94
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
tccaattaaa agacacagac                                               20

<210> SEQ ID NO 95
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
caaaagccaa aattgacaaa                                               20

<210> SEQ ID NO 96
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
gtatataccc agtaatggga                                               20

<210> SEQ ID NO 97
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
gaaataaagg gtattcaatt                                               20

<210> SEQ ID NO 98
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 98
accctcagct gcaggtctgt                                              20

<210> SEQ ID NO 99
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
ccaacttaca agggatgtga                                              20

<210> SEQ ID NO 100
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
attgagagtt tttagcatga                                              20

<210> SEQ ID NO 101
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101 tttttgttt tccatttgct                                               20

<210> SEQ ID NO 102
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
tctcttcaaa gctgtcagac                                              20

<210> SEQ ID NO 103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
attcttccta cccatgagca                                              20

<210> SEQ ID NO 104
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104 aacacttttta cactgttggt                                          20

<210> SEQ ID NO 105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
ctgttttttc cccatctttg                                           20

<210> SEQ ID NO 106
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
caaacaaccc catcaaaaag                                           20

<210> SEQ ID NO 107
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
tttctagttc tagatccctg                                           20

<210> SEQ ID NO 108
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
agaacttccc caatctagca                                           20

<210> SEQ ID NO 109
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
```
tgtgagatgg tatctcattg                                               20

<210> SEQ ID NO 110
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
tttgagttca ttgtagattc                                               20

<210> SEQ ID NO 111
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
ccatgtttag tgcttccttc                                               20

<210> SEQ ID NO 112
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
cagtctgaga tcaaactgca                                               20

<210> SEQ ID NO 113
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
tcagtttcca tgtagttgag                                               20

<210> SEQ ID NO 114
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
ttaatccagt ctatcattgt                                               20

<210> SEQ ID NO 115
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 115
gtctaaaaca ccaaaagcaa                                                    20

<210> SEQ ID NO 116
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
tgccctaaaa gagctcctga                                                    20

<210> SEQ ID NO 117
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
tcacagccga attctaccag                                                    20

<210> SEQ ID NO 118
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
aatgtccaac aatgatagac                                                    20

<210> SEQ ID NO 119
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
ctagattggg gaagttctcc                                                    20

<210> SEQ ID NO 120
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
ttctttatta gtcttgctag                                                    20

<210> SEQ ID NO 121
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
cctcataaaa tgagttaggg                                              20

<210> SEQ ID NO 122
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
gaaaaaatgc tcatcatcac                                              20

<210> SEQ ID NO 123
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
aagaatcaat atcgtgaaaa                                              20

<210> SEQ ID NO 124
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
ggtttgccag tattttattg                                              20

<210> SEQ ID NO 125
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
cttctcgagg agtatctttg                                              20

<210> SEQ ID NO 126
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
```
ttaatgattg ccattctaac                                           20

<210> SEQ ID NO 127
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
ggtaacccga cctttctctc                                           20

<210> SEQ ID NO 128
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
aacaaagcct ccaagaaata                                           20

<210> SEQ ID NO 129
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
tagcccttrg tcagatgagt                                           20

<210> SEQ ID NO 130
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
taaacatgga aaggaacaac                                           20

<210> SEQ ID NO 131
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
ctccaacaga cctgcagctg                                           20

<210> SEQ ID NO 132
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 132
gatgagttca tgtcctttgt                                                    20

<210> SEQ ID NO 133
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
caatcatgtc atctgcaaac                                                    20

<210> SEQ ID NO 134
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
ctcttttagg gcaggcctgg                                                    20

<210> SEQ ID NO 135
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
ttttgcatca atgttcatca                                                    20

<210> SEQ ID NO 136
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
catgaactca tcattttta                                                     20

<210> SEQ ID NO 137
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
attttggaat aggtgtggtg                                                    20
```

```
<210> SEQ ID NO 138
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
aagttctggc cagggcaatc                                              20

<210> SEQ ID NO 139
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
aattcggctg tgaatccatc                                              20

<210> SEQ ID NO 140
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
gtggagccca ccacagctca                                              20

<210> SEQ ID NO 141
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
tttcatccat gtccctacaa                                              20

<210> SEQ ID NO 142
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
aaaacagaga tatagatcaa                                              20

<210> SEQ ID NO 143
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 143
attgatctat atctctgttt                                              20

<210> SEQ ID NO 144
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
taaaatcaga gcagaactga                                              20

<210> SEQ ID NO 145
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
agtagataaa accacaaaga                                              20

<210> SEQ ID NO 146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
gaactacaaa ccactgctca                                              20

<210> SEQ ID NO 147
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
attgaatcta taaattacct                                              20

<210> SEQ ID NO 148
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
agtcagtgtg gcgattcctc                                              20

<210> SEQ ID NO 149
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 149
tgtctgtgcc ctgcccccag                                               20

<210> SEQ ID NO 150
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
cgccacactg acttccacaa                                               20

<210> SEQ ID NO 151
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
tagttttcct tctaacagac                                               20

<210> SEQ ID NO 152
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
aaatgtatat tctgttgatt                                               20

<210> SEQ ID NO 153
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
ctacttttgg tctttgatga                                               20

<210> SEQ ID NO 154
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
agactcccac acaataataa                                               20
```

<210> SEQ ID NO 155
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 155
gaagcccatc agactaacag        20

<210> SEQ ID NO 156
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 156
gcctctgtag gctccacctc        20

<210> SEQ ID NO 157
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 157
tggagcctac agaggcaggc        20

<210> SEQ ID NO 158
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 158
tccaaaattg accacatagt        20

<210> SEQ ID NO 159
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 159
gatttctgca tttccatctg        20

<210> SEQ ID NO 160
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 160
aacctgagaa aaacaagcaa                                           20

<210> SEQ ID NO 161
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
tatttcctga atttgaatgt                                           20

<210> SEQ ID NO 162
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
gaactcagct ctgcaccaag                                           20

<210> SEQ ID NO 163
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
caatacagag aagtgcttaa                                           20

<210> SEQ ID NO 164
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
ccccattgct tgtttttctc                                           20

<210> SEQ ID NO 165
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
ttaccaacca aaaagagtcc                                           20

<210> SEQ ID NO 166
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
atgcacacgt atgtttattg                                            20

<210> SEQ ID NO 167
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
cctttcaaaa aaccagctcc                                            20

<210> SEQ ID NO 168
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
agaccaaatc tacgtctgat                                            20

<210> SEQ ID NO 169
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
ctttaagcac ttctctgtat                                            20

<210> SEQ ID NO 170
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
agtctcccat tattattgtg                                            20

<210> SEQ ID NO 171
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
atacaaaaat taattcaaga                                            20
```

<210> SEQ ID NO 172
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
gcaacctact catctgacaa                                              20

<210> SEQ ID NO 173
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
taatgcctag gttttcttct                                              20

<210> SEQ ID NO 174
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
tggtctaaaa ttctcttttt                                              20

<210> SEQ ID NO 175
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
agtctctttg taggtcactc                                              20

<210> SEQ ID NO 176
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
ctctacaagc cagaagagag                                              20

<210> SEQ ID NO 177
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 177
acaccaatca gacgtagatt                                              20

<210> SEQ ID NO 178
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
gtgaagaatg cagaagcctc                                              20

<210> SEQ ID NO 179
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
cttgaattaa ttttttgtata                                             20

<210> SEQ ID NO 180
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
tattgcctag gttttcttct                                              20

<210> SEQ ID NO 181
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
gacagctttg aagagagcag                                              20

<210> SEQ ID NO 182
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182 aaaatttct cccattctgt                                               20

<210> SEQ ID NO 183
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
ccagttcctc cttgtacctc                                              20

<210> SEQ ID NO 184
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
ggaagaacat tccatgctca                                              20

<210> SEQ ID NO 185
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
gaatgtatat tctgttgatt                                              20

<210> SEQ ID NO 186
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
atcagatagt tgtagatatg                                              20

<210> SEQ ID NO 187
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
taagatcaga gcagaactga                                              20

<210> SEQ ID NO 188
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
```
atattaactt taaatgtaaa                                            20

<210> SEQ ID NO 189
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189 gcatttttc atgtgttttt                                             20

<210> SEQ ID NO 190
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
ttcaaaaaat caatgaatcc                                            20

<210> SEQ ID NO 191
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
caccctccca agactaaacc                                            20

<210> SEQ ID NO 192
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
agattttggg ctgagacaat                                            20

<210> SEQ ID NO 193
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
cactctccca agactaaacc                                            20

<210> SEQ ID NO 194
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 194
gttttcaact tctttgcctt                                            20

<210> SEQ ID NO 195
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
tatgtataca tgtgccatgc                                            20

<210> SEQ ID NO 196
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
cactagggag tgccagacag                                            20

<210> SEQ ID NO 197
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
atcatcctga taccaaagcc                                            20

<210> SEQ ID NO 198
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
gtgtgtctct gcacgtgaga                                            20

<210> SEQ ID NO 199
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
tttctagttt atttgcgtag                                            20

<210> SEQ ID NO 200
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
gatttctgca tttccaactg                                                   20

<210> SEQ ID NO 201
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
tcttttattt ccttgagcag                                                   20

<210> SEQ ID NO 202
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
tcacgtgcag agacacacat                                                   20

<210> SEQ ID NO 203
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
cactccagac cctgtttgcc                                                   20

<210> SEQ ID NO 204
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
atattaacct taaatgtaaa                                                   20

<210> SEQ ID NO 205
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
```

```
cagcatttgc ttgtctgtaa                                          20
```

<210> SEQ ID NO 206
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206

```
gagatccgct gttagtctga                                          20
```

<210> SEQ ID NO 207
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207

```
cagcatgatt tatagtcctt                                          20
```

<210> SEQ ID NO 208
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208

```
ccctacaagc cagaagagag                                          20
```

<210> SEQ ID NO 209
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209

```
atacaaaaat caattcaaga                                          20
```

<210> SEQ ID NO 210
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210

```
atttagccca tttacattta                                          20
```

<210> SEQ ID NO 211
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 211 tttttttgttg tgtctctgcc                                              20

<210> SEQ ID NO 212
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
aggggtcagg gacccacttg                                               20

<210> SEQ ID NO 213
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
tttctagttt atttgcatag                                               20

<210> SEQ ID NO 214
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
cttgaattga ttttttgtata                                              20

<210> SEQ ID NO 215
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
tgaatgtgtc ccagagattc                                               20

<210> SEQ ID NO 216
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
aaaattttct cccattttgt                                               20
```

```
<210> SEQ ID NO 217
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
tgttgtgtct ttgttctcgt                                              20

<210> SEQ ID NO 218
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
agcaaagcct ccaagaaata                                              20

<210> SEQ ID NO 219
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
aagttctggc cagggcaatt                                              20

<210> SEQ ID NO 220
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
attgaatctg taaattacct                                              20

<210> SEQ ID NO 221
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
agactcccac acattaataa                                              20

<210> SEQ ID NO 222
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 222
ccattctccc catcactttc                                            20

<210> SEQ ID NO 223
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
gctctctgtt tgtctgttat                                            20

<210> SEQ ID NO 224
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
agtctcccat tattaatgtg                                            20

<210> SEQ ID NO 225
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
gtacagatgg gttttggtg                                             20

<210> SEQ ID NO 226
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
tgcctcccag ttaggctgct                                            20

<210> SEQ ID NO 227
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
cccactctct tctggcttgt                                            20

<210> SEQ ID NO 228
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 228
gctgatggag ctgaaaacca                                              20

<210> SEQ ID NO 229
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
actccctagt gagatgaacc                                              20

<210> SEQ ID NO 230
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
ttcaaaaaat taatgaatcc                                              20

<210> SEQ ID NO 231
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
cacctatgag tgagaatatg                                              20

<210> SEQ ID NO 232
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
acattcaaag cagtgtgtag                                              20

<210> SEQ ID NO 233
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
aacattccat gctcatgggt                                              20
```

<210> SEQ ID NO 234
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 234
cttctcctgc ctaattgccc                                          20

<210> SEQ ID NO 235
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 235
tttgtttacc taagcaagcc                                          20

<210> SEQ ID NO 236
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 236
tcttttattt cattgagcag                                          20

<210> SEQ ID NO 237
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 237
actgctcaat gaaataaaag                                          20

<210> SEQ ID NO 238
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 238
cctgaaagtg atggggagaa                                          20

<210> SEQ ID NO 239
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 239
tagttttcct tctaacagtc                                          20

<210> SEQ ID NO 240
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
attttggcat gattttgcag                                          20

<210> SEQ ID NO 241
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
ctttggttct gtttatatgc                                          20

<210> SEQ ID NO 242
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
gacacaataa aaaatgataa                                          20

<210> SEQ ID NO 243
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
tttcttccag ttgatcgcat                                          20

<210> SEQ ID NO 244
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
cttttcaaaa aaccagctcc                                          20

<210> SEQ ID NO 245
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
ttcacgtagt tctcgagcct                                                20

<210> SEQ ID NO 246
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
gagcgcctct cctcctccaa                                                20

<210> SEQ ID NO 247
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
tcagatctcc agctgcgtgc                                                20

<210> SEQ ID NO 248
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
aattgaacaa tgagaacaca                                                20

<210> SEQ ID NO 249
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
atgaatgaaa tgaagcgaga                                                20

<210> SEQ ID NO 250
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
cagtttcttc ctagtctcga                                                20
```

<210> SEQ ID NO 251
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
caccgcatat tctcactcat                                           20

<210> SEQ ID NO 252
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
ctcaaaaccg ctcaactaca                                           20

<210> SEQ ID NO 253
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
tccacccagt tcgagcttcc                                           20

<210> SEQ ID NO 254
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
tgttgtgtct ttgttctcat                                           20

<210> SEQ ID NO 255
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
gatgcgatca actggaagaa                                           20

<210> SEQ ID NO 256
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 256
gtaccagtac catgctgttt                                               20

<210> SEQ ID NO 257
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
aaaaaacaga gcagaaaaac                                               20

<210> SEQ ID NO 258
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
ctttggtatc aggatgatgc                                               20

<210> SEQ ID NO 259
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
aaaaaacaga acagaaaaac                                               20

<210> SEQ ID NO 260
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
gtgctttact tccaactatg                                               20

<210> SEQ ID NO 261
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
tagataaaac cacaaagatg                                               20

<210> SEQ ID NO 262
<211> LENGTH: 20

-continued

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262 tgaccccga gcagcctaac                                            20

<210> SEQ ID NO 263
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
aatttggcat gtttttgcag                                           20

<210> SEQ ID NO 264
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
taaaagagga tacaaacaaa                                           20

<210> SEQ ID NO 265
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
gcattcaaag cagtgtgtag                                           20

<210> SEQ ID NO 266
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
gaggaactgc gttcctttgg                                           20

<210> SEQ ID NO 267
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
tttgacgagc tgagagaaga                                               20

<210> SEQ ID NO 268
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
ctttggtatc agaatgatgc                                               20

<210> SEQ ID NO 269
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
attcttccta tccatgagca                                               20

<210> SEQ ID NO 270
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
tccctttcct agtcaaagaa                                               20

<210> SEQ ID NO 271
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
aaaacagaga tatagaccaa                                               20

<210> SEQ ID NO 272
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
cttctcctgc ctgattgccc                                               20

<210> SEQ ID NO 273
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 273
tgggagtgac ccgatttcc                                                    20

<210> SEQ ID NO 274
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
atgtaaagac catcgagact                                                   20

<210> SEQ ID NO 275
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
ccattctccc cgtcactttc                                                   20

<210> SEQ ID NO 276
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
tcaccatcat caaagaccaa                                                   20

<210> SEQ ID NO 277
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
attattatac tttaagtttt                                                   20

<210> SEQ ID NO 278
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
tcaatttcag agcctgttat                                                   20

<210> SEQ ID NO 279
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
gctctctgtt tgtctgttgt                                            20

<210> SEQ ID NO 280
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
aacgagacag aaagtcaaca                                            20

<210> SEQ ID NO 281
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
cagcatgatt tataatcctt                                            20

<210> SEQ ID NO 282
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
gatcaaatta ctctgagcta                                            20

<210> SEQ ID NO 283
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
gatgcaataa aaaatgataa                                            20

<210> SEQ ID NO 284
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
```
ctttggctct gtttatatgc                                           20

<210> SEQ ID NO 285
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
tgtcacccct ttctttgact                                           20

<210> SEQ ID NO 286
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
ggtcagggac ccacttgagg                                           20

<210> SEQ ID NO 287
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
ctctgagaca aaacttccag                                           20

<210> SEQ ID NO 288
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
ctggcctcat aaaatgagtt                                           20

<210> SEQ ID NO 289
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
cttcatccat gtccctacaa                                           20

<210> SEQ ID NO 290
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 290
cctgaaagtg acggggagaa                                                 20

<210> SEQ ID NO 291
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
cacctatgag tgagaacatg                                                 20

<210> SEQ ID NO 292
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
tatttcctga atctgaacgt                                                 20

<210> SEQ ID NO 293
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
aggagccaag atggccgaat                                                 20

<210> SEQ ID NO 294
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
aagaatcaat atcatgaaaa                                                 20

<210> SEQ ID NO 295
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
gccattgccc aggcttgctt                                                 20
```

```
<210> SEQ ID NO 296
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
cgcagctgga gatctgagaa                                               20

<210> SEQ ID NO 297
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
aattgaacaa tgagatcaca                                               20

<210> SEQ ID NO 298
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
caatcatgtc gtctgcaaac                                               20

<210> SEQ ID NO 299
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
agaccggagc tgttcctatt                                               20

<210> SEQ ID NO 300
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
tatttcctga atctgaatgt                                               20

<210> SEQ ID NO 301
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 301
tgccttacaa gagctcctga                                                    20

<210> SEQ ID NO 302
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
ttgggagagt gtatgtgtcg                                                    20

<210> SEQ ID NO 303
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
ggaaggggaa catcacactc                                                    20

<210> SEQ ID NO 304
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
taaatgtgtc ccagagattc                                                    20

<210> SEQ ID NO 305
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
aggtgtcagt gtgcccctgc                                                    20

<210> SEQ ID NO 306
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
ttaggattga cttggcgatg                                                    20

<210> SEQ ID NO 307
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 307
ttccaacaga cctgcagctg                                                     20

<210> SEQ ID NO 308
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
aacctgacaa aaacaagcaa                                                     20

<210> SEQ ID NO 309
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
tatgtataca tgtgccatgt                                                     20

<210> SEQ ID NO 310
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
aacctgacaa aaacaagaaa                                                     20

<210> SEQ ID NO 311
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
ttaatgatcg ccattctaac                                                     20

<210> SEQ ID NO 312
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
gtccttcgcc cacttttga                                                      20
```

<210> SEQ ID NO 313
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
tccaaaattg accacatact                                                  20

<210> SEQ ID NO 314
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
agattttggg ctgagacgat                                                  20

<210> SEQ ID NO 315
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
tgaatgcgtc ccagagattc                                                  20

<210> SEQ ID NO 316
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
agactggagc tgttcctatt                                                  20

<210> SEQ ID NO 317
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
atactatgca gccataaaaa                                                  20

<210> SEQ ID NO 318
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
gggcagactg acacctcaca                                          20

<210> SEQ ID NO 319
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
atcctttgcc cacttttga                                           20

<210> SEQ ID NO 320
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
ggaaggggaa tatcacactc                                          20

<210> SEQ ID NO 321
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
acgcagttcc tcaccagcaa                                          20

<210> SEQ ID NO 322
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
aatgctagat gacgagttag                                          20

<210> SEQ ID NO 323
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
gacagctttg aagagagtag                                          20

<210> SEQ ID NO 324
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
gagctttact tccaactatg                                               20

<210> SEQ ID NO 325
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
catgaactca tccttttta                                                20

<210> SEQ ID NO 326
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
ctaactcgtc atctagcatt                                               20

<210> SEQ ID NO 327
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
atccagcttt gttccgttgc                                               20

<210> SEQ ID NO 328
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
agtctctttg taggtctcta                                               20

<210> SEQ ID NO 329
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
ccatgtttag cgcttccttc                                               20
```

<210> SEQ ID NO 330
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 330
ccccattgct tgtttttgtc                                               20

<210> SEQ ID NO 331
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 331
gagctttact tccaagtatg                                               20

<210> SEQ ID NO 332
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 332
gacgcaataa aaaatgataa                                               20

<210> SEQ ID NO 333
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 333
ctaggttggg gaagttctcc                                               20

<210> SEQ ID NO 334
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 334
atcagatggt tgtagatgtg                                               20

<210> SEQ ID NO 335
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 335
ccccatttct tgtttttgtc                                              20

<210> SEQ ID NO 336
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
gggcacactg acacctcaca                                              20

<210> SEQ ID NO 337
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
ctacctttgg tctttgatga                                              20

<210> SEQ ID NO 338
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
gactaaaaca ccaaaagcaa                                              20

<210> SEQ ID NO 339
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
tttctagttc tagatccttg                                              20

<210> SEQ ID NO 340
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
gaaaaaatgc tcaccatcac                                              20

<210> SEQ ID NO 341
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
ttaggattga cttggcaatg                                              20

<210> SEQ ID NO 342
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
ttttgtctca gaggagtacc                                              20

<210> SEQ ID NO 343
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
acatttaaag cagtgtgtag                                              20

<210> SEQ ID NO 344
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
ccagctcctc cttgtacctc                                              20

<210> SEQ ID NO 345
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
ctcttgtaag gcaggcctgg                                              20

<210> SEQ ID NO 346
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
```

-continued gagatctgct gttagtctga                                          20

<210> SEQ ID NO 347
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
gagatcagct gttagtctga                                          20

<210> SEQ ID NO 348
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
agggctctgt tctgttccat                                          20

<210> SEQ ID NO 349
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
aacgagacag aaagttaaca                                          20

<210> SEQ ID NO 350
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
ctaagcaaaa agaacaaagc                                          20

<210> SEQ ID NO 351
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
tttttccttc atttcaacct                                          20

<210> SEQ ID NO 352
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 352
ccagctcctc tttgtacctc                                                    20

<210> SEQ ID NO 353
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
gttctaattt gattgcactg                                                    20

<210> SEQ ID NO 354
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
aagaatcaat attgtgaaaa                                                    20

<210> SEQ ID NO 355
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
gtgcaatcaa attagaactc                                                    20

<210> SEQ ID NO 356
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
agcgtgagcg acgcagaaga                                                    20

<210> SEQ ID NO 357
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
tttgacgagt tgagagaaga                                                    20

<210> SEQ ID NO 358
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
caaaagacaa aattgacaaa                                                   20

<210> SEQ ID NO 359
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
catcattctg ataccaaagc                                                   20

<210> SEQ ID NO 360
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
cagctttgtt cttttttgctt                                                  20

<210> SEQ ID NO 361
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
tcttttgttg ccattgcttt                                                   20

<210> SEQ ID NO 362
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
gactgttgtg gggtgggggg                                                   20

<210> SEQ ID NO 363
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
```
gtgtgtctct gcatgtgaga                                                  20

<210> SEQ ID NO 364
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
tatttaccca gtagtcattc                                                  20

<210> SEQ ID NO 365
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
tcacagccaa attctaccag                                                  20

<210> SEQ ID NO 366
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
gtcttctgcg tcgctcacgc                                                  20

<210> SEQ ID NO 367
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
ctcaaaacca ctcaactaca                                                  20

<210> SEQ ID NO 368
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
tttctcttgc ctgattgccc                                                  20

<210> SEQ ID NO 369
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 369
acaatttcag ctcctgttat                                           20

<210> SEQ ID NO 370
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
agtttgccag tattttattg                                           20

<210> SEQ ID NO 371
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
ctaaaaactc tcaataaact                                           20

<210> SEQ ID NO 372
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
agaacttccc caacctagca                                           20

<210> SEQ ID NO 373
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
tttctagttt atttgtgtag                                           20

<210> SEQ ID NO 374
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
ttgggagggt gtatgtgtcc                                           20
```

```
<210> SEQ ID NO 375
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
caatgcagag aagtccttaa                                                 20

<210> SEQ ID NO 376
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
acctactcaa gcctcagcaa                                                 20

<210> SEQ ID NO 377
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
tcacatgcag agacacacat                                                 20

<210> SEQ ID NO 378
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
gagcacctct cctcctccaa                                                 20

<210> SEQ ID NO 379
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
tccctttccg agtcaaagaa                                                 20

<210> SEQ ID NO 380
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 380
cggcagcgag gctgggggag                                              20

<210> SEQ ID NO 381
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
gtccaaaaca ccaaaagcaa                                              20

<210> SEQ ID NO 382
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
gcattttttc atgtgtctgt                                              20

<210> SEQ ID NO 383
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
catcatcctg ataccaaagc                                              20

<210> SEQ ID NO 384
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
cccaattaaa agacacagac                                              20

<210> SEQ ID NO 385
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
acaatttcag atcctgttat                                              20

<210> SEQ ID NO 386
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 386
tcacagctga attctaccag                                                     20

<210> SEQ ID NO 387
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
ttaccaacca aaaaaagtcc                                                     20

<210> SEQ ID NO 388
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
gtgtgtctct gcacatgaga                                                     20

<210> SEQ ID NO 389
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
gcctctgtag actccacctc                                                     20

<210> SEQ ID NO 390
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
aggtgtcagt ctgcccctac                                                     20

<210> SEQ ID NO 391
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
actgacctgc gcccactgtc                                                     20
```

<210> SEQ ID NO 392
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 392
tcatgtgcag agacacacat                                              20

<210> SEQ ID NO 393
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 393
ggtaacctga cctttctctc                                              20

<210> SEQ ID NO 394
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 394
gcaatctact catctgacaa                                              20

<210> SEQ ID NO 395
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 395
caccgcatgt tctcactcat                                              20

<210> SEQ ID NO 396
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 396
tagcaatcag cgagactccg                                              20

<210> SEQ ID NO 397
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 397
aaatgaagga aaaaatgtta                                        20

<210> SEQ ID NO 398
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
acaaagagaa taaaatacct                                        20

<210> SEQ ID NO 399
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
ttaatccagt ctatcattga                                        20

<210> SEQ ID NO 400
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
gtaaattagt tcaaccattg                                        20

<210> SEQ ID NO 401
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
aggaccctcc gagccaggtg                                        20

<210> SEQ ID NO 402
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
cgtcacccct ttctttgact                                        20

<210> SEQ ID NO 403
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
atgagttcat gtcctttgta                                                   20

<210> SEQ ID NO 404
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
acaatttcag agcctgttat                                                   20

<210> SEQ ID NO 405
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
ccattctccc tgtcactttc                                                   20

<210> SEQ ID NO 406
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
gatctgtcta atattgacag                                                   20

<210> SEQ ID NO 407
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
aatgtccatc aatgatagac                                                   20

<210> SEQ ID NO 408
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
ctcggagggt cctacgccca                                                   20
```

<210> SEQ ID NO 409
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 409
tttaagttct ttgtagattc            20

<210> SEQ ID NO 410
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 410
caccagcaac agaacaaagc            20

<210> SEQ ID NO 411
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 411
tcatctcaca ccagttagaa            20

<210> SEQ ID NO 412
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 412
agaccaaatc tacatctgat            20

<210> SEQ ID NO 413
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 413
gagatccact gttagtctga            20

<210> SEQ ID NO 414
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 414
tgacccagca atcccattac                                              20

<210> SEQ ID NO 415
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
atccagcttt gttccattgc                                              20

<210> SEQ ID NO 416
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
ggaaggggaa catcacacac                                              20

<210> SEQ ID NO 417
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
gcattttttc atgtgtcttt                                              20

<210> SEQ ID NO 418
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
ctcaaaactg ctcaactaca                                              20

<210> SEQ ID NO 419
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
tgcctcccag ttaggctact                                              20

<210> SEQ ID NO 420
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
tttattatac tttaagtttt                                                    20

<210> SEQ ID NO 421
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
cctgatggag ctgaaaacca                                                    20

<210> SEQ ID NO 422
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
gtccagcttt gttccattgc                                                    20

<210> SEQ ID NO 423
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
gtcctttgcc cacttttga                                                     20

<210> SEQ ID NO 424
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
acaccaatca gatgtagatt                                                    20

<210> SEQ ID NO 425
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
```

```
cagctccatc aggtcccttta                                              20

<210> SEQ ID NO 426
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
gagtgcctct cctcctccaa                                               20

<210> SEQ ID NO 427
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
agattttggg ctgagatgat                                               20

<210> SEQ ID NO 428
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
aattcagctg tgaatccatc                                               20

<210> SEQ ID NO 429
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
tattgggtgc atatatattt                                               20

<210> SEQ ID NO 430
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
cctgaaagtg acagggagaa                                               20

<210> SEQ ID NO 431
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 431
aaaacaaccc catcaaaaag                                              20

<210> SEQ ID NO 432
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
ttaatgatca ccattctaac                                              20

<210> SEQ ID NO 433
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
ctaccaacca aaaaaagtcc                                              20

<210> SEQ ID NO 434
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
ctgaagagtg ttttccaact                                              20

<210> SEQ ID NO 435
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
cttctcaagg agtatctttg                                              20

<210> SEQ ID NO 436
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
cagactaaca gctgatctct                                              20

<210> SEQ ID NO 437
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
caccgtgcgc gagccgaagc                                                      20

<210> SEQ ID NO 438
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
cttcatccat gtccctgcaa                                                      20

<210> SEQ ID NO 439
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
ggcaatgcct cgccctgctt                                                      20

<210> SEQ ID NO 440
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
attgaatcta taaattactt                                                      20

<210> SEQ ID NO 441
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
ctctttgtag caattgtgaa                                                      20

<210> SEQ ID NO 442
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
```
cttcttgagg agtatctttg                                          20

<210> SEQ ID NO 443
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
tttttgcatc gatgttcatc                                          20

<210> SEQ ID NO 444
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
cagctccatc aggtcattta                                          20

<210> SEQ ID NO 445
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
gagtgagaac atgcagtgtt                                          20

<210> SEQ ID NO 446
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
agtcaggaaa caacagatgc                                          20

<210> SEQ ID NO 447
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
cgatagtttg ctgagaatga                                          20

<210> SEQ ID NO 448
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 448
aattttcagc ttttctgctc                                               20

<210> SEQ ID NO 449
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
atacccagta atgggattgc                                               20

<210> SEQ ID NO 450
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
gaggagctgc gttcctttgg                                               20

<210> SEQ ID NO 451
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
aattgaacaa tgagaacact                                               20

<210> SEQ ID NO 452
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
aatgctaaat gacgagttaa                                               20

<210> SEQ ID NO 453
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453 tttttttgctt tccatttgct                                              20
```

```
<210> SEQ ID NO 454
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
atgaatgaaa tgaagtgaga                                              20

<210> SEQ ID NO 455
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
attctcagca aactatcgca                                              20

<210> SEQ ID NO 456
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
caagttggaa aacactcttc                                              20

<210> SEQ ID NO 457
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
atcattctga taccaaagcc                                              20

<210> SEQ ID NO 458
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
acaacctact catctgacaa                                              20

<210> SEQ ID NO 459
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 459
tagcatcaac atcaacaaaa                                               20

<210> SEQ ID NO 460
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
cagtttcttc ctagccttga                                               20

<210> SEQ ID NO 461
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
aatttggctg tgaatccatc                                               20

<210> SEQ ID NO 462
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
tttgtggttt tatctacctt                                               20

<210> SEQ ID NO 463
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
gctgatggag ctgaaagcca                                               20

<210> SEQ ID NO 464
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
ttaactcgtc atttagcatt                                               20

<210> SEQ ID NO 465
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 465
tgatagtttg ctgagaatga                                                  20

<210> SEQ ID NO 466
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
gttttgccag tattttattg                                                  20

<210> SEQ ID NO 467
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
atccagcttt gttctgttgc                                                  20

<210> SEQ ID NO 468
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
aagaacttgc tttatgaatc                                                  20

<210> SEQ ID NO 469
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
cctgacccct tgcgcttccc                                                  20

<210> SEQ ID NO 470
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
ttgggagggt gtatgtgtcg                                                  20
```

<210> SEQ ID NO 471
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
cagactaaca gcagatctct                                              20

<210> SEQ ID NO 472
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
ttgctgcctg atccttcctc                                              20

<210> SEQ ID NO 473
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
tctaaaattg accacataat                                              20

<210> SEQ ID NO 474
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
ctcaaagccg ctcaactaca                                              20

<210> SEQ ID NO 475
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
atacaaaaat taactcaaga                                              20

<210> SEQ ID NO 476
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
acagacggca cctggaaaat                                              20

<210> SEQ ID NO 477
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477
tcaccaacat caaagaccaa                                              20

<210> SEQ ID NO 478
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
gtccagcttt gttccgttgc                                              20

<210> SEQ ID NO 479
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
atacccaggc aaacagggtc                                              20

<210> SEQ ID NO 480
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
cgccacactg tcttccacaa                                              20

<210> SEQ ID NO 481
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
cttccaatac tatgttgaat                                              20

<210> SEQ ID NO 482
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
agcagccggg aagctcgaac                                          20

<210> SEQ ID NO 483
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
actcctattc aacatagtat                                          20

<210> SEQ ID NO 484
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
gtgttttact tccaattatg                                          20

<210> SEQ ID NO 485
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
aaagggatca attcaacaag                                          20

<210> SEQ ID NO 486
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
aatgagacag aaagttaaca                                          20

<210> SEQ ID NO 487
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
gacggacgca cctggaaaat                                          20
```

<210> SEQ ID NO 488
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
cttgagttaa tttttgtata                                            20

<210> SEQ ID NO 489
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
aaaattttct cccatgttgt                                            20

<210> SEQ ID NO 490
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
gaaaatcctc aataaaatac                                            20

<210> SEQ ID NO 491
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
tttctcctgc ctgattgccc                                            20

<210> SEQ ID NO 492
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
atattagccc tttgtcagat                                            20

<210> SEQ ID NO 493
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 493
ggtaacccaa cctttctctc                                              20

<210> SEQ ID NO 494
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
aaactatcat cagagtgaac                                              20

<210> SEQ ID NO 495
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
aaaacagata tatagaccaa                                              20

<210> SEQ ID NO 496
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
tgcctcacct gggaagcgca                                              20

<210> SEQ ID NO 497
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
tgccattgct tttggtgttt                                              20

<210> SEQ ID NO 498
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
aggaagatct accaagccaa                                              20

<210> SEQ ID NO 499
<211> LENGTH: 20

-continued

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
tgcctttttt tgttttccat                                              20

<210> SEQ ID NO 500
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
attctcagca aactatcaca                                              20

<210> SEQ ID NO 501
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
ctggactttt tttggttggt                                              20

<210> SEQ ID NO 502
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
cagtttcttc ctagcctcga                                              20

<210> SEQ ID NO 503
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
taggaacact tttacactgt                                              20

<210> SEQ ID NO 504
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
acgagactat atcccacacc                                           20

<210> SEQ ID NO 505
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
gaatattgcg cttttcagac                                           20

<210> SEQ ID NO 506
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
tttgagttct ttgtagattc                                           20

<210> SEQ ID NO 507
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
atgcacatgt atgtttattg                                           20

<210> SEQ ID NO 508
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
tcagggattc aacttcttcc                                           20

<210> SEQ ID NO 509
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
atgcacacat atgtttattg                                           20

<210> SEQ ID NO 510
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 510
gcagggcata gctgaacaaa                                                    20

<210> SEQ ID NO 511
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
tcagatctcc agctgcatgc                                                    20

<210> SEQ ID NO 512
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
aataacaagt tctgaaattg                                                    20

<210> SEQ ID NO 513
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
tgtgagatga tatctcatag                                                    20

<210> SEQ ID NO 514
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
atcatcctga taccaaaacc                                                    20

<210> SEQ ID NO 515
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
aggcctctgt tctgttccat                                                    20
```

```
<210> SEQ ID NO 516
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516 tgaccccga gtagcctaac                                                  20

<210> SEQ ID NO 517
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
gcccacgcct atgtcctgaa                                                 20

<210> SEQ ID NO 518
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
tcaatttcag aacttgttat                                                 20

<210> SEQ ID NO 519
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
taccattcag gacataggcg                                                 20

<210> SEQ ID NO 520
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
caccacatgt tctcactcat                                                 20

<210> SEQ ID NO 521
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 521
aggaccctct gagccaggtg                                                  20

<210> SEQ ID NO 522
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 522
cataattgtc agattcacca                                                  20

<210> SEQ ID NO 523
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
gaagacctta aatgacctga                                                  20

<210> SEQ ID NO 524
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
actagaaaat ctagaagaaa                                                  20
```

METHOD FOR TARGET SPECIFIC RNA TRANSCRIPTION OF DNA SEQUENCES

RELATED APPLICATIONS

The present application claims the benefit of U.S. Provisional Application Ser. No. 62/545,876, filed Aug. 15, 2017, and is a Continuation-in-part and claims the benefit of International Patent Application PCT/US2017/17530, filed Feb. 10, 2017, which claims the benefit of U.S. Provisional Application Ser. No. 62/294,875, filed Feb. 12, 2016, the contents of which are each hereby incorporated by reference in their entirety.

SEQUENCE LISTING

The instant application contains a Sequence Listing which has been submitted electronically in ASCII format and k hereby incorporated by reference in its entirety. Said ASCII copy, created on Feb. 7, 2019, is named 51622-704-501-SequenceListing.txt and is 144,202 bytes in size.

BACKGROUND

The disclosure herein relates to the field of molecular biology, such as amplification and identification of nucleic acid sequence adjacent to repetitive sequence in a nucleic acid sample.

PCR, or variants of PCR technology along with hybrid capture are dominant methods of targeted sequencing. Although widely used, both have limitations for long read sequencers. Hybrid capture uses short RNA or DNA probes with biotin to hybridize to target DNA and "pull down" the sequences of interest. For long target sequences, this approach is inefficient, both because many oligonucleotide probes are required and because the process often results in physical shearing of the long DNA molecules during the pulldown process. These defects limit the length of the contiguous sequencer read using single molecule technologies.

Long range PCR has been used as an alternative, but also presents challenges. Long range PCR is hard to multiplex. Often, one loses the ability to detect large chromosomal events such as translocations due to the requirement of opposing PCR primers on opposite strands outside of the target region. In addition, the clonal amplification of PCR limits sensitivity to detect low frequency somatic variation in a heterogeneous sample such as a tumor, and may propagate polymerase errors such as point mutations or translocations from the early cycles of the reaction. Further, long-range PCR sometimes exhibits template switching, creating errors in the amplification product.

SUMMARY

Advances in genome sequencing technologies have greatly increased our understanding of human genetic variation and its contribution to disease. Short read DNA sequencing technologies (Illumina, Thermo Fisher, Qiagen) produce billions of short reads resulting in the routine identification of single nucleotide polymorphisms and small insertions and deletions. These short read sequencing technologies have not shown a sensitivity to detect more complex variation such as large scale chromosomal rearrangements, translocations and mobile element rearrangements. Long read sequencing technologies (Pacific Biosciences, Oxford Nanopore) have shown the ability to generate single molecule read lengths in excess of 10,000 base pairs, but do not have the capacity to sequence and assemble a full human genome. Targeted strategies disclosed herein take advantage of these longer read lengths.

Here we describe methods of long range target specific amplification where only the original template is amplified to produce increased copies of the original target sequence relative to the sample DNA sequence. Amplified products are derived directly from the sample template rather than from synthesized amplification intermediates or previously synthesized copies of the sample template. As a result synthesized copies do not incorporate errors from a prior synthesis reaction. This dramatically reduces the chance that early errors may be differentially amplified during a reaction. Because synthesis products do not serve as templates, any errors in synthesis are independently derived, and are unlikely to match from one molecule to the next. Accordingly by comparing synthesized products, one can readily identify errors in synthesis and more readily derive the sample sequence.

The disclosed subject matter is summarized in part in the listing of the claims which accompanies this disclosure.

Provided herein are methods of determining a sequence adjacent to a region of known sequence of a nucleic acid molecule. Some such methods comprise a) attaching a nucleic acid fragment comprising promoter sequence at the known region of the nucleic acid molecule; b) contacting the nucleic acid fragment to an RNA polymerase directed by the promoter; and c) synthesizing a plurality of RNA molecules; wherein a consensus sequence of the plurality of RNA molecules represents the sequence adjacent to the known region of a nucleic acid molecule. Optionally, the consensus sequence is at least 10 kilobases in length. Sometimes, the method comprises treating the nucleic acid molecule using a DNase subsequent to synthesizing the plurality of RNA molecules. Alternately or in combination, the method comprises reverse-transcribing the plurality of RNA molecules. The method sometimes comprises determining nucleic acid sequences of the plurality of RNA molecules. Optionally, the consensus sequence of the plurality of RNA molecules comprises sequence of molecules synthesized directly from the nucleic acid molecule. Alternately or in combination, the attaching comprises inserting the nucleic acid fragment comprising promoter sequence at the known region of the nucleic acid molecule. In some cases, the attaching comprises inserting the nucleic acid fragment comprising promoter sequence at the region of known sequence of the nucleic acid molecule. Optionally, the attaching comprises sequence-specific cleavage of the region of known sequence of the nucleic acid molecule. Alternately or in combination, the attaching comprises contacting the known region of the nucleic acid molecule to a CRISPR nucleic acid-protein complex. Optionally, the CRISPR nucleic acid-protein complex comprises a guide RNA comprising SEQ ID NO: 3. In some cases, the attaching comprises ligating the nucleic acid fragment comprising promoter sequence. Sometimes the nucleic acid fragment comprising promoter sequence comprises a viral promoter. Optionally, the viral promoter binds a viral RNA polymerase and is at least one promoter selected from the list consisting of T7, T3, T7lac, SP6, pL, CMV, SV40, and CaMV35S. Alternately or in combination, the nucleic acid fragment comprising promoter sequence comprises a bacterial promoter. In some cases, the bacterial promoter binds a bacterial RNA polymerase and is at least one promoter selected from the list consisting of araBAD, trp, lac, and Ptac. Sometimes, the nucleic acid fragment comprising promoter sequence comprises a eukaryotic promoter. Optionally, the eukaryotic promoter binds a eukaryotic RNA polymerase and is at least one promoter selected from the list consisting of EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. Alternately or in combination, the eukaryotic promoter is at least one promoter selected from the list consisting of an RNA pol I promoter, an RNA pol II promoter and an RNA pol III promoter. Optionally, the known region of a nucleic acid molecule comprises a repetitive element. In some cases, the repetitive element comprises a mobile insertion element. Sometimes, the repetitive element comprises at least one of a LINE element, a SINE element, an Alu repeat, a transposon, a retrotransposon, a centromeric repeat, and a telomeric repeat. Alternately or in combination, the LINE element comprises SEQ ID NO: 1.

In additional embodiments, there are provided methods of determining a plurality of locus-adjacent sequences of an element in a nucleic acid sample, comprising the steps of a) inserting a nucleic acid comprising a promoter into the element, b) generating a plurality of nucleic acid molecules directed by the promoter, and c) determining the sequence of the plurality of nucleic acid molecules, wherein the nucleic acid molecules are synthesized directly from the nucleic acid sample and wherein the plurality of nucleic acid molecules span locus adjacent sequences. Optionally, the nucleic acid molecules comprise RNA. In some cases, the nucleic acid molecules cannot prime nucleic acid synthesis. Sometimes, the nucleic acid sample comprises cancer cell nucleic acids. In some cases, the nucleic acid sample comprises a single nuclear genome. Often, the nucleic acid sample is obtained from a single cell. Optionally, the method comprises treating the nucleic acid sample using a DNase subsequent to synthesizing the plurality of RNA molecules. Sometimes, the method comprises reverse-transcribing the plurality of RNA molecules. In some cases, the plurality of nucleic acid molecules are RNA molecules. Sometimes, the consensus sequence of the plurality of RNA molecules comprises sequence of molecules synthesized directly from the nucleic acid molecule. In some cases, the attaching comprises inserting the nucleic acid fragment comprising promoter sequence at the known region of the nucleic acid molecule. Optionally, the attaching comprises inserting the nucleic acid fragment comprising promoter sequence at the known region of the nucleic acid molecule. Sometimes, the attaching comprises sequence-specific cleavage of the known region of the nucleic acid molecule. Optionally, the attaching comprises contacting the known region of the nucleic acid molecule to a CRISPR nucleic acid-protein complex. In some cases, the CRISPR nucleic acid-protein complex comprises a guide RNA comprising SEQ ID NO: 3. Sometimes, the attaching comprises ligating the nucleic acid fragment comprising promoter sequence. In some cases, the nucleic acid fragment comprising promoter sequence comprises a viral promoter. A viral promoter is variously at least one promoter selected from the list consisting of T7, T3, T7lac, SP6, pL, CMV, SV40, and CaMV35S. Sometimes, the nucleic acid fragment comprising promoter sequence comprises a bacterial promoter. Optionally, the bacterial promoter is at least one promoter selected from the list consisting of araBAD, trp, lac, and Ptac. In some cases, the nucleic acid fragment comprising promoter sequence comprises a eukaryotic promoter. For example, sometimes the eukaryotic promoter is at least one promoter selected from the list consisting of EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. Optionally, the eukaryotic promoter is at least one promoter selected from the list consisting of an RNA pol I promoter, an RNA pol II promoter and an RNA pol III promoter. Sometimes, the known region of a nucleic acid molecule comprises a repetitive element. Some repetitive element comprises a mobile insertion element. In some cases, the repetitive element comprises at least one of a LINE element, a SINE element, an Alu repeat, a transposon, a retrotransposon, a centromeric repeat, and a telomeric repeat. Optionally, the LINE element comprises SEQ ID NO: 1.

Also provided herein, in some embodiments, are nucleic acid libraries comprising nucleic acids encoding border adjacent sequence for at least 90% of a repeated mobile element's borders in a nucleic acid sample. Sometimes, discrepancies between library constituents and the nucleic acid sample are independently derived. Optionally, at least 50% of said repeated element's borders are present in at least 100 copies. In some cases, library constituents are derived directly from the nucleic acid sample. Alternately or in combination, library components are not clonally amplified prior to sequencing. Optionally, the nucleic acid sample is derived from a single cell. Sometimes, the nucleic acid library is reverse transcribed from an RNA intermediate. In some cases, the nucleic acid library comprises RNA. Optionally, nucleic acid library constituents comprise promoter sequence. Optionally, the RNA promoter sequence comprises at least one of a T7, T3, T7lac, SP6, pL, CMV, SV40, CaMV35S, araBAD, trp, lac, Ptac, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. Optionally, at least one border adjacent sequence indicates a defect in a gene related to at least one of cell cycle regulation, DNA repair, and growth regulation. In some cases, the nucleic acid library comprises nucleic acids encoding border adjacent sequence for at least 95% of a repeated mobile element's borders in a nucleic acid sample. In some cases, the nucleic acid library comprises nucleic acids encoding border adjacent sequence for at least 99% of a repeated mobile element's borders in a nucleic acid sample. Alternately or in combination, at least 50% of the library constituent nucleic acids are located on a nucleic acid within 20 kb of a mobile element border. In some cases, at least 75% of the library constituent nucleic acids are located on a nucleic acid within 20 kb of a mobile element border in proximity to a mobile element border. Optionally, at least 90% of the library constituent nucleic acids are located on a nucleic acid within 20 kb of a mobile element border. Sometimes, at least 50% of the library constituent nucleic acids are located on a nucleic acid within 10 kb of a mobile element border. In some cases, at least 75% of the library constituent nucleic acids are located on a nucleic acid within 10 kb of a mobile element border in proximity to a mobile element border. In some cases, at least 90% of the library constituent nucleic acids are located on a nucleic acid within 10 kb of a mobile element border. Optionally, at least 50% of the library constituent nucleic acids are located on a nucleic acid within 5 kb of a mobile element border. Sometimes, at least 75% of the library constituent nucleic acids are located on a nucleic acid within 5 kb of a mobile element border in proximity to a mobile element border. In some cases, at least 90% of the library constituent nucleic acids are located on a nucleic acid within 5 kb of a mobile element border. Optionally, at least 50% of the library constituent nucleic acids are located on a nucleic acid within 1 kb of a mobile element border. In some cases, at least 75% of the library constituent nucleic acids are located on a nucleic acid within 1 kb of a mobile element border in proximity to a mobile element border. Optionally, at least 90% of the library constituent nucleic acids are located on a nucleic acid within 1kb of a mobile element border. Sometimes, the mean fragment length is about 500 bases. In some cases, the mean fragment length is about 1000 bases. Optionally, the median fragment length is about 500 bases. Optionally, the median fragment length is about 1000 bases.

In further embodiments, there are provided compositions comprising a targeting sequence and a promoter, wherein the targeting sequence comprises a nucleic acid sequence that directs insertion of the composition into one or more specific locations in a nucleic acid sequence and the promoter comprises a nucleic acid sequence that directs synthesis of a nucleic acid from a sample sequence adjacent to the insertion of the promoter. Optionally, the targeting sequence comprises a nucleic acid sequence homologous to the specific location. Sometimes, the targeting sequence comprises a nucleic acid sequence that base pairs to the specific location. In some cases, the targeting sequence comprises a nucleic acid sequence that hybridizes to the specific location. In some cases, the targeting sequence comprises at least one of clustered regularly interspaced short palindromic repeats (CRISPR) sequence, a zinc finger nuclease (ZFN) sequence, and a transcription activator-like effector nucleases (TALENs) sequence. In some cases, the CRISPR sequence comprises a guide RNA with a sequence comprising SEQ ID NO: 3. Often, the promoter comprises at least one of a bacterial promoter, a viral promoter, and a eukaryotic promoter. In some cases, the bacterial promoter comprises at least one of araBAD, trp, lac, and Ptac. Sometimes, the viral promoter comprises at least one of T7, T7lac, SP6, pL, CMV, SV40, and CaMV35S. The eukaryotic promoter often comprises at least one of EFla, PGK1, Ubc, beta actin, CAG, TRE, UAS, Ac5, Polyhedrin, CaMKIIa, ALB, GAL1, GAL10, TEF1, GDS, ADH1, Ubi, H1, and U6. Optionally, the specific location in the nucleic acid sequence comprises a low-complexity nucleic acid sequence. Often, the specific location in the nucleic acid sequence comprises a repetitive nucleic acid sequence. Optionally, the low-complexity nucleic acid sequence or the repetitive nucleic acid sequence comprises at least one of a tri-nucleotide repeat, tandem repeat, and human leukocyte antigen gene. In some cases, the specific location in the nucleic acid sequence comprises a mobile genetic element. Optionally, the mobile genetic element comprises at least one of a transposon, a retrotransposon, a DNA transposon, an insertion sequence, a plasmid, a bacteriophage, a group II intron, a group I intron, an Alu element, a MIR element, an intracisternal A particle (TAP), an ETn, a virus, and a fragments thereof. The retrotransposon often comprises at least one of a transposable element, a LINE, a SINE, and fragments thereof. Optionally, the LINE comprises SEQ ID NO: 1. Alternately or in combination, the virus comprises a retrovirus or a fragment thereof. Sometimes, the nucleic acid synthesis comprises at least one of RNA transcription and DNA synthesis.

Also provided herein are methods of determining a nucleic acid sequence adjacent to a nucleic acid sequence of interest comprising: (a) inserting a targeting nucleic acid sequence comprising a targeting sequence and a promoter into one or more specific locations in the nucleic acid sequence of interest, (b) directing synthesis of a nucleic acid from the promoter, and (c) sequencing the synthesized nucleic acid. Some targeting sequences comprise at least one of a clustered regularly interspaced short palindromic repeats (CRISPR) sequence, a zinc finger nuclease (ZFN) sequence, and a transcription activator-like effector nucleases (TALENs) sequence. Optionally, the CRISPR sequence comprises a guide RNA with a sequence comprising SEQ ID NO: 3. In some cases, the promoter comprises at least one of a bacterial promoter, a viral promoter, and a eukaryotic promoter. Optionally, the bacterial promoter comprises at least one of araBAD, trp, lac, and Ptac. Optionally, the viral promoter comprises at least one of T7, T7lac, SP6, pL, CMV, SV40, and CaMV35S. Optionally, the eukaryotic promoter comprises at least one of EF1a, PGK1, Ubc, beta actin, CAG, TRE, UAS, Ac5, Polyhedrin, CaMKIIa, GAL1, GAL10, TEF1, GDS, ADH1, Ubi, H1, and U6. In some cases, the sequence of interest comprises a low-complexity nucleic acid sequence. The sequence of interest often comprises a repetitive nucleic acid sequence. Optionally, the sequence of interest comprises at least one of tri-nucleotide repeat, tandem repeat, and human leukocyte antigen gene. Alternately or in combination, the sequence of interest comprises a mobile genetic element. Optionally, the mobile genetic element comprises a transposon, a retrotransposon, a DNA transposon, an insertion sequence, a plasmid, a bacteriophage, a group II intron, a group I intron, an Alu element, a MIR element, an intracisternal A particle (IAP), an ETn, a virus, or a fragment thereof. Sometimes, the retrotransposon comprises at least one of transposable element, a LINE, a SINE, and fragments thereof Optionally, the LINE comprises SEQ ID NO: 1. The virus often comprises at least one of a retrovirus and fragments thereof. Optionally, nucleic acid synthesis comprises at least one of RNA transcription and DNA synthesis. In some cases, RNA transcription comprises use of a RNA polymerase. Optionally, the RNA polymerase comprises at least one of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase. In some cases, DNA synthesis comprises use of a DNA polymerase. Optionally, the DNA polymerase comprises at least one of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase. Optionally, the nucleic acid synthesis requires a primer. Often, the synthesized nucleic acid is synthesized directly from the nucleic acid sequence of interest. In some cases, the nucleic acid is synthesized without introducing a mutation. Optionally, the mutation is at least one of a point mutation, a deletion, an insertion, and a chimera. Optionally, the synthesized nucleic acid comprises DNA. In some cases, the synthesized nucleic acid comprises cDNA. Optionally, the synthesized nucleic acid is treated with an RNase. Sometimes, the synthesized nucleic acid is a RNA. Optionally, the synthesized nucleic acid is treated with a DNase. In some cases, the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation. In some cases, the method detects a mutation in a subject. Optionally, the method detects a mutation in a tissue sample obtained from a subject. The tissue sample often comprises at least one of tumor, blood, saliva, sputum, skin, and epithelial tissue.

In additional embodiments provided herein are methods of mapping a site of insertion of a DNA element in a nucleic acid sample from a subject, comprising: i) inserting a targeting nucleic acid sequence comprising a targeting sequence and a promoter by contacting the genomic DNA with the targeting sequence and one or more reagents sufficient to insert the targeting sequence into the DNA element; ii) creating an amplified nucleic acid directly from the genomic DNA by contacting the inserted targeting sequence with one or more enzymes that catalyze nucleic acid synthesis from the promoter thereby creating an amplified nucleic acid; iii) sequencing the amplified nucleic acid. Optionally, the targeting sequence comprises at least one of a clustered regularly interspaced short palindromic repeats (CRISPR) sequence, a zinc finger nuclease (ZFN) sequence, and a transcription activator-like effector nucleases (TALENs) sequence. Sometimes, the CRISPR sequence comprises a guide RNA with a sequence comprising SEQ ID NO: 3. Optionally, the promoter comprises at least one of a bacterial promoter, a viral promoter, and a eukaryotic promoter. In some cases, the bacterial promoter comprises at least one of araBAD, trp, lac, and Ptac. Alternately or in combination, the viral promoter comprises at least one of T7, T7lac, SP6, pL, CMV, SV40, and CaMV35S. Optionally, the eukaryotic promoter comprises at least one of EF1a, PGK1, Ubc, beta actin, CAG, TRE, UAS, Ac5, Polyhedrin, CaMKIIa, GAL1, GAL10, TEF1, GDS, ADH1, Ubi, H1, and U6. Sometimes, the DNA element comprises a low-complexity nucleic acid sequence. In some cases, the DNA element comprises a repetitive nucleic acid sequence. In some cases, the DNA element comprises at least one of a tri-nucleotide repeat, and tandem repeat. Optionally, the DNA element comprises a mobile genetic element. Optionally, the mobile genetic element comprises at least one of a transposon, a retrotransposon, a DNA transposon, an insertion sequence, a plasmid, a bacteriophage, a group II intron, a group I intron, an Alu element, a MIR element, an intracisternal A particle (TAP), an ETn, a virus, and fragments thereof. Optionally, the retrotransposon comprises at least one of a transposable element, a LINE, a SINE, and fragments thereof. Optionally, the LINE comprises SEQ ID NO: 1. Optionally, the virus comprises a retrovirus or a fragment thereof. Sometimes, the enzyme comprises a RNA polymerase. In some cases, the RNA polymerase comprises at least one of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase. Optionally, the enzyme comprises a DNA polymerase. Alternately or in combination, the DNA polymerase comprises at least one of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase. Sometimes, the nucleic acid synthesis requires a primer. Optionally, the synthesized nucleic acid is synthesized directly from the nucleic acid sequence of interest. In some cases, the nucleic acid is synthesized without introducing a mutation. In some cases, is at least one of a point mutation, a deletion, an insertion, and a chimera. Optionally, the synthesized nucleic acid is a DNA. Alternately, the synthesized nucleic acid is a cDNA. Optionally, the synthesized nucleic acid is treated with an RNase. Optionally, the synthesized nucleic acid is a RNA. In some cases, the synthesized nucleic acid is treated with a DNase. Optionally, the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation. Optionally, the method detects a mutation in a subject. Alternately or in combination, the method detects a mutation in a tissue sample obtained from a subject. Optionally, the tissue sample comprises at least one of tumor, blood, saliva, sputum, skin, and epithelial tissue.

Further provided herein are methods of sequencing a repetitive genomic region comprising: i) inserting a targeting nucleic acid sequence comprising a targeting sequence and a promoter by contacting the genomic DNA with the targeting sequence and one or more reagents sufficient to insert the targeting sequence into the repetitive genomic region; ii) creating an amplified nucleic acid directly from the genomic DNA by contacting the inserted targeting sequence with one or more enzymes that catalyze nucleic acid synthesis from the promoter thereby creating an amplified nucleic acid; iii) sequencing the amplified nucleic acid. Optionally, the targeting sequence comprises at least one of a clustered regularly interspaced short palindromic repeats (CRISPR) sequence, a zinc finger nuclease (ZFN) sequence, and a transcription activator-like effector nucleases (TALENs) sequence. Optionally, the CRISPR sequence comprises a guide RNA with a sequence comprising SEQ ID NO: 3. Optionally, the promoter comprises at least one of a bacterial promoter, a viral promoter, and a eukaryotic promoter. Often, the bacterial promoter comprises at least one of araBAD, trp, lac, and Ptac. Optionally, the viral promoter comprises at least one of T7, T7lac, SP6, pL, CMV, SV40, and CaMV35S. The eukaryotic promoter comprises at least one of EF1a, PGK1, Ubc, beta actin, CAG, TRE, UAS, Ac5, Polyhedrin, CaMKIIa, GAL1, GAL10, TEF1, GDS, ADH1, Ubi, H1, and U6. In some cases, the repetitive genomic region comprises a low-complexity nucleic acid sequence. Optionally, the repetitive genomic region comprises a repetitive nucleic acid sequence. In some cases, the repetitive genomic region comprises at least one of a tri-nucleotide repeat and tandem repeat. Sometimes, the repetitive genomic region comprises a mobile genetic element. Optionally, the mobile genetic element comprises at least one of a transposon, a retrotransposon, a DNA transposon, an insertion sequence, a plasmid, a bacteriophage, a group II intron, a group I intron, an Alu element, a MIR element, an intracisternal A particle (TAP), an ETn, a virus, and fragments thereof. In some cases, the retrotransposon comprises at least one of a transposable element, a LINE, a SINE, and fragments thereof. Optionally, the LINE comprises SEQ ID NO: 1. Optionally, the virus comprises a retrovirus or a fragment thereof. Optionally, the enzyme comprises a RNA polymerase. Optionally, the RNA polymerase comprises at least one of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase. Optionally, the enzyme comprises a DNA polymerase. Optionally, the DNA polymerase comprises at least one of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase. In some cases, the nucleic acid synthesis requires a primer. The synthesized nucleic acid is often synthesized directly from the nucleic acid sequence of interest. In some cases, the nucleic acid is synthesized without introducing a mutation. In some cases, the mutation is at least one of a point mutation, a deletion, an insertion, and a chimera. Optionally, the synthesized nucleic acid is a DNA, such as genomic or cDNA. In some cases, the synthesized nucleic acid is treated with an RNase. Optionally, the synthesized nucleic acid is a RNA. In some cases, the synthesized nucleic acid is treated with a DNase. Optionally, the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation. Optionally, the method detects a mutation in a subject. Alternately or in combination, the method detects a mutation in a tissue sample obtained from a subject. Optionally, the tissue sample comprises at least one of tumor, blood, saliva, sputum, skin, and epithelial tissue.

Provided herein are methods of determining a sequence adjacent to a region of known sequence of a nucleic acid molecule. Some such methods comprise a) attaching a hairpin nucleic acid fragment comprising double stranded promoter sequence and an overhanging single stranded portion at the known region of the nucleic acid molecule; b) contacting the nucleic acid fragment to an RNA polymerase directed by the promoter; and c) synthesizing a plurality of RNA molecules; wherein the overhanging single stranded portion basepairs with a reverse complementary portion of the region of known sequence, wherein the two parts of the double stranded promoter sequence region are connected by a single-stranded loop, and wherein a consensus sequence of the plurality of RNA molecules represents the sequence adjacent to the known region of a nucleic acid molecule. Optionally, the consensus sequence is at least 10 kilobases in length. Sometimes, the method comprises treating the nucleic acid molecule using a DNase subsequent to synthesizing the plurality of RNA molecules. Alternately or in combination, the method comprises reverse-transcribing the plurality of RNA molecules. The method sometimes comprises determining nucleic acid sequences of the plurality of RNA molecules. Optionally, the consensus sequence of the plurality of RNA molecules comprises sequence of molecules synthesized directly from the nucleic acid molecule. Alternately or in combination, the attaching comprises inserting the nucleic acid fragment comprising the double stranded promoter sequence at the known region of the nucleic acid molecule. In some cases, the attaching comprises hybridizing the nucleic acid fragment comprising the double stranded promoter sequence at the region of known sequence of the nucleic acid molecule. Optionally, the attaching comprises sequence-specific cleavage of the region of known sequence of the nucleic acid molecule. Alternately or in combination, the attaching comprises contacting the known region of the nucleic acid molecule to a CRISPR nucleic acid-protein complex. Optionally, the CRISPR nucleic acid-protein complex comprises a guide RNA comprising SEQ ID NO: 3. In some cases, the attaching comprises ligating the nucleic acid fragment comprising the double stranded promoter sequence. Sometimes the nucleic acid fragment comprising the double stranded promoter sequence comprises a viral promoter. Optionally, the viral promoter binds a viral RNA polymerase and is at least one promoter selected from the list consisting of T7, T3, T7lac, SP6, pL, CMV, SV40, and CaMV35S. Alternately or in combination, the nucleic acid fragment comprising the double stranded promoter sequence comprises a bacterial promoter. In some cases, the bacterial promoter binds a bacterial RNA polymerase and is at least one promoter selected from the list consisting of araBAD, trp, lac, and Ptac. Sometimes, the nucleic acid fragment comprising the double stranded promoter sequence comprises a eukaryotic promoter. Optionally, the eukaryotic promoter binds a eukaryotic RNA polymerase and is at least one promoter selected from the list consisting of EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. Alternately or in combination, the eukaryotic promoter is at least one promoter selected from the list consisting of an RNA pol I promoter, an RNA pol II promoter and an RNA pol III promoter. Optionally, the known region of a nucleic acid molecule comprises a repetitive element. In some cases, the repetitive element comprises a mobile insertion element. Sometimes, the repetitive element comprises at least one of a LINE element, a SINE element, an Alu repeat, a transposon, a retrotransposon, a centromeric repeat, and a telomeric repeat. Alternately or in combination, the LINE element comprises SEQ ID NO: 1.

In additional embodiments, there are provided methods of determining a plurality of locus-adjacent sequences of an element in a nucleic acid sample, comprising the steps of a) inserting a hairpin nucleic acid comprising a double stranded region constituting a promoter and a single stranded overhanging portion that hybridizes to a reverse complementary portion of the element into the element, and optionally a tether connecting the two segments that form the double-stranded prooter region, such that the entire adapter shares a common phosphodiester backbone, b) generating a plurality of nucleic acid molecules directed by the promoter, and c) determining the sequence of the plurality of nucleic acid molecules, wherein the nucleic acid molecules are synthesized directly from the nucleic acid sample and wherein the plurality of nucleic acid molecules span locus adjacent sequences. Optionally, the nucleic acid molecules comprise RNA. In some cases, the nucleic acid molecules cannot prime nucleic acid synthesis. Sometimes, the nucleic acid sample comprises cancer cell nucleic acids. In some cases, the nucleic acid sample comprises a single nuclear genome. Often, the nucleic acid sample is obtained from a single cell. Optionally, the method comprises treating the nucleic acid sample using a DNase subsequent to synthesizing the plurality of RNA molecules. Sometimes, the method comprises reverse-transcribing the plurality of RNA molecules. In some cases, the plurality of nucleic acid molecules are RNA molecules. Sometimes, the consensus sequence of the plurality of RNA molecules comprises sequence of molecules synthesized directly from the nucleic acid molecule. In some cases, the attaching comprises inserting the nucleic acid fragment comprising a double stranded promoter sequence at the known region of the nucleic acid molecule. Optionally, the attaching comprises hybridizing the nucleic acid fragment comprising double stranded promoter sequence at the known region of the nucleic acid molecule. Sometimes, the attaching comprises sequence-specific cleavage of the known region of the nucleic acid molecule. Optionally, the attaching comprises contacting the known region of the nucleic acid molecule to a CRISPR nucleic acid-protein complex. In some cases, the CRISPR nucleic acid-protein complex comprises a guide RNA comprising SEQ ID NO: 3. Sometimes, the attaching comprises ligating the nucleic acid fragment comprising the double stranded promoter sequence. In some cases, the nucleic acid fragment comprising the double stranded promoter sequence comprises a viral promoter. A viral promoter is variously at least one promoter selected from the list consisting of T7, T3, T7lac, SP6, pL, CMV, SV40, and CaMV35S. Sometimes, the nucleic acid fragment comprising the double stranded promoter sequence comprises a bacterial promoter. Optionally, the bacterial promoter is at least one promoter selected from the list consisting of araBAD, trp, lac, and Ptac. In some cases, the nucleic acid fragment comprising the double stranded promoter sequence comprises a eukaryotic promoter. For example, sometimes the eukaryotic promoter is at least one promoter selected from the list consisting of EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. Optionally, the eukaryotic promoter is at least one promoter selected from the list consisting of an RNA pol I promoter, an RNA polII promoter and an RNA polIII promoter. Sometimes, the known region of a nucleic acid molecule comprises a repetitive element. Some repetitive element comprises a mobile insertion element. In some cases, the repetitive element comprises at least one of a LINE element, a SINE element, an Alu repeat, a transposon, a retrotransposon, a centromeric repeat, and a telomeric repeat. Optionally, the LINE element comprises SEQ ID NO: 1.

Also provided herein, in some embodiments, are nucleic acid libraries comprising hairpin nucleic acids encoding border adjacent sequence for at least 90% of a repeated mobile element's borders in a nucleic acid sample, and encoding a double stranded promoter sequence. Sometimes, discrepancies between library constituents and the nucleic acid sample are independently derived. Optionally, at least 50% of said repeated element's borders are present in at least 100 copies. In some cases, library constituents are derived directly from the nucleic acid sample. Alternately or in combination, library components are not clonally amplified prior to sequencing. Optionally, the nucleic acid sample is derived from a single cell. Sometimes, the nucleic acid library is reverse transcribed from an RNA intermediate. In some cases, the nucleic acid library comprises RNA. Optionally, the double stranded promoter sequence comprises at least one of a bacterial promoter, a viral promoter, and a eukaryotic promoter. Optionally, the promoter sequence comprises at least one of a T7, T3, T7lac, SP6, pL, CMV, SV40, CaMV35S, araBAD, trp, lac, Ptac, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. Optionally, at least one border adjacent sequence indicates a defect in a gene related to at least one of cell cycle regulation, DNA repair, and growth regulation. In some cases, the nucleic acid library comprises nucleic acids encoding border adjacent sequence for at least 95% of a repeated mobile element's borders in a nucleic acid sample. In some cases, the nucleic acid library comprises nucleic acids encoding border adjacent sequence for at least 99% of a repeated mobile element's borders in a nucleic acid sample. Alternately or in combination, at least 50% of the library constituent nucleic acids are located on a nucleic acid within 20 kb of a mobile element border. In some cases, at least 75% of the library constituent nucleic acids are located on a nucleic acid within 20 kb of a mobile element border in proximity to a mobile element border. Optionally, at least 90% of the library constituent nucleic acids are located on a nucleic acid within 20 kb of a mobile element border. Sometimes, at least 50% of the library constituent nucleic acids are located on a nucleic acid within 10 kb of a mobile element border. In some cases, at least 75% of the library constituent nucleic acids are located on a nucleic acid within 10 kb of a mobile element border in proximity to a mobile element border. In some cases, at least 90% of the library constituent nucleic acids are located on a nucleic acid within 10 kb of a mobile element border. Optionally, at least 50% of the library constituent nucleic acids are located on a nucleic acid within 5 kb of a mobile element border. Sometimes, at least 75% of the library constituent nucleic acids are located on a nucleic acid within 5 kb of a mobile element border in proximity to a mobile element border. In some cases, at least 90% of the library constituent nucleic acids are located on a nucleic acid within 5 kb of a mobile element border. Optionally, at least 50% of the library constituent nucleic acids are located on a nucleic acid within 1 kb of a mobile element border. In some cases, at least 75% of the library constituent nucleic acids are located on a nucleic acid within 1 kb of a mobile element border in proximity to a mobile element border. Optionally, at least 90% of the library constituent nucleic acids are located on a nucleic acid within 1 kb of a mobile element border. Sometimes, the mean fragment length is about 500 bases. In some cases, the mean fragment length is about 1000 bases. Optionally, the median fragment length is about 500 bases. Optionally, the median fragment length is about 1000 bases.

In further embodiments, there are provided compositions comprising a hairpin polynucleotide comprising a single stranded targeting sequence and a double stranded promoter region formed by reverse-complementarity among segments of the hairpin, wherein the targeting sequence comprises a single stranded nucleic acid sequence that binds to a reverse complementary single stranded nucleic acid sequence at one or more specific locations in a nucleic acid sequence and the double stranded promoter comprises a nucleic acid sequence and its reverse complement that anneal together to from a double-stranded region that directs synthesis of a nucleic acid from a sample sequence adjacent to the insertion of the promoter. Optionally, the single stranded targeting sequence comprises a single stranded nucleic acid sequence reverse complementary to the specific location. Sometimes, the single stranded targeting sequence comprises a single stranded nucleic acid sequence that base pairs to the single stranded sequence at the specific location. In some cases, the single stranded targeting sequence comprises a nucleic acid sequence that hybridizes to the specific location. In some cases, the targeting sequence comprises at least one of clustered regularly interspaced short palindromic repeats (CRISPR) sequence, a zinc finger nuclease (ZFN) sequence, and a transcription activator-like effector nucleases (TAL-ENs) sequence. In some cases, the CRISPR sequence comprises a guide RNA with a sequence comprising SEQ ID NO: 3. Often, the double stranded promoter comprises at least one of a bacterial promoter, a viral promoter, and a eukaryotic promoter. In some cases, the bacterial promoter comprises at least one of araBAD, trp, lac, and Ptac. Sometimes, the viral promoter comprises at least one of T7, T7lac, SP6, pL, CMV, SV40, and CaMV35S. The eukaryotic promoter often comprises at least one of EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. Optionally, the specific location in the nucleic acid sequence comprises a low-complexity nucleic acid sequence. Often, the specific location in the nucleic acid sequence comprises a repetitive nucleic acid sequence. Optionally, the low-complexity nucleic acid sequence or the repetitive nucleic acid sequence comprises at least one of a tri-nucleotide repeat, tandem repeat, and human leukocyte antigen gene. In some cases, the specific location in the nucleic acid sequence comprises a mobile genetic element. Optionally, the mobile genetic element comprises at least one of a transposon, a retrotransposon, a DNA transposon, an insertion sequence, a plasmid, a bacteriophage, a group II intron, a group I intron, an Alu element, a MIR element, an intracisternal A particle (IAP), an ETn, a virus, and a fragments thereof. The retrotransposon often comprises at least one of a transposable element, a LINE, a SINE, and fragments thereof. Optionally, the LINE comprises SEQ ID NO: 1. Alternately or in combination, the virus comprises a retrovirus or a fragment thereof. Sometimes, the nucleic acid synthesis comprises at least one of RNA transcription and DNA synthesis.

Also provided herein are methods of determining a nucleic acid sequence adjacent to a nucleic acid sequence of interest comprising: (a) inserting a hairpin polynucleotide comprising a single stranded targeting sequence and a double stranded promoter into one or more specific locations in the nucleic acid sequence of interest, (b) directing synthesis of a nucleic acid from the promoter, and (c) sequencing the synthesized nucleic acid. Some targeting sequences comprise at least one of a clustered regularly interspaced short palindromic repeats (CRISPR) sequence, a zinc finger nuclease (ZFN) sequence, and a transcription activator-like effector nucleases (TALENs) sequence. Optionally, the CRISPR sequence comprises a guide RNA with a sequence comprising SEQ ID NO: 3. In some cases, the promoter comprises at least one of a bacterial promoter, a viral promoter, and a eukaryotic promoter. Optionally, the bacterial promoter comprises at least one of araBAD, trp, lac, and Ptac. Optionally, the viral promoter comprises at least one of T7, T7lac, SP6, pL, CMV, SV40, and CaMV35S. Optionally, the eukaryotic promoter comprises at least one of EF1a, PGK1, Ubc, beta actin, CAG, TRE, UAS, Ac5, Polyhedrin, CaMKIIa, GAL1, GAL10, TEF1, GDS, ADH1, Ubi, H1, and U6. In some cases, the sequence of interest comprises a low-complexity nucleic acid sequence. The sequence of interest often comprises a repetitive nucleic acid sequence. Optionally, the sequence of interest comprises at least one of tri-nucleotide repeat, tandem repeat, and human leukocyte antigen gene. Alternately or in combination, the sequence of interest comprises a mobile genetic element. Optionally, the mobile genetic element comprises a transposon, a retrotransposon, a DNA transposon, an insertion sequence, a plasmid, a bacteriophage, a group II intron, a group I intron, an Alu element, a MIR element, an intracisternal A particle (TAP), an ETn, a virus, or a fragment thereof Sometimes, the retrotransposon comprises at least one of transposable element, a LINE, a SINE, and fragments thereof. Optionally, the LINE comprises SEQ ID NO: 1. The virus often comprises at least one of a retrovirus and fragments thereof. Optionally, nucleic acid synthesis comprises at least one of RNA transcription and DNA synthesis. In some cases, RNA transcription comprises use of a RNA polymerase. Optionally, the RNA polymerase comprises at least one of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase. In some cases, DNA synthesis comprises use of a DNA polymerase. Optionally, the DNA polymerase comprises at least one of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase. Optionally, the nucleic acid synthesis requires a primer. Often, the synthesized nucleic acid is synthesized directly from the nucleic acid sequence of interest. In some cases, the nucleic acid is synthesized without introducing a mutation. Optionally, the mutation is at least one of a point mutation, a deletion, an insertion, and a chimera. Optionally, the synthesized nucleic acid comprises DNA. In some cases, the synthesized nucleic acid comprises cDNA. Optionally, the synthesized nucleic acid is treated with an RNase. Sometimes, the synthesized nucleic acid is a RNA. Optionally, the synthesized nucleic acid is treated with a DNase. In some cases, the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation. In some cases, the method detects a mutation in a subject. Optionally, the method detects a mutation in a tissue sample obtained from a subject. The tissue sample often comprises at least one of tumor, blood, saliva, sputum, skin, and epithelial tissue.

In additional embodiments provided herein are methods of mapping a site of insertion of a DNA element in a nucleic acid sample from a subject, comprising: i) inserting a hairpin polynucleotide comprising a single stranded targeting sequence region and a double stranded promoter region formed by base-pairing of a promoter segment and its reverse complement in the hairpin, by contacting the genomic DNA with the targeting sequence and one or more reagents sufficient to insert the targeting sequence into the DNA element; ii) creating an amplified nucleic acid directly from the genomic DNA by contacting the inserted targeting sequence with one or more enzymes that catalyze nucleic acid synthesis from the double stranded promoter thereby creating an amplified nucleic acid; iii) sequencing the amplified nucleic acid. Optionally, the targeting sequence comprises at least one of a clustered regularly interspaced short palindromic repeats (CRISPR) sequence, a zinc finger nuclease (ZFN) sequence, and a transcription activator-like effector nucleases (TALENs) sequence. Sometimes, the CRISPR sequence comprises a guide RNA with a sequence comprising SEQ ID NO: 3. Optionally, the double stranded promoter comprises at least one of a bacterial promoter, a viral promoter, and a eukaryotic promoter. In some cases, the bacterial promoter comprises at least one of araBAD, trp, lac, and Ptac. Alternately or in combination, the viral promoter comprises at least one of T7, T7lac, SP6, pL, CMV, SV40, and CaMV35S. Optionally, the eukaryotic promoter comprises at least one of EF1a, PGK1, Ubc, beta actin, CAG, TRE, UAS, Ac5, Polyhedrin, CaMKIIa, GAL1, GAL10, TEF1, GDS, ADH1, Ubi, H1, and U6. Sometimes, the DNA element comprises a low-complexity nucleic acid sequence. In some cases, the DNA element comprises a repetitive nucleic acid sequence. In some cases, the DNA element comprises at least one of a tri-nucleotide repeat, and tandem repeat. Optionally, the DNA element comprises a mobile genetic element. Optionally, the mobile genetic element comprises at least one of a transposon, a retrotransposon, a DNA transposon, an insertion sequence, a plasmid, a bacteriophage, a group II intron, a group I intron, an Alu element, a MIR element, an intracisternal A particle (TAP), an ETn, a virus, and fragments thereof. Optionally, the retrotransposon comprises at least one of a transposable element, a LINE, a SINE, and fragments thereof. Optionally, the LINE comprises SEQ ID NO: 1. Optionally, the virus comprises a retrovirus or a fragment thereof Sometimes, the enzyme comprises a RNA polymerase. In some cases, the RNA polymerase comprises at least one of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase. Optionally, the enzyme comprises a DNA polymerase. Alternately or in combination, the DNA polymerase comprises at least one of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase. Sometimes, the nucleic acid synthesis requires a primer. Optionally, the synthesized nucleic acid is synthesized directly from the nucleic acid sequence of interest. In some cases, the nucleic acid is synthesized without introducing a mutation. In some cases, is at least one of a point mutation, a deletion, an insertion, and a chimera. Optionally, the synthesized nucleic acid is a DNA. Alternately, the synthesized nucleic acid is a cDNA. Optionally, the synthesized nucleic acid is treated with an RNase. Optionally, the synthesized nucleic acid is a RNA. In some cases, the synthesized nucleic acid is treated with a DNase. Optionally, the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation. Optionally, the method detects a mutation in a subject. Alternately or in combination, the method detects a mutation in a tissue sample obtained from a subject. Optionally, the tissue sample comprises at least one of tumor, blood, saliva, sputum, skin, and epithelial tissue.

Further provided herein are methods of sequencing a repetitive genomic region comprising: i) inserting a hairpin targeting nucleic acid sequence comprising a single stranded targeting sequence region and a double stranded promoter region formed by base-pairing of a promoter region and its reverse-complement, optionally connected by a single stranded hairpin region in the hairpin, by contacting the genomic DNA with the targeting sequence and one or more reagents sufficient to insert the single stranded targeting sequence into a reverse complementary sequence at the repetitive genomic region; ii) creating an amplified nucleic acid directly from the genomic DNA by contacting the inserted targeting sequence with one or more enzymes that catalyze nucleic acid synthesis from the double stranded promoter thereby creating an amplified nucleic acid; iii) sequencing the amplified nucleic acid. Optionally, the targeting sequence comprises at least one of a clustered regularly interspaced short palindromic repeats (CRISPR) sequence, a zinc finger nuclease (ZFN) sequence, and a transcription activator-like effector nucleases (TALENs) sequence. Optionally, the CRISPR sequence comprises a guide RNA with a sequence comprising SEQ ID NO: 3. Optionally, the double stranded promoter comprises at least one of a bacterial promoter, a viral promoter, and a eukaryotic promoter. Often, the bacterial promoter comprises at least one of araBAD, trp, lac, and Ptac. Optionally, the viral promoter comprises at least one of T7, T7lac, SP6, pL, CMV, SV40, and CaMV35S. The eukaryotic promoter comprises at least one of EF1a, PGK1, Ubc, beta actin, CAG, TRE, UAS, Ac5, Polyhedrin, CaMKIIa, GAL1, GAL10, TEF1, GDS, ADH1, Ubi, H1, and U6. In some cases, the repetitive genomic region comprises a low-complexity nucleic acid sequence. Optionally, the repetitive genomic region comprises a repetitive nucleic acid sequence. In some cases, the repetitive genomic region comprises at least one of a tri-nucleotide repeat and tandem repeat. Sometimes, the repetitive genomic region comprises a mobile genetic element. Optionally, the mobile genetic element comprises at least one of a transposon, a retrotransposon, a DNA transposon, an insertion sequence, a plasmid, a bacteriophage, a group II intron, a group I intron, an Alu element, a MIR element, an intracisternal A particle (TAP), an ETn, a virus, and fragments thereof. In some cases, the retrotransposon comprises at least one of a transposable element, a LINE, a SINE, and fragments thereof. Optionally, the LINE comprises SEQ ID NO: 1. Optionally, the virus comprises a retrovirus or a fragment thereof Optionally, the enzyme comprises a RNA polymerase. Optionally, the RNA polymerase comprises at least one of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase. Optionally, the enzyme comprises a DNA polymerase. Optionally, the DNA polymerase comprises at least one of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase. In some cases, the nucleic acid synthesis requires a primer. The synthesized nucleic acid is often synthesized directly from the nucleic acid sequence of interest. In some cases, the nucleic acid is synthesized without introducing a mutation. In some cases, the mutation is at least one of a point mutation, a deletion, an insertion, and a chimera. Optionally, the synthesized nucleic acid is a DNA, such as genomic or cDNA. In some cases, the synthesized nucleic acid is treated with an RNase. Optionally, the synthesized nucleic acid is a RNA. In some cases, the synthesized nucleic acid is treated with a DNase. Optionally, the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation. Optionally, the method detects a mutation in a subject. Alternately or in combination, the method detects a mutation in a tissue sample obtained from a subject. Optionally, the tissue sample comprises at least one of tumor, blood, saliva, sputum, skin, and epithelial tissue.

BRIEF DESCRIPTION OF THE DRAWINGS

Reference is made to the following detailed description that sets forth illustrative embodiments, in which the principles of the invention are utilized, and the accompanying drawings of which:

Figure 1:
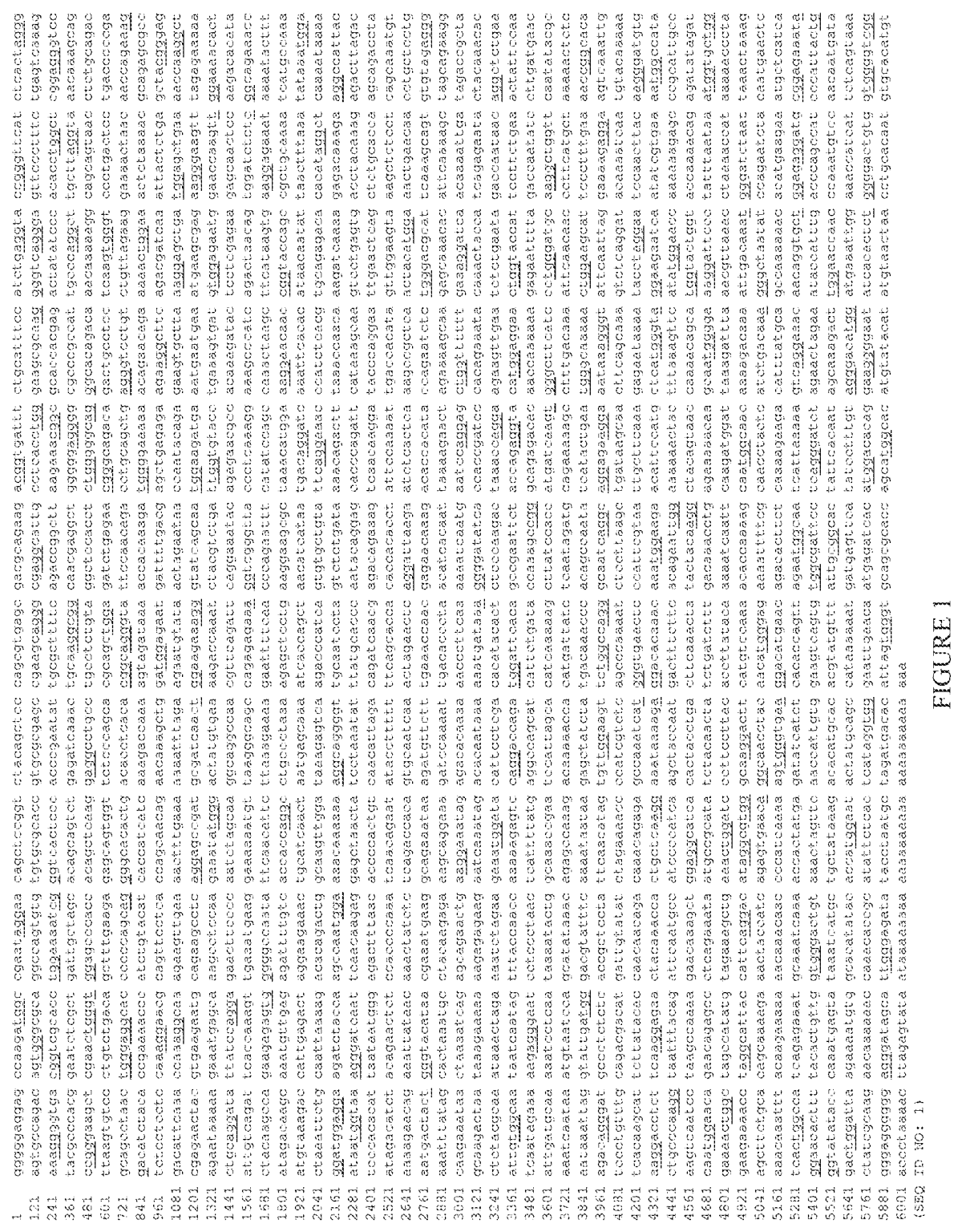

FIG. 1 shows an exemplary human LINE1 (L1.4) repetitive element DNA sequence (SEQ ID NO: 1).

FIG. 2 shows an exemplary consensus sequence of L1HA: Diagnostic sequence at 3' end of LINE-1 element (SEQ ID NO: 2).

FIG. 3 shows an exemplary guide RNA sequence (SEQ ID NO: 3).

FIG. 4 shows an exemplary Alu-Y sequence (SEQ ID NO:4).

FIG. 5 shows CRISPR induced insertion of target specific T7 promoter sequences.

FIG. 12 shows CRISPR induced insertion of a hairpin nucleic acid with a double stranded T7 promoter to a target locus and subsequent linear amplification of the target locus.

DETAILED DESCRIPTION

Figure 6:
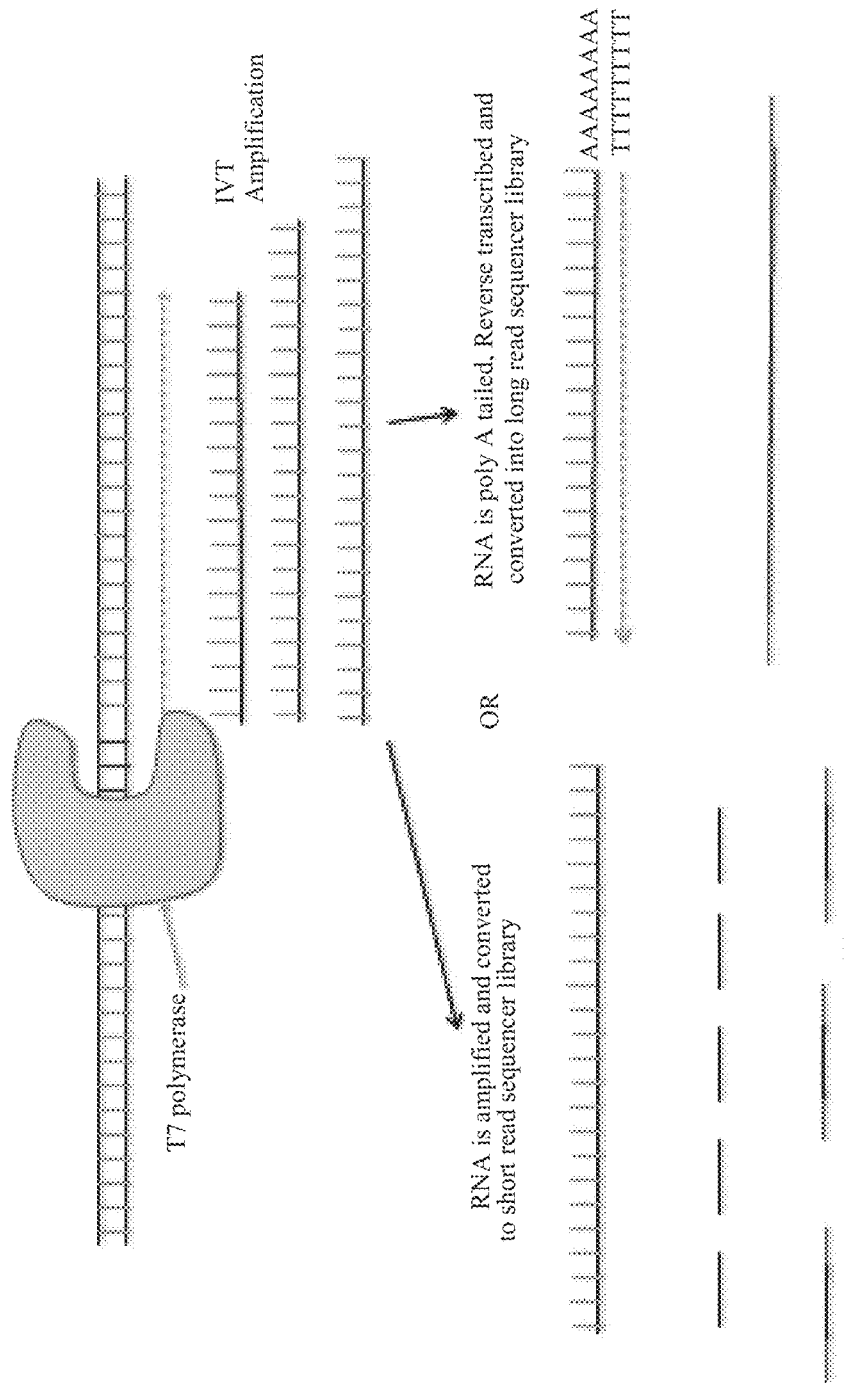
FIG. 6 shows in vitro transcription of target DNA generating amplified RNA copies of the target template.

Methods disclosed herein involve nucleic acid editing technology (CRISPR, TALENS, Zinc figure, transposase, and other methods known by one of skill in the art) to insert a promoter such as a bacterial or bacteriophage promoter (such as T7, T3, or SP6) including double stranded promoters, though a wide range of promoters are compatible with the disclosure herein and the list herein is not intended to be exhaustive) capable of DNA directed RNA transcription. Alternately, archaeal or eukaryotic promoters are also contemplated in some cases. Following transcription of RNA molecules from the inserted promoter or double stranded promoter, there is an effective linear amplification of the adjacent sequence, in the form of a population of RNA molecules derived directly from the sample as template. The RNA molecules are converted by any number of methods into either short read or long read DNA sequencing libraries.

Using CRISPR as an illustrative embodiment, the methods comprise a first design of a sequence specific guide RNA molecule that targets a conserved and locally unique sequence upstream of a sequence of interest. Preferably, the specific guide RNA molecule binds to a nucleic acid sequence that is unique to a repeat element, and may occur multiple times in the sample such as a genomic sample but in which each occurrence corresponds to an occurrence of the repeat element. Optionally, the specific guide RNA molecule binds to a nucleic acid sequence that is unique to a specific genomic region to be sequenced. The sequence specific molecule is added to a mixture of high molecular weight sample DNA, the CRISPR/CAS system components (when using CRISPR technology) and a donor DNA molecule containing the T7 promoter sequence. The CRISPR/CAS system components create a double stranded break having an overhanging single stranded portion which can be connected to a hairpin donor DNA molecule containing the double stranded T7 promoter sequence connected by a loop to a single stranded portion having reverse complementarity hybridizes to the overhand in the double stranded break. In some cases the CRISPR/CAS molecule is assembled with its associated nucleic acids prior to contacting to the sample. In addition, the CRISPR/CAS system, in some cases is utilized to introduce the single stranded or double stranded T7 promoter via end joining in a single step. In some cases, the T7 promoter is introduced in a cell. Alternatively, the T7 promoter is introduced in vitro. In further cases, a molecular barcode is introduced with the T7 promoter.

After insertion of the RNA promoter or double stranded RNA promoter such as T7 promoter by CAS into the specific genomic locus, a compatible RNA polymerase such as T7 polymerase is added to the sample along with the requisite ribonucleotides and buffers. In vitro transcription is used to generate an approximate 1,000-fold amplification of target DNA sequences through the RNA intermediate. RNA generated from the in vitro transcription is then used as a template for DNA library generation, such as by fragmentation by synthesis, and conversion into short read sequence libraries. Alternatively, the RNA generated from the in vitro transcription reaction is poly-A tailed or polyadenylated and subsequently reverse transcribed using an oligo dT primer and reverse transcriptase to generate full length reverse transcribed DNA copies of the RNA templates. Adapters are optionally ligated on at this step for subsequent sequencing of full length reverse transcribed DNA molecules using single molecule sequencing technology.

The purpose of some of the methods described herein is to generate long targeted templates suitable for long read sequencing. High molecular weight sample DNA, such as genomic DNA, is first obtained from a source (blood, serum, cells, cell culture, saliva, tumor, hair, skin, epithelial tissue, urine, stool, amniotic fluid, sputum, cerebrospinal fluid, mucus, for example). Standard DNA purification techniques are optionally used for the isolation of high molecular weight sample DNA. The subsequent reactions often occur outside of a cell, though in some embodiments, cellular material may remain in the reaction chamber. Intact cells are not used in the reaction in many embodiments compatible. Alternatively, the targeted template is in the genome of an intact cell. Sample DNA with the methods herein is obtained from any organism. Alternatively, sample DNA is synthetic. Methods for preparing high molecular weight sample DNA are routine and known in the art. In some cases, the sample DNA comprises genomic DNA. Sample DNA comprising genomic DNA is optionally selected from a eukaryotic genome, a prokaryotic genome, a eubacterial genome, an archaea genome, a viral genome, or a synthetic nucleic acid source. In some cases, the sample is a tumor cell or a circulating cancer cell. Alternatively, the sample DNA comprises cell free DNA, plasmid DNA, viral DNA, synthetic DNA, or other high molecular weight DNA samples obtained from a subject.

A guide RNA is designed with a target specific motif in some approaches. The target may be adjacent to or within a gene of interest, adjacent to or within a promoter of interest or within a gene, exon, intron or intergenic region. Guide RNAs use sequences having reverse complementarity to a sample within their sequence to bind to a sample DNA may be complete or incomplete reverse complementarity. Guide RNA may be designed to target multiple positions within the target sequence or flanking the target sequence with insertion of a nucleic acid encoding a donor sequence at any one of either ends of the target sequence and in either or both orientations for insertion of a donor sequence. Guide RNA design is upstream of a photospacer adjacent motif or PAM sequence comprising of NGG nucleotide sequence. Some CAS9 mutants eliminate the need for PAM sequence flanking the target sequence of the guide RNA molecule, and in some cases herein the PAM sequence is absent. Single guide RNAs are used. Alternately, multiple guide RNAs are designed and used simultaneously in a single reaction. In exemplary embodiments guide RNA target sequences are designed at intervals across a target sequence. Guide RNAs are designed to be in opposite orientations along the double stranded target DNA molecule. Optionally guide RNAs are designed to be on opposing strands of the double stranded target DNA molecule. The method may insert a multitude of T7 donor sequences or hairpin double stranded T7 donor sequences into the target genomic DNA loci of interest.

The donor sequence or hairpin donor sequence comprises an amplification site, such as a single stranded or a double stranded amplification site, in some cases specifically a single stranded or double stranded promoter site for T7 polymerase. T3 polymerase and SP6 promoter sequences are alternative donor sequences, as are others available to one of skill in the art. Alternatively, other DNA dependent RNA polymerase promoters are used. In an exemplary embodiment, a T7 promoter is used. A suitable T7 promoter sequence is 5'-TAATACGACTCACTATAG-3' (SEQ ID NO: 5) and T7 transcription starts from the 3' G. RNA transcription occurs 5'-3' generating an RNA molecule also in the 5'-3' orientation, making it a useful template for reverse transcription and conversion into cDNA. RNA polymerases have an extremely low error rate at $0.5 \times 10^{\wedge}-4$ or one misincorporation for every 10-30 kb transcript. RNA copies are generated only from the double stranded template DNA molecule. RNA polymerase fragment lengths range from a few hundred base pairs to multiple kilobases and reported for transcript lengths up to 30 kilobases (T7 ribomax, Promega). Magnesium is needed in the buffer for RNA polymerase amplification.

Incubation times vary according to the promoter and polymerase used. Using T7 polymerase, incubation times range from a few minutes to 2 hours. Longer incubation times typically result in better yields and overall performance. RNA resulting from the in vitro transcription reaction is purified or separated from the DNA sample optionally through DNA degradation using a DNAse or an endonuclease.

Alternatively, the DNA sample is left undegraded. Optionally, RNA fragments are size selected. Downstream processing of RNA templates generated from the in vitro transcription reaction are optionally fragmented, for example though gentle magnesium treatment, physical or enzymatic means. Short RNA fragments are optionally converted to sequencer libraries through standard small RNA library preparation techniques. Alternatively, long RNA molecules are poly-adenylated through poly-A polymerase. Polyadenylated long RNA molecules are reverse transcribed through standard techniques known in the art. Reverse transcriptase enzymes such as SuperScript™, in combination with oligo (d)T primers, are capable of efficiently generating full length cDNA from long polyA tailed RNA molecules. RNA are optionally removed from the reverse transcribed DNA output through digestion of RNA. Single stranded full length reverse transcribed DNA molecules may then be converted to long read sequencer libraries through standard adapter ligation.

Variations at multiple steps in the reaction consistent with the disclosure herein are contemplated. In some variants, donor DNA molecules in the CRISPR/CAS reaction optionally include (in addition to the T7 promoter sequence) a primer site for second strand cDNA synthesis. In these embodiments, the guide RNA plus CRISPR/CAS system makes a double stranded cut at the target site upstream of the PAM sequence. The donor DNA molecule then includes a T7 promoter with a universal primer site downstream. In additional variants, donor DNA molecules in the CRISPR/CAS reaction optionally include (in addition to the T7 promoter sequence) a primer site for second strand cDNA synthesis. In these embodiments, the guide RNA plus CRISPR/CAS system makes a double stranded cut having sticky ends or a single stranded overhang at the target site upstream of the PAM sequence. The hairpin donor DNA molecule then includes a double stranded T7 promoter with a universal primer site downstream, wherein the two segments of the double-stranded region are connected by a loop, and the double-stranded region is connected through one of its segments to the single stranded overhang at the target site. For example, in some instances, the universal primer sequence is a sequencing primer compliment for the sequencer platform of choice. The construct of the donor molecule in the CRISPR/CAS reaction is or comprises 5'-T7 promoter-universal primer sequence-3'. In vitro transcription with T7 polymerase starts at the 3' G of the T7 promoter sequence and transcribe the universal primer sequence downstream and through the target DNA sequence. After polyA addition, oligo (d)T primed reverse transcription will transcribe through the universal primer sequence when creating the first strand cDNA. Second strand cDNA synthesis is achieved by primer extension using reverse compliment primers for the universal primer sequence. The final construct of the cDNA molecule entering NGS library conversion would therefore be 5'-universal primer-target DNA-polyA-3'.

In alternative methods contemplated herein, the CRISPR/CAS system makes a double stranded cut at the target site. The double stranded cut is treated with an exonuclease which creates a sticky end of single stranded DNA at the cut site to which an adapter or a hairpin adaptor having complementary sequence and a single stranded or double stranded transcription promoter anneals. The annealed adaptor is ligated to the sample DNA, creating a promoter-target DNA hybrid, or a double stranded promoter-target DNA hybrid ready for in vitro transcription of the sample DNA. In this alternative method, two levels of specificity are introduced both at the CRISPR/CAS sequence specific targeted double stranded DNA cleavage and at the annealing of the adaptor at the exonuclease created sticky end. Optionally, the adaptor is a hairpin comprising a portion which folds onto itself and a second portion which has a sequence complementary to a targeted sequence. Hairpin adaptors may have advantages such as improved ligation efficiency and kinetics.

Addition of a molecular barcode upstream of the single stranded or double stranded T7 promoter sequence (and the optional universal primer sequence) in the donor DNA molecule is employed in some cases. The construct of the donor DNA sequence in this example is 5'-T7 promoter-universal primer-N-mer-3'. In some cases, PCR amplification is required to increase the amount of material for sequencer library generation and the addition of the molecular barcode enables the identification of unique molecules from clonally amplified long PCR products. For single cell applications using massively parallel compartmentalization through microdroplet or microfluidic technologies, the molecular barcode is optionally replaced by a compartment specific barcode. This allows for bulk processing of all cells in the sample post CRISPR/CAS target insertion and allows for the unique identification of sequenced molecules from a given single cell.

Approaches presented herein often allow the targeted amplification of a plurality of repeat-adjacent nucleic acid sequences. Thus, one is enabled to determine, for example, the global distribution of insertion sites throughout a nucleic acid sample such as a genome. In particular, by selecting a genomic mobile element, one determines a plurality or regions where the mobile element is inserted, up to and including 10%, 20%, 30%, 40%, 50%, 60%, 70%, 80%, 90%, 95%, 99%, or even 100% of the total number of insertion sites for a repetitive element of interest in a genome. In some cases a portion of these insertion sites are amplified 10×, 100×, 1000×, 10000×, 100000×, 1000000× or greater. This fraction amplified to this level comprises up to and including 10%, 20%, 30%, 40%, 50%, 60%, 70%, 80%, 90%, 95%, 99%, or even 100% of the total number of insertion sites in some cases.

Thus, through practice of the methods and use of the compositions disclosed herein, one is able to determine the global insertion pattern for a mobile repeat element throughout the entire genome of a cell or cell population of interest, such as a cancer cell or cancer cell population. Furthermore, through the high level of amplification achieved, one is able to study single cells or very small cell populations. Finally, because the amplification is in many cases linear amplification directly generated from the sample template, rather than a product of exponential amplification using PCR, the amplification is accomplished without any concomitant proliferation of errors such as point mutations or translocations that occur pursuant to the library generation process. Errors may occur, but are easily recognized as they are very likely to be unique to a single product. Furthermore, because the amplification occurs through an RNA intermediate, there is no risk of a synthesized product annealing to the sample or another amplified product and priming further extension, a phenomenon which is difficult to distinguish from a translocation event in the sample itself.

Methods and use of the compositions disclosed herein allow one to determine the sequence at any targeted site in the genome, including repetitive elements as well as average complexity DNA sequences, for example mRNA coding sequences. Accordingly, methods herein are not limited to sequencing repetitive and low-complexity genomic regions but can be applied to any desired location in the genome.

As a result of practice of methods disclosed herein, one obtains a library that is both highly amplified, highly representative of the total distribution sites for a mobile element, and highly resistant to error propagation in the synthesis process.

Methods, compositions and kits are provided for producing multi-insert nucleic acids. These methods, compositions and kits find use in a number of applications, such as whole-genome sequencing. These and other objects, advantages, and features of the invention will become apparent to those persons skilled in the art upon reading the details of the compositions and methods as more fully described below.

Targeted Insertion of Tags

Disclosed herein are methods of obtaining sequences from a desired genomic location by inserting a tag, such as a hairpin tag, into the desired genomic location. In some cases, tags are inserted into the desired genomic location using gene targeting technology, for example CRISPR, TALENS, Zinc figure, transposase, and other methods known by one of skill in the art. The tag or hairpin tag is designed to contain a sequence that allows amplification from the desired genomic location. The tag or hairpin tag is chosen depending on the desired method of amplification. In some cases, the desired genomic location is amplified by transcription. If the desired genomic location is amplified by transcription, the tag is designed to contain a promoter sequence, for example a bacteriophage promoter such as T7, T3, SP6, or other bacteriophage promoter. Alternatively, the hairpin tag is designed to contain a double stranded promoter sequence, for example a bacteriophage promoter such as T7, T3, SP6, or other bacteriophage promoter. The promoter sequence or double stranded promoter sequence, in some cases, is a viral promoter such as pL, CMV, SV40, CaMV35S, or other viral promoter. In some cases, it is desirable to use a mammalian promoter sequence such as EF1a, PGK1, Ubc, beta actin, CAG, TRE, UAS, Ac5, Polyhedrin, CaMKIIa, ALB, GAL1, GAL10, TEF1, GDS, ADH1, Ubi, H1, U6, or other mammalian promoter. In some cases, the promoter is a RNA polymerase I promoter. In some cases, the promoter is a RNA polymerase II promoter. In some cases, the promoter is a RNA polymerase III promoter. In some cases, the promoter is a RNA polymerase IV promoter. In some cases the promoter is a RNA polymerase V promoter. In some cases, the promoter is a single subunit RNA polymerase promoter.

Tags, including hairpin tags, comprising CRISPR targeting sequences include but are not limited to the group consisting of ACTAGAAAATCTAGAAGAAA (SEQ ID NO: 5), TTGTAGTATAGTTTGAAGTC (SEQ ID NO: 6), AAAACCCTAGAAGAAAACCT (SEQ ID NO: 7), TCTTTAAGAATGTTGAATAT (SEQ ID NO: 8), ACAGCCAATATCATACTGAA (SEQ ID NO: 9), TCACATAGTCCCATATTTCT (SEQ ID NO: 10), CTACAGTAACCAAAACAGCA (SEQ ID NO: 11), AGCAACTTCAGCAAAGTCTC (SEQ ID NO: 12), TGACTTCAAACTATACTACA (SEQ ID NO: 13), TAAGCTTTTTGATGTGCTGC (SEQ ID NO: 14), CCTCCCTAACTCATTTTATG (SEQ ID NO: 15), GAAGCATTCCCTTTGAAAAC (SEQ ID NO: 16), ACCTGCTCCTGAATGACTAC (SEQ ID NO: 17), TGAAGTTGCTTATCAGCTTA (SEQ ID NO: 18), GAGTTCTGTAGATGTCTATT (SEQ ID NO: 19), TATTCACAATAGCAAAGACT (SEQ ID NO: 20), TTGTCTCTTTTGATCTTTGT (SEQ ID NO: 21), TTGAACCAGCCTTGCATCCC (SEQ ID NO: 22), AGGATTCCCTATTTAATAAA (SEQ ID NO: 23), TTGCCCATTCAGTATGATAT (SEQ ID NO: 24), GTTCTTTTAATTGTGATGTT (SEQ ID NO: 25), AAGATCAAAAGAGACAAAGA (SEQ ID NO: 26), TTCACTTATGAAGCTTAGTT (SEQ ID NO: 27), AAACTAAGCTTCATAAGTGA (SEQ ID NO: 28), AAAAATCCTCAATAAAATAC (SEQ ID NO: 29), CATCTATTGAGATAATCATG (SEQ ID NO: 30), CCCAGCACCATTTATTAAAT (SEQ ID NO: 31), TCCTGAATACAGCACACTGA (SEQ ID NO: 32), TGTCTTGTGCCAGTTTTCAA (SEQ ID NO: 33), TTTGATTTGCATTTCTCTGA (SEQ ID NO: 34), ATCCCTTTACCATTATGTAA (SEQ ID NO: 35), TGAGAGATTTTGTCACCACC (SEQ ID NO: 36), AATCTGACAATTATGTGTCT (SEQ ID NO: 37), CAGTTTCAGCTTTCTACATA (SEQ ID NO: 38), CATATGTAGAAAGCTGAAAC (SEQ ID NO: 39), AATATATATGCACCCAATAC (SEQ ID NO: 40), GATGGTAGTTTGTATTTCTG (SEQ ID NO: 41), AGTCTGTTTTATCAGAGACT (SEQ ID NO: 42), GCCAGTCTGTGTCTTTTAAT (SEQ ID NO: 43), CTTCCAACACTATGTTGAAT (SEQ ID NO: 44), AAACTACTTTAAAGTTCATA (SEQ ID NO: 45), AATGTGGCACATATACACCA (SEQ ID NO: 46), CACATTCAAAAGCTAGCAGA (SEQ ID NO: 47), CCCATCAGTGTGCTGTATTC (SEQ ID NO: 48), ATCTTTCCTGCTTTCTCTTG (SEQ ID NO: 49), CTAAGCCAAAAGAACAAAGC (SEQ ID NO: 50), TCATCCCTGGGATGCAAGGC (SEQ ID NO: 51), CTCTTTGAAGCAATTGTGAA (SEQ ID NO: 52), GCCCATGCCTATGTCCTGAA (SEQ ID NO: 53), TGCCTCCAGCTTTGTTCTTT (SEQ ID NO: 54), TTTTTCCTTCATTTCAACTT (SEQ ID NO: 55), AAACTACCATCAGAGTGAAC (SEQ ID NO: 56), AGGAAAACTAACAAACAGAA (SEQ ID NO: 57), TCAAAGAGAATAAAATACCT (SEQ ID NO: 58), AAATGCCCACAAGAGAAAGC (SEQ ID NO: 59), AATGACTTTCTTCACAGAAT (SEQ ID NO: 60), ATTCACCAAAGTTGAAATGA (SEQ ID NO: 61), AATTCTGTGAAGAAAGTCAT (SEQ ID NO: 62), ATTCCAATCAATAGAAAAAG (SEQ ID NO: 63), CCTGTCATTATGATGTTAGC (SEQ ID NO: 64), CCAGCTAACATCATAATGAC (SEQ ID NO: 65), TGACCCAGCCATCCCATTAC (SEQ ID NO: 66), TACCATTCAGGACATAGGCA (SEQ ID NO: 67), CTGTTCTTTTACATTTGCTG (SEQ ID NO: 68), GATCTGTCTAATGTTGACAG (SEQ ID NO: 69), GTTCTAGTTTGATTGCACTG (SEQ ID NO: 70), TTCCCTCTTTTTCTATTGAT (SEQ ID NO: 71), TTAAAAAGTCAGGAAACAAC (SEQ ID NO: 72), ACACAACATACCAGAATCTC (SEQ ID NO: 73), AGGAAGATCTACCAAGCAAA (SEQ ID NO: 74), GTAAACTAGTTCAACCATTG (SEQ ID NO: 75), GTGCAATCAAACTAGAACTC (SEQ ID NO: 76), ACTCCTATTCAACATAGTGT (SEQ ID NO: 77), GCAGAGCTGAGTTCAATTCC (SEQ ID NO: 78), CCATCTCACACCAGTTAGAA (SEQ ID NO: 79), CCTTCACATCCCTTGTAAGT (SEQ ID NO: 80), TATCTCAATAGATGCAGAAA (SEQ ID NO: 81), TTAAGGGCACAGAGAGAA (SEQ ID NO: 82), CTAAAAACTCTCAATAAATT (SEQ ID NO: 83), TATGTACCCAGTAGTCATTC (SEQ ID NO: 84), GCTTATCCACCATGATCAAG (SEQ ID NO: 85), TGGAGAGGATGTGGAGAAAT (SEQ ID NO: 86), CTGCAGAGTGTTTTCCAACT (SEQ ID NO: 87), TCAGAGATTCAACTTCTTCC (SEQ ID NO: 88), TCTCTGAATAGACCAATAAC (SEQ ID NO: 89), GAATCTGGGTGCTCCTGTAT (SEQ ID NO: 90), CAAGTTGGAAAACACTCTGC (SEQ ID NO: 91), TAGATCCCATTTGTCAATTT (SEQ ID NO: 92), TGAAGCCCACTTGATCATGG (SEQ ID NO: 93), TCCAATTAAAAGACACAGAC (SEQ ID NO: 94), CAAAAGCCAAAATTGACAAA (SEQ ID NO: 95), GTATATACCCAGTAATGGGA (SEQ ID NO: 96), GAAATAAAGGGTATTCAATT (SEQ ID NO: 97), ACCCTCAGCTGCAGGTCTGT (SEQ ID NO: 98), CCAACTTACAAGGGATGTGA (SEQ ID NO: 99), ATTGAGAGTTTTTAGCATGA (SEQ ID NO: 100), TTTTTTGTTTTCCATTTGCT (SEQ ID NO: 101), TCTCTTCAAAGCTGTCAGAC (SEQ ID NO: 102), ATTCTTCCTACCCATGAGCA (SEQ ID NO: 103), AACACTTTTACACTGTTGGT (SEQ ID NO: 104), CTGTTTTTTCCCCATCTTTG (SEQ ID NO: 105), CAAACAACCCCATCAAAAAG (SEQ ID NO: 106), TTTCTAGTTCTAGATCCCTG (SEQ ID NO: 107), AGAACTTCCCCAATCTAGCA (SEQ ID NO: 108), TGTGAGATGGTATCTCATTG (SEQ ID NO: 109), TTTGAGTTCATTGTAGATTC (SEQ ID NO: 110), CCATGTTTAGTGCTTCCTTC (SEQ ID NO: 111), CAGTCTGAGATCAAACTGCA (SEQ ID NO: 112), TCAGTTTCCATGTAGTTGAG (SEQ ID NO: 113), TTAATCCAGTCTATCATTGT (SEQ ID NO: 114), GTCTAAAACACCAAAAGCAA (SEQ ID NO: 115), TGCCCTAAAAGAGCTCCTGA (SEQ ID NO: 116), TCACAGCCGAATTCTACCAG (SEQ ID NO: 117), AATGTCCAACAATGATAGAC (SEQ ID NO: 118), CTAGATTGGGGAAGTTCTCC (SEQ ID NO: 119), TTCTTTATTAGTCTTGCTAG (SEQ ID NO: 120), CCTCATAAAATGAGTTAGGG (SEQ ID NO: 121), GAAAAAATGCTCATCATCAC (SEQ ID NO: 122), AAGAATCAATATCGTGAAAA (SEQ ID NO: 123), GGTTTGCCAGTATTTTATTG (SEQ ID NO: 124), CTTCTCGAGGAGTATCTTTG (SEQ ID NO: 125), TTAATGATTGCCATTCTAAC (SEQ ID NO: 126), GGTAACCCGACCTTTCTCTC (SEQ ID NO: 127), AACAAAGCCTCCAAGAAATA (SEQ ID NO: 128), TAGCCCTTTGTCAGATGAGT (SEQ ID NO: 129), TAAACATGGAAAGGAACAAC (SEQ ID NO: 130), CTCCAACAGACCTGCAGCTG (SEQ ID NO: 131), GATGAGTTCATGTCCTTTGT (SEQ ID NO: 132), CAATCATGTCATCTGCAAAC (SEQ ID NO: 133), CTCTTTTAGGGCAGGCCTGG (SEQ ID NO: 134), TTTTGCATCAATGTTCATCA (SEQ ID NO: 135), CATGAACTCATCATTTTTA (SEQ ID NO: 136), ATTTTGGAATAGGTGTGGTG (SEQ ID NO: 137), AAGTTCTGGCCAGGGCAATC (SEQ ID NO: 138), AATTCGGCTGTGAATCCATC (SEQ ID NO: 139), GTGGAGCCCACCACAGCTCA (SEQ ID NO: 140), TTTCATCCATGTCCCTACAA (SEQ ID NO: 141), AAAAACAGAGATATAGATCAA (SEQ ID NO: 142), ATTGATCTATATCTCTGTTT (SEQ ID NO: 143), TAAAATCAGAGCAGAACTGA (SEQ ID NO: 144), AGTAGATAAAACCACAAAGA (SEQ ID NO: 145), GAACTACAAACCACTGCTCA (SEQ ID NO: 146), ATTGAATCTATAAATTACCT (SEQ ID NO: 147), AGTCAGTGTGGCGATTCCTC (SEQ ID NO: 148), TGTCTGTGCCCTGCCCCCAG (SEQ ID NO: 149), CGCCACACTGACTTCCACAA (SEQ ID NO: 150), TAGTTTTCCTTCTAACAGAC (SEQ ID NO: 151), AAATGTATATTCTGTTGATT (SEQ ID NO: 152), CTACTTTTGGTCTTTGATGA (SEQ ID NO: 153), AGACTCCCACACAATAATAA (SEQ ID NO: 154), GAAGCCCATCAGACTAACAG (SEQ ID NO: 155), GCCTCTGTAGGCTCCACCTC (SEQ ID NO: 156), TGGAGCCTACAGAGGCAGGC (SEQ ID NO: 157), TCCAAAATTGACCACATAGT (SEQ ID NO: 158), GATTTCTGCATTTCCATCTG (SEQ ID NO: 159), AACCTGAGAAAAACAAGCAA (SEQ ID NO: 160), TATTTCCTGAATTTGAATGT (SEQ ID NO: 161), GAACTCAGCTCTGCACCAAG (SEQ ID NO: 162), CAATACAGAGAAGTGCTTAA (SEQ ID NO: 163), CCCCATTGCTTGTTTTTCTC (SEQ ID NO: 164), TTACCAACCAAAAAGAGTCC (SEQ ID NO: 165), ATGCACACGTATGTTTATTG (SEQ ID NO: 166), CCTTTCAAAAAACCAGCTCC (SEQ ID NO: 167), AGACCAAATCTACGTCTGAT (SEQ ID NO: 168), CTTTAAGCACTTCTCTGTAT (SEQ ID NO: 169), AGTCTCCATTATTATTGTG (SEQ ID NO: 170), ATACAAAAATTAATTCAAGA (SEQ ID NO: 171), GCAACCTACTCATCTGACAA (SEQ ID NO: 172), TAATGCCTAGGTTTTCTTCT (SEQ ID NO: 173), TGGTCTAAAATTCTCTTTTT (SEQ ID NO: 174), AGTCTCTTTGTAGGTCACTC (SEQ ID NO: 175), CTCTACAAGCCAGAAGAGAG (SEQ ID NO: 176), ACACCAATCAGACGTAGATT (SEQ ID NO: 177), GTGAAGAATGCAGAAGCCTC (SEQ ID NO: 178), CTTGAATTAATTTTTGTATA (SEQ ID NO: 179), TATTGCCTAGGTTTTCTTCT (SEQ ID NO: 180), GACAGCTTTGAAGAGAGCAG (SEQ ID NO: 181), AAAATTTTCTCCCATTCTGT (SEQ ID NO: 182), CCAGTTCCTCCTTGTACCTC (SEQ ID NO: 183), GGAAGAACATTCCATGCTCA (SEQ ID NO: 184), GAATGTATATTCTGTTGATT (SEQ ID NO: 185), ATCAGATAGTTGTAGATATG (SEQ ID NO: 186), TAAGATCAGAGCAGAACTGA (SEQ ID NO: 187), ATATTAACTTTAAATGTAAA (SEQ ID NO: 188), GCATTTTTTCATGTGTTTTT (SEQ ID NO: 189), TTCAAAAAATCAATGAATCC (SEQ ID NO: 190), CACCCTCCCAAGACTAAACC (SEQ ID NO: 191), AGATTTGGGCTGAGACAAT (SEQ ID NO: 192), CACTCTCCCAAGACTAAACC (SEQ ID NO: 193), GTTTTCAACTTCTTTGCCTT (SEQ ID NO: 194), TATGTATACATGTGCCATGC (SEQ ID NO: 195), CACTAGGGAGTGCCAGACAG (SEQ ID NO: 196), ATCATCCTGATACCAAAGCC (SEQ ID NO: 197), GTGTGTCTCTGCACGTGAGA (SEQ ID NO: 198), TTTCTAGTTTATTTGCGTAG (SEQ ID NO: 199), GATTTCTGCATTTCCAACTG (SEQ ID NO: 200), TCTTTTATTTCCTTGAGCAG (SEQ ID NO: 201), TCACGTGCAGAGACACACAT (SEQ ID NO: 202), CACTCCAGACCCTGTTTGCC (SEQ ID NO: 203), ATATTAACCTTAAATGTAAA (SEQ ID NO: 204), CAGCATTTGCTTGTCTGTAA (SEQ ID NO: 205), GAGATCCGCTGTTAGTCTGA (SEQ ID NO: 206), CAGCATGATTTATAGTCCTT (SEQ ID NO: 207), CCCTACAAGCCAGAAGAGAG (SEQ ID NO: 208), ATACAAAAATCAATTCAAGA (SEQ ID NO: 209), ATTTAGCCCATTTACATTTA (SEQ ID NO: 210), TTTTTTGTTGTGTCTCTGCC (SEQ ID NO: 211), AGGGGTCAGGGACCCACTTG (SEQ ID NO: 212), TTTCTAGTTTATTTGCATAG (SEQ ID NO: 213), CTTGAATTGATTTTGTATA (SEQ ID NO: 214), TGAATGTGTCCCAGAGATTC (SEQ ID NO: 215), AAAATTTTCTCCCATTTTGT (SEQ ID NO: 216), TGTTGTGTCTTTGTTCTCGT (SEQ ID NO: 217), AGCAAAGCCTCCAAGAAATA (SEQ ID NO: 218), AAGTTCTGGCCAGGGCAATT (SEQ ID NO: 219), ATTGAATCTGTAAATTACCT (SEQ ID NO: 220), AGACTCCCACACATTAATAA (SEQ ID NO: 221), CCATTCTCCCCATCACTTTC (SEQ ID NO: 222), GCTCTCTGTTTGTCTGTTAT (SEQ ID NO: 223), AGTCTCCCATTATTAATGTG (SEQ ID NO: 224), GTACAGATGGGTTTTTGGTG (SEQ ID NO: 225), TGCCTCCCAGTTAGGCTGCT (SEQ ID NO: 226), CCCACTCTCTTCTGGCTTGT (SEQ ID NO: 227), GCTGATGGAGCTGAAAACCA (SEQ ID NO: 228), ACTCCCTAGTGAGATGAACC (SEQ ID NO: 229), TTCAAAAAATTAATGAATCC (SEQ ID NO: 230), CACCTATGAGTGAGAATATG (SEQ ID NO: 231), ACATTCAAAGCAGTGTGTAG (SEQ ID NO: 232), AACATTCCATGCTCATGGGT (SEQ ID NO: 233), CTTCTCCTGCCTAATTGCCC (SEQ ID NO: 234), TTTGTTTACCTAAGCAAGCC (SEQ ID NO: 235), TCTTTTATTTCATTGAGCAG (SEQ ID NO: 236), ACTGCTCAATGAAATAAAAG (SEQ ID NO: 237), CCTGAAAGTGATGGGGAGAA (SEQ ID NO: 238), TAGTTTTCCTTCTAACAGTC (SEQ ID NO: 239), ATTTTGGCATGATTTTGCAG (SEQ ID NO: 240), CTTTGGTTCTGTTTATATGC (SEQ ID NO: 241), GACACAATAAAAAATGATAA (SEQ ID NO: 242), TTTCTTCCAGTTGATCGCAT (SEQ ID NO: 243), CTTTTCAAAAAACCAGCTCC (SEQ ID NO: 244), TTCACGTAGTTCTCGAGCCT (SEQ ID NO: 245), GAGCGCCTCTCCTCCTCCAA (SEQ ID NO: 246), TCAGATCTCCAGCTGCGTGC (SEQ ID NO: 247), AATTGAACAATGAGAACACA (SEQ ID NO: 248), ATGAATGAAATGAAGCGAGA (SEQ ID NO: 249), CAGTTTCTTCCTAGTCTCGA (SEQ ID NO: 250), CACCGCATATTCTCACTCAT (SEQ ID NO: 251), CTCAAAACCGCTCAACTACA (SEQ ID NO: 252), TCCACCCAGTTCGAGCTTCC (SEQ ID NO: 253), TGTTGTGTCTTTGTTCTCAT (SEQ ID NO: 254), GATGCGATCAACTGGAAGAA (SEQ ID NO: 255), GTACCAGTACCATGCTGTTT (SEQ ID NO: 256), AAAAAACAGAGCAGAAAAAC (SEQ ID NO: 257), CTTTGGTATCAGGATGATGC (SEQ ID NO: 258), AAAAAACAGAACAGAAAAAC (SEQ ID NO: 259), GTGCTTTACTTCCAACTATG (SEQ ID NO: 260), TAGATAAAACCACAAAGATG (SEQ ID NO: 261), TGACCCCCGAGCAGCCTAAC (SEQ ID NO: 262), AATTTGCATGTTTTTGCAG (SEQ ID NO: 263), TAAAAGAGGATACAAACAAA (SEQ ID NO: 264), GCATTCAAAGCAGTGTGTAG (SEQ ID NO: 265), GAGGAACTGCGTTCCTTTGG (SEQ ID NO: 266), TTTGACGAGCTGAGAGAAGA (SEQ ID NO: 267), CTTTGGTATCAGAATGATGC (SEQ ID NO: 268), ATTCTTCCTATCCATGAGCA (SEQ ID NO: 269), TCCCTTTCCTAGTCAAAGAA (SEQ ID NO: 270), AAAACAGAGATATAGACCAA (SEQ ID NO: 271), CTTCTCCTGCCTGATTGCCC (SEQ ID NO: 272), TGGGAGTGACCCGATTTCC (SEQ ID NO: 273), ATGTAAAGACCATCGAGACT (SEQ ID NO: 274), CCATTCTCCCGTCACTTTC (SEQ ID NO: 275), TCACCATCATCAAAGACCAA (SEQ ID NO: 276), ATTATTATACTTTAAGTTTT (SEQ ID NO: 277), TCAATTTCAGAGCCTGTTAT (SEQ ID NO: 278), GCTCTCTGTTTGTCTGTTGT (SEQ ID NO: 279), AACGAGACAGAAAGTCAACA (SEQ ID NO: 280), CAGCATGATTTATAATCCTT (SEQ ID NO: 281), GATCAAATTACTCTGAGCTA (SEQ ID NO: 282), GATGCAATAAAAAATGATAA (SEQ ID NO: 283), CTTTGGCTCTGTTTATATGC (SEQ ID NO: 284), TGTCACCCCTTTCTTTGACT (SEQ ID NO: 285), GGTCAGGGACCCACTTGAGG (SEQ ID NO: 286), CTCTGAGACAAAACTTCCAG (SEQ ID NO: 287), CTGGCCTCATAAAATGAGTT (SEQ ID NO: 288), CTTCATCCATGTCCCTACAA (SEQ ID NO: 289), CCTGAAAGTGACGGGGAGAA (SEQ ID NO: 290), CACCTATGAGTGAGAACATG (SEQ ID NO: 291), TATTTCCTGAATCTGAACGT (SEQ ID NO: 292), AGGAGCCAAGATGGCCGAAT (SEQ ID NO: 293), AAGAATCAATATCATGAAAA (SEQ ID NO: 294), GCCATTGCCCAGGCTTGCTT (SEQ ID NO: 295), CGCAGCTGGAGATCTGAGAA (SEQ ID NO: 296), AATTGAACAATGAGATCACA (SEQ ID NO: 297), CAATCATGTCGTCTGCAAAC (SEQ ID NO: 298), AGACCGGAGCTGTTCCTATT (SEQ ID NO: 299), TATTTCCTGAATCTGAATGT (SEQ ID NO: 300), TGCCTTACAAGAGCTCCTGA (SEQ ID NO: 301), TTGGGAGAGTGTATGTGTCG (SEQ ID NO: 302), GGAAGGGGAACATCACACTC (SEQ ID NO: 303), TAAATGTGTCCCAGAGATTC (SEQ ID NO: 304), AGGTGTCAGTGTGCCCCTGC (SEQ ID NO: 305), TTAGGATTGACTTGGCGATG (SEQ ID NO: 306), TTCCAACAGACCTGCAGCTG (SEQ ID NO: 307), AACCTGACAAAAACAAGCAA (SEQ ID NO: 308), TATGTATACATGTGCCATGT (SEQ ID NO: 309), AACCTGACAAAAACAAGAAA (SEQ ID NO: 310), TTAATGATCGCCATTCTAAC (SEQ ID NO: 311), GTCCTTCGCCCACTTTTTGA (SEQ ID NO: 312), TCCAAAATTGACCACATACT (SEQ ID NO: 313), AGATTTTGGGCTGAGACGAT (SEQ ID NO: 314), TGAATGCGTCCCAGAGATTC (SEQ ID NO: 315), AGACTGGAGCTGTTCCTATT (SEQ ID NO: 316), ATACTATGCAGCCATAAAAA (SEQ ID NO: 317), GGGCAGACTGACACCTCACA (SEQ ID NO: 318), ATCCTTGCCCACTTTTTGA (SEQ ID NO: 319), GGAAGGGGAATATCACACTC (SEQ ID NO: 320), ACGCAGTTCCTCACCAGCAA (SEQ ID NO: 321), AATGCTAGATGACGAGTTAG (SEQ ID NO: 322), GACAGCTTTGAAGAGAGTAG (SEQ ID NO: 323), GAGCTTTACTTCCAACTATG (SEQ ID NO: 324), CATGAACTCATCCTTTTTTA (SEQ ID NO: 325), CTAACTCGTCATCTAGCATT (SEQ ID NO: 326), ATCCAGCTTTGTTCCGTTGC (SEQ ID NO: 327), AGTCTCTTTGTAGGTCTCTA (SEQ ID NO: 328), CCATGTTTAGCGCTTCCTTC (SEQ ID NO: 329), CCCCATTGCTGTTTTTGTC (SEQ ID NO: 330), GAGCTTTACTTCCAAGTATG (SEQ ID NO: 331), GACGCAATAAAAAATGATAA (SEQ ID NO: 332), CTAGGTTGGGGAAGTTCTCC (SEQ ID NO: 333), ATCAGATGGTTGTAGATGTG (SEQ ID NO: 334), CCCCATTTCTTGTTTTTGTC (SEQ ID NO: 335), GGGCACACTGACACCTCACA (SEQ ID NO: 336), CTACCTTTGGTCTTTGATGA (SEQ ID NO: 337), GACTAAAACACCAAAAGCAA (SEQ ID NO: 338), TTTCTAGTTCTAGATCCTTG (SEQ ID NO: 339), GAAAAAATGCTCACCATCAC (SEQ ID NO: 340), TTAGGATTGACTTGGCAATG (SEQ ID NO: 341), TTTTGTCTCAGAGGAGTACC (SEQ ID NO: 342), ACATTTAAAGCAGTGTGTAG (SEQ ID NO: 343), CCAGCTCCTCCTTGTACCTC (SEQ ID NO: 344), CTCTTGTAAGGCAGGCCTGG (SEQ ID NO: 345), GAGATCTGCTGTTAGTCTGA (SEQ ID NO: 346), GAGATCAGCTGTTAGTCTGA (SEQ ID NO: 347), AGGGCTCTGTTCTGTTCCAT (SEQ ID NO: 348), AACGAGACAGAAAGTTAACA (SEQ ID NO: 349), CTAAGCAAAAAGAACAAAGC (SEQ ID NO: 350), TTTTTCCTTCATTTCAACCT (SEQ ID NO: 351), CCAGCTCCTCTTTGTACCTC (SEQ ID NO: 352), GTTCTAATTTGATTGCACTG (SEQ ID NO: 353), AAGAATCAATATTGTGAAAA (SEQ ID NO: 354), GTGCAATCAAATTAGAACTC (SEQ ID NO: 355), AGCGTGAGCGACGCAGAAGA (SEQ ID NO: 356), TTTGACGAGTTGAGAGAAGA (SEQ ID NO: 357), CAAAAGACAAAATTGACAAA (SEQ ID NO: 358), CATCATTCTGATACCAAAGC (SEQ ID NO: 359), CAGCTTTGTTCTTTTTGCTT (SEQ ID NO: 360), TCTTTTGTTGCCATTGCTTT (SEQ ID NO: 361), GACTGTTGTGGGGTGGGGGG (SEQ ID NO: 362), GTGTGTCTCTGCATGTGAGA (SEQ ID NO: 363), TATTTACCCAGTAGTCATTC (SEQ ID NO: 364), TCACAGCCAAATTCTACCAG (SEQ ID NO: 365), GTCTTCTGCGTCGCTCACGC (SEQ ID NO: 366), CTCAAAACCACTCAACTACA (SEQ ID NO: 367), TTTCTCTTGCCTGATTGCCC (SEQ ID NO: 368), ACAATTTCAGCTCCTGTTAT (SEQ ID NO: 369), AGTTTGCCAGTATTTTATTG (SEQ ID NO: 370), CTAAAAACTCTCAATAAACT (SEQ ID NO: 371), AGAACTTCCCCAACCTAGCA (SEQ ID NO: 372), TTTCTAGTTTATTTGTGTAG (SEQ ID NO: 373), TTGGGAGGGTGTATGTGTCC (SEQ ID NO: 374), CAATGCAGAGAAGTCCTTAA (SEQ ID NO: 375), ACCTACTCAAGCCTCAGCAA (SEQ ID NO: 376), TCACATGCAGAGACACACAT (SEQ ID NO: 377), GAGCACCTCTCCTCCTCCAA (SEQ ID NO: 378), TCCCTTTCCGAGTCAAAGAA (SEQ ID NO: 379), CGGCAGCGAGGCTGGGGGAG (SEQ ID NO: 380), GTCCAAAACACCAAAAGCAA (SEQ ID NO: 381), GCATTTTTTCATGTGTCTGT (SEQ ID NO: 382), CATCATCCTGATACCAAAGC (SEQ ID NO: 383), CCCAATTAAAAGACACAGAC (SEQ ID NO: 384), ACAATTCAGATCCTGTTAT (SEQ ID NO: 385), TCACAGCTGAATTCTACCAG (SEQ ID NO: 386), TTACCAACCAAAAAAGTCC (SEQ ID NO: 387), GTGTGTCTCTGCACATGAGA (SEQ ID NO: 388), GCCTCTGTAGACTCCACCTC (SEQ ID NO: 389), AGGTGTCAGTCTGCCCTAC (SEQ ID NO: 390), ACTGACCTGCGCCCACTGTC (SEQ ID NO: 391), TCATGTGCAGAGACACACAT (SEQ ID NO: 392), GGTAACCTGACCTTTCTCTC (SEQ ID NO: 393), GCAATCTACTCATCTGACAA (SEQ ID NO: 394), CACCGCATGTTCTCACTCAT (SEQ ID NO: 395), TAGCAATCAGCGAGACTCCG (SEQ ID NO: 396), AAATGAAGGAAAAAATGTTA (SEQ ID NO: 397), ACAAAGAGAATAAAATACCT (SEQ ID NO: 398), TTAATCCAGTCTATCATTGA (SEQ ID NO: 399), GTAAATTAGTTCAACCATTG (SEQ ID NO: 400), AGGACCCTCCGAGCCAGGTG (SEQ ID NO: 401), CGTCACCCCTTTCTTTGACT (SEQ ID NO: 402), ATGAGTTCATGTCCTTTGTA (SEQ ID NO: 403), ACAATTTCAGAGCCTGTTAT (SEQ ID NO: 404), CCATTCTCCCTGTCACTTTC (SEQ ID NO: 405), GATCTGTCTAATATTGACAG (SEQ ID NO: 406), AATGTCCATCAATGATAGAC (SEQ ID NO: 407), CTCGGAGGGTCCTACGCCCA (SEQ ID NO: 408), TTTAAGTTCTTTGTAGATTC (SEQ ID NO: 409), CACCAGCAACAGAACAAAGC (SEQ ID NO: 410), TCATCTCACACCAGTTAGAA (SEQ ID NO: 411), AGACCAAATCTACATCTGAT (SEQ ID NO: 412), GAGATCCACTGTTAGTCTGA (SEQ ID NO: 413), TGACCCAGCAATCCCATTAC (SEQ ID NO: 414), ATCCAGCTTTGTTCCATTGC (SEQ ID NO: 415), GGAAGGGGAACATCACACAC (SEQ ID NO: 416), GCATTTTTTCATGTGTCTTT (SEQ ID NO: 417), CTCAAAACTGCTCAACTACA (SEQ ID NO: 418), TGCCTCCCAGTTAGGCTACT (SEQ ID NO: 419), TTTATTATACTTTAAGTTTT (SEQ ID NO: 420), CCTGATGGAGCTGAAAACCA (SEQ ID NO: 421), GTCCAGCTTTGTTCCATTGC (SEQ ID NO: 422), GTCCTTTGCCCACTTTTTGA (SEQ ID NO: 423), ACACCAATCAGATGTAGATT (SEQ ID NO: 424), CAGCTCCATCAGGTCCTTTA (SEQ ID NO: 425), GAGTGCCTCTCCTCCTCCAA (SEQ ID NO: 426), AGATTTTGGGCTGAGATGAT (SEQ ID NO: 427), AATTCAGCTGTGAATCCATC (SEQ ID NO: 428), TATTGGGTGCATATATATTT (SEQ ID NO: 429), CCTGAAAGTGACAGGGAGAA (SEQ ID NO: 430), AAAACAACCCCATCAAAAAG (SEQ ID NO: 431), TTAATGATCACCATTCTAAC (SEQ ID NO: 432), CTACCAACCAAAAAAGTCC (SEQ ID NO: 433), CTGAAGAGTGTTTTCCAACT (SEQ ID NO: 434), CTTCTCAAGGAGTATCTTTG (SEQ ID NO: 435), CAGACTAACAGCTGATCTCT (SEQ ID NO: 436), CACCGTGCGCGAGCCGAAGC (SEQ ID NO: 437), CTTCATCCATGTCCCTGCAA (SEQ ID NO: 438), GGCAATGCCTCGCCCTGCTT (SEQ ID NO: 439), ATTGAATCTATAAATTACTT (SEQ ID NO: 440), CTCTTTGTAGCAATTGTGAA (SEQ ID NO: 441), CTTCTTGAGGAGTATCTTTG (SEQ ID NO: 442), TTTTTGCATCGATGTTCATC (SEQ ID NO: 443), CAGCTCCATCAGGTCATTTA (SEQ ID NO: 444), GAGTGAGAACATGCAGTGTT (SEQ ID NO: 445), AGTCAGGAAACAACAGATGC (SEQ ID NO: 446), CGATAGTTTGCTGAGAATGA (SEQ ID NO: 447), AATTTTCAGCTTTTCTGCTC (SEQ ID NO: 448), ATACCCAGTAATGGGATTGC (SEQ ID NO: 449), GAGGAGCTGCGTTCCTTTGG (SEQ ID NO: 450), AATTGAACAATGAGAACACT (SEQ ID NO: 451), AATGCTAAATGACGAGTTAA (SEQ ID NO: 452), TTTTTTGCTTTCCATTTGCT (SEQ ID NO: 453), ATGAATGAAATGAAGTGAGA (SEQ ID NO: 454), ATTCTCAGCAAACTATCGCA (SEQ ID NO: 455), CAAGTTGGAAAACACTCTTC (SEQ ID NO: 456), ATCATTCTGATACCAAAGCC (SEQ ID NO: 457), ACAACCTACTCATCTGACAA (SEQ ID NO: 458), TAGCATCAACATCAACAAAA (SEQ ID NO: 459), CAGTTTCTTCCTAGCCTTGA (SEQ ID NO: 460), AATTTGGCTGTGAATCCATC (SEQ ID NO: 461), TTTGTGGTTTATCTACCTT (SEQ ID NO: 462), GCTGATGGAGCTGAAAGCCA (SEQ ID NO: 463), TTAACTCGTCATTTAGCATT (SEQ ID NO: 464), TGATAGTTTGCTGAGAATGA (SEQ ID NO: 465), GTTTTGCCAGTATTTTATTG (SEQ ID NO: 466), ATCCAGCTTTGTTCTGTTGC (SEQ ID NO: 467), AAGAACTTGCTTTATGAATC (SEQ ID NO: 468), CCTGACCCCTTGCGCTTCCC (SEQ ID NO: 469), TTGGGAGGGTGTATGTGTCG (SEQ ID NO: 470), CAGACTAACAGCAGATCTCT (SEQ ID NO: 471), TTGCTGCCTGATCCTTCCTC (SEQ ID NO: 472), TCTAAAATTGACCACATAAT (SEQ ID NO: 473), CTCAAAGCCGCTCAACTACA (SEQ ID NO: 474), ATACAAAAATTAACTCAAGA (SEQ ID NO: 475), ACAGACGGCACCTGGAAAAT (SEQ ID NO: 476), TCACCAACATCAAAGACCAA (SEQ ID NO: 477), GTCCAGCTTTGTTCCGTTGC (SEQ ID NO: 478), ATACCCAGGCAAACAGGGTC (SEQ ID NO: 479), CGCCACACTGTCTTCCACAA (SEQ ID NO: 480), CTTCCAATACTATGTTGAAT (SEQ ID NO: 481), AGCAGCCGGGAAGCTCGAAC (SEQ ID NO: 482), ACTCCTATTCAACATGTAT (SEQ ID NO: 483), GTGTTTTACTTCCAATTATG (SEQ ID NO: 484), AAAGGGATCAATTCAACAAG (SEQ ID NO: 485), AATGAGACAGAAAGTTAACA (SEQ ID NO: 486), GACGGACGCACCTGGAAAAT (SEQ ID NO: 487), CTTGAGTTAATTTTTGTATA (SEQ ID NO: 488), AAAATTTTCTCCCATGTTGT (SEQ ID NO: 489), GAAAATCCTCAATAAAATAC (SEQ ID NO: 490), TTTCTCCTGCCTGATTGCCC (SEQ ID NO: 491), ATATTAGCCCTTTGTCAGAT (SEQ ID NO: 492), GGTAACCCAACCTTTCTCTC (SEQ ID NO: 493), AAACTATCATCAGAGTGAAC (SEQ ID NO: 494), AAAACAGATATATAGACCAA (SEQ ID NO: 495), TGCCTCACCTGGGAAGCGCA (SEQ ID NO: 496), TGCCATTGCTTTTGGTGTTT (SEQ ID NO: 497), AGGAAGATCTACCAAGCCAA (SEQ ID NO: 498), TGCCTTTTTTTGTTTTCCAT (SEQ ID NO: 499), ATTCTCAGCAAACTATCACA (SEQ ID NO: 500), CTGGACTTTTTTTGGTTGGT (SEQ ID NO: 501), CAGTTTCTTCCTAGCCTCGA (SEQ ID NO: 502), TAG-GAACACTTTTACACTGT (SEQ ID NO: 503), ACGA-GACTATATCCCACACC (SEQ ID NO: 504), GAATAT-TGCGCTTTTCAGAC (SEQ ID NO: 505), TTTGAGTTCTTTGTAGATTC (SEQ ID NO: 506), ATGCACATGTATGTTTATTG (SEQ ID NO: 507), TCAGGGATTCAACTTCTTCC (SEQ ID NO: 508), ATGCACACATATGTTTATTG (SEQ ID NO: 509), GCAGGGCATAGCTGAACAAA (SEQ ID NO: 510), TCAGATCTCCAGCTGCATGC (SEQ ID NO: 511), AATAACAAGTTCTGAAATTG (SEQ ID NO: 512), TGT-GAGATGATATCTCATAG (SEQ ID NO: 513), ATCATCCTGATACCAAAACC (SEQ ID NO: 514), AGGCCTCTGTTCTGTTCCAT (SEQ ID NO: 515), TGACCCCGAGTAGCCTAAC (SEQ ID NO: 516), GCC-CACGCCTATGTCCTGAA (SEQ ID NO: 517), TCAAT-TTCAGAACTTGTTAT (SEQ ID NO: 518), TACCAT-TCAGGACATAGGCG (SEQ ID NO: 519), CACCACATGTTCTCACTCAT (SEQ ID NO: 520), AGGACCCTCTGAGCCAGGTG (SEQ ID NO: 521), CAT-AATTGTCAGATTCACCA (SEQ ID NO: 522), and GAA-GACCTTAAATGACCTGA (SEQ ID NO: 523). Sequences are presented from 5' to 3'.

Provided herein are methods of obtaining sequences from a desired location, such as a LINE element. In some cases, the LINE element comprises a nucleotide polynucleotide having comprising SEQ ID NO: 1. In some cases, a portion of the LINE element is targeted, the portion having a sequence comprising SEQ ID NO: 2. In some cases, the LINE element is targeted using a guide RNA having a sequence comprising SEQ ID NO: 3.

Provided herein are methods of obtaining sequences adjacent to a desired location, such as an Alu element. In some cases, the Alu element comprises an Alu-Y element having a sequence comprising SEQ ID NO: 4.

In some cases, the desired genomic location is amplified by a DNA polymerase, for example a strand-displacing DNA polymerase. In some cases a DNA polymerase is used to amplify the desired genomic location. In some cases the DNA polymerase requires a primer sequence to be included in the tag, for example a DNA primer or an RNA primer.

Tags are inserted into a sample of genomic DNA by genome editing or gene targeting methods known by skill in the art. In some cases, tags are inserted into the genomic DNA of a cell, such as an isolated cell from a patient or a cultured cell. In some cases, tags are inserted into genomic DNA that has been isolated from a cell or tissue, such as a cell or tissue sample from a patient.

Alternatively, hairpin tags are inserted into a sample of genomic DNA by genome editing or gene targeting methods known by skill in the art. In some cases, hairpin tags are inserted into the genomic DNA of a cell, such as an isolated cell from a patient or a cultured cell. In some cases, hairpin tags are inserted into genomic DNA that has been isolated from a cell or tissue, such as a cell or tissue sample from a patient.

Genome editing or gene targeting technology is understood by one of skill in the art and includes methods such as homologous recombination, clustered regularly-interspaced short palindromic repeats (CRISPR), (transcription activator-like effector nucleases (TALENS), Zinc fmger nucleases, transposons, and other methods. The result of any of these methods is a specific insertion into the genome of one or more nucleic acid tags comprising at least one promoter sequence.

In methods described herein, the tag to be inserted into the desired genomic location is a nucleic acid. Depending on the exact mechanism of genomic targeting the nucleic acid tag is a RNA or a DNA. In some cases the nucleic acid tag is a RNA/DNA hybrid. Nucleic acid tags are prepared for a gene targeting reaction by methods known by one of skill in the art. In some cases, tags are synthesized by nucleic acid synthesizers. In some cases, tags are prepared by recombinant DNA technology. An RNA nucleic acid tag, in some cases is transcribed from a plasmid. Depending on the method of insertion, the sequence complementary to the desired genomic location will vary to accommodate the method. In some cases, CRISPR requires a PAM sequence that must be located in the genomic location to be targeted.

In additional methods described herein, the hairpin tag to be inserted into the desired genomic location is a nucleic acid. Depending on the exact mechanism of genomic targeting the nucleic acid tag is a RNA or a DNA. In some cases the hairpin nucleic acid tag is a RNA/DNA hybrid. Hairpin nucleic acid tags are prepared for a gene targeting reaction by methods known by one of skill in the art. In some cases, hairpin tags are synthesized by nucleic acid synthesizers. In some cases, hairpin tags are prepared by recombinant DNA technology. An RNA nucleic acid hairpin tag, in some cases is transcribed from a plasmid. Depending on the method of insertion, the sequence complementary to the desired genomic location will vary to accommodate the method. In some cases, CRISPR requires a PAM sequence that must be located in the genomic location to be targeted.

In some cases, CRISPR is used to insert the tagged nucleic acid sequence into a specific location in the genomic DNA sample. CRISPR generally uses two components, a guide RNA (gRNA) and a non-specific CRISPR-associated endonuclease (Cas9). In some cases, a CRISPR gRNA requires a scaffold sequence for Cas9 binding and a targeting sequence of about 20 nucleotides containing the tag and the genomic DNA sequence to be modified.

Alternatively, CRISPR is used to insert the hairpin tag nucleic acid sequence into a specific location in the genomic DNA sample. CRISPR generally uses two components, a guide RNA (gRNA) and a non-specific CRISPR-associated endonuclease (Cas9). In some cases, a CRISPR gRNA requires a scaffold sequence for Cas9 binding and a targeting sequence of about 20 nucleotides containing the tag and the genomic DNA sequence to be modified.

Also disclosed herein are methods comprising insertion of a tagged nucleic acid sequence into a CRISPR targeted site in a DNA sample. In these methods, a CRISPR/CAS nuclease creates a double stranded break at a targeted site in the genome. An exonuclease is then added to the reaction mixture which degrades one strand of the double stranded break creating a sticky end with a specific nucleic acid sequence. Alternatively, a second targeted CRISPR/CAS nuclease is used to create a sticky end intead of the exonuclease. The tagged nucleic acid polynucleotide comprises a single stranded nucleic acid having portion comprising a transcriptional promoter such as a T7 promoter and a portion comprising a nucleic acid sequence complementary to the sticky end. Optionally, the tagged nucleic acid polynucleotide comprises a portion that is self-complementary allowing the tagged nucleic acid to form a hairpin.

Further disclosed herein are methods comprising insertion of a hairpin tag nucleic acid sequence into a CRISPR targeted site in a DNA sample. In these methods, a CRISPR/CAS nuclease creates a double stranded break at a targeted site in the genome. An exonuclease is then added to the reaction mixture which degrades one strand of the double stranded break creating a sticky end with a specific nucleic acid sequence. Alternatively, a second targeted CRISPR/CAS nuclease is used to create a sticky end intead of the exonuclease. The hairpin tag nucleic acid polynucleotide comprises a nucleic acid having a double stranded portion comprising a transcriptional promoter such as a T7 promoter connected by a loop to a single stranded portion comprising a nucleic acid sequence complementary to the sticky end. The double stranded portion is self-complementary allowing the hairpin tag nucleic acid to form a hairpin.

Linear Amplification of Nucleic Acids

Methods provided herein allow for obtaining precise and accurate sequence information from nucleic acid molecules with sequences known by one of skill in the art to be difficult to sequence. Methods herein use targeted nucleic acid sequences that are amplified in a linear fashion directly from the starting genomic DNA template. As would be appreciated by one of skill in the art, genomic regions that are difficult to sequence have characteristics which are known to have increased rates of replication errors such as insertions, deletions, and substitutions, caused by DNA polymerases, such as Taq polymerase. In amplification methods such as PCR, these errors are passed on with each round of amplification, creating amplification-specific sequencing errors that do not reflect the original template.

Methods disclosed herein include linear amplification, that is creation of additional nucleic acid molecules identical to the original genomic DNA template, synthesized directly from the original template. In some cases, linear amplification is achieved using transcription, for example in vitro transcription of RNA from a specific genomic DNA location that has been specifically tagged to contain a promoter sequence as described herein. Suitable RNA polymerases include but are not limited to T7 RNA polymerase, T3 RNA polymerase SP6 RNA polymerase, RNA polymerase I, RNA polymerase II, RNA polymerase III RNA polymerase IV. In some cases, RNA is transcribed by a RNA polymerase V, single subunit RNA polymerase. In some cases, the in vitro transcription reaction requires one or more ribonucleotides (ATP, GTP, UTP, and CTP) and buffers suitable to the RNA polymerase.

Purification of Linearly Amplified Nucleic Acids

Methods disclosed herein provide for purification of the linearly amplified nucleic acid from the genomic DNA template. In some instances, the method of purification is an enzymatic method whereby the genomic DNA template is digested using one or more DNases. Alternately, the method of purification is an affinity based purification whereby the resulting amplified nucleic acid is labeled and a reagent such as an antibody binds to the labeled amplified nucleic acids and the unbound genomic DNA template is washed away from the bound amplified nucleic acids. The method of purification is also contemplated to be a fluorescence based sorting purification, whereby fluorescently labeled amplified nucleic acids are sorted away from unlabeled genomic DNA template. Further purification methods include wherein the amplified nucleic acids are purified from the amplification reaction after each round of amplification. In further methods, the amplified nucleic acids are purified after the amplification reaction is complete.

Methods disclosed herein provide for an amplified nucleic acid that is an RNA. In instances where it is desired to have a DNA sample for downstream steps in methods, a DNA copy is made from the RNA using one or more reverse transcriptase enzymes. Optionally, the RNA is polyadenylated prior to treatment with reverse transcriptase. Alternately, the reverse transcriptase uses an oligo dT for priming the reverse transcriptase reaction. The reverse transcriptase is also contemplated to use a gene specific primer for priming the reverse transcriptase reaction. The reverse transcriptase optionally uses random hexamer primers for priming the reverse transcriptase reaction. It is also contemplated that, the reverse transcriptase uses a buffer and deoxyribonucleotides.

Border-Adjacent Libraries and Sequence Databases

Disclosed herein are nucleic acid libraries comprising molecules comprising mobile element edges or borders and mobile element adjacent genomic or other non-mobile element sequence, paired in nucleic acid molecules such that library constituent molecules have both a mobile element border and mobile element adjacent sequence so as to identify the mobile element location within a genome or other nucleic acid source.

As discussed elsewhere in the present disclosure, libraries consistent with the disclosure comprise molecules generated through iterative linear amplification of products direct from a sample template. Accordingly, such libraries do not suffer from differential amplification artifacts that arise from chain-reaction based amplification methods that involve early rounds of amplification to yield products being used as templates in subsequent amplification reactions, resulting in early amplification errors being propagated in later products. Through linear amplification, particularly but not exclusively through an RNA intermediary, amplification products are uniquely and distinctly derived directly from the template. Any error in generation of a particular amplification product is not propagated in subsequent reactions, because the amplification products do not serve as templates for chain reaction amplification in library generation. Errors in amplification occur, but are independent of one another, individually rare, and easily recognized by comparison to related amplification products of the same template.

Often, libraries consistent with the disclosure herein are derived from genomic DNA, but other nucleic acid sources are also contemplated. Libraries consistent with the disclosure herein often share a common element of being enriched for mobile element border and border adjacent sequence containing molecules relative to a genomic or other nucleic acid sample from which the libraries are derived. That is, relative to a genomic sample, a greater number of nucleic acid molecules comprise both a mobile element border and border-adjacent sequence, or a greater proportion of the total sequence of the library is in proximity to a mobile element border.

Libraries herein comprise at least 100, 200, 500, 1,000, 5,000, 10,000, 20,000, 50,000, 100,000, 200,000, 500,000, 1,000,000, or more than 1,000,000 nucleic acid molecules. Some libraries disclosed herein comprise at least 10×, 20×, 50×, 100×, 200×, 500×, 1,000×, 2,000×, 5,000×, 10,000×, 20,000×, 50,000×, 100,000 or greater than 100,000× the number of chromosomes in a haploid complement of chromosomes of a nucleic acid sample.

In some cases 10%, 20%, 30%, 40%, 50%, 60%, 70%, 80%, 85%, 90%, 91%, 92%, 93%, 94%, 95%, 96%, 97%, 98%, 99%, or more than 99%, such as 99.5%, 99.6%, 99.7%, 99.8%, 99.9%, about 100%, or 100% of the library constituents comprise both a mobile element border and border-adjacent sequence.

'Sequence in proximity to a mobile element border' is variously understood to refer to sequence (measured at a given base position) for which a mobile element border is located no more than 20 kb, 15 kb, 10 kb, 9 kb, 8 kb, 7 kb, 6 kb, 5 kb, 4 kb, 3 kb, 2 kb, 1 kb, 900 bases, 800 bases, 700 bases, 600 bases, 500 bases 400 bases, 300 bases, 200 bases, 100 bases, or less than 100 bases from the sequence.

In libraries consistent with the disclosure herein, sequence in proximity to a mobile element border represents a greater proportion of the overall sequence of the library than in a related sample such as a genomic sample from which the library is generated. In some cases 10%, 20%, 30%, 40%, 50%, 60%, 70%, 80%, 85%, 90%, 91%, 92%, 93%, 94%, 95%, 96%, 97%, 98%, 99%, or more than 99%, such as 99.5%, 99.6%, 99.7%, 99.8%, 99.9%, about 100%, or 100% of the library constituents comprise sequence in proximity to a mobile element border.

Also disclosed herein are nucleic acid libraries comprising molecules comprising repetitive region edges or borders and repetitive region adjacent genomic or other non-repetitive region sequence, paired in nucleic acid molecules such that library constituent molecules have both a repetitive region border and repetitive region adjacent sequence so as to identify the repetitive region location within a genome or other nucleic acid source.

Often, libraries consistent with the disclosure herein are derived from genomic DNA, but other nucleic acid sources are also contemplated. Libraries consistent with the disclosure herein often share a common element of being enriched for repetitive region border and border adjacent sequence containing molecules relative to a genomic or other nucleic acid sample from which the libraries are derived. That is, relative to a genomic sample, a greater number of nucleic acid molecules comprise both a repetitive region border and border-adjacent sequence, or a greater proportion of the total sequence of the library is in proximity to a repetitive region border.

In some cases 10%, 20%, 30%, 40%, 50%, 60%, 70%, 80%, 85%, 90%, 91%, 92%, 93%, 94%, 95%, 96%, 97%, 98%, 99%, or more than 99%, such as 99.5%, 99.6%, 99.7%, 99.8%, 99.9%, about 100%, or 100% of the library constituents comprise both a repetitive region border and border-adjacent sequence.

'Sequence in proximity to a repetitive region border' is variously understood to refer to sequence (measured at a given base position) for which a repetitive region border is located no more than 20 kb, 15 kb, 10 kb, 9 kb, 8 kb, 7 kb, 6 kb, 5 kb, 4 kb, 3 kb, 2 kb, 1 kb, 900 bases, 800 bases, 700 bases, 600 bases, 500 bases 400 bases, 300 bases, 200 bases, 100 bases, or less than 100 bases from the sequence.

In libraries consistent with the disclosure herein, sequence in proximity to a repetitive region border represents a greater proportion of the overall sequence of the library than in a related sample such as a genomic sample from which the library is generated. In some cases 10%, 20%, 30%, 40%, 50%, 60%, 70%, 80%, 85%, 90%, 91%, 92%, 93%, 94%, 95%, 96%, 97%, 98%, 99%, or more than 99%, such as 99.5%, 99.6%, 99.7%, 99.8%, 99.9%, about 100%, or 100% of the library constituents comprise sequence in proximity to a repetitive region border.

Libraries consistent with the disclosure comprise fragments that comprise both a repetitive region border and border-adjacent sequence and that span at least 50, 100, 200, 300, 400, 500, 600, 700, 800, 900, 1,000, 1,500, 2,000, 2,500, 3,000, 3,500, 4,000, 5,000, 6,000, 7,000, 8,000, 9,000, 10,000, 20,000 or greater than 20,000 bases. Some libraries consistent with the disclosure herein comprise a plurality of fragments that comprise both a repetitive region border and border-adjacent sequence, such that said plurality of fragments exhibit a mean fragment size of 50, 100, 200, 300, 400, 500, 600, 700, 800, 900, 1,000, 1,500, 2,000, 2,500, 3,000, 3,500, 4,000, 5,000, 6,000, 7,000, 8,000, 9,000, 10,000, 20,000 or greater than 20,000 bases. Some libraries consistent with the disclosure herein comprise a plurality of fragments that comprise both a repetitive region border and border-adjacent sequence, such that said plurality of fragments exhibit a median fragment size of 50, 100, 200, 300, 400, 500, 600, 700, 800, 900, 1,000, 1,500, 2,000, 2,500, 3,000, 3,500, 4,000, 5,000, 6,000, 7,000, 8,000, 9,000, 10,000, 20,000 or greater than 20,000 bases.

Libraries as disclosed herein comprise RNA or DNA. Some libraries arise from RNA transcription directed by an RNA polymerase promoter that is inserted, such as selectively inserted, into a mobile element or other repetitive region in a nucleic acid sample such as a genomic DNA sample. Some libraries comprise molecules generated from this transcription, including molecules optionally comprising RNA polymerase promoter sequence, repetitive region such as mobile element sequence, and mobile element or other repetitive region adjacent sequence such as adjacent genomic sequence. Some libraries comprise said RNA arising from RNA transcription directed by an inserted RNA polymerase promoter. Alternately, many libraries comprise DNA generated through revers transcription of a population of RNA molecules generated as described above.

Libraries as disclosed herein are generated from templates such as genomic nucleic acid samples, and are reflective of genomic sequence adjacent to repetitive regions in the samples. In some embodiments, the repetitive elements comprise mobile elements such as Alu repeats or transposons that are observed to relocate to various positions throughout a genome. This relocation or transposition is often specific to a cell or population of cells in an organism from which a genomic sample is derived. Alternatively, libraries are reflective of genomic sequence adjacent to a selected genomic region. Libraries are derived from samples such as genomic DNA samples from a population of cells such as tumor cells or healthy cells. In some cases a library is generated from a genomic DNA derived from a single cell.

In particular, some mobile element insertion events or transposition events are implicated in lineage-specific cell defects, such as cell cycle or cell growth regulatory defects as are often implicated in cancer cell lines. To facilitate identification of mobile element insertion events that are implicated in cancer, libraries are generated from templates such as genomic nucleic acid samples obtained from cancer or tumor cells or tissues, either alone or in combination with generation of libraries from noncancerous cells or tissues.

Libraries consistent with the disclosure herein are optionally sequenced so as to determine sequence adjacent to a repetitive or repeated region, such as a mobile element border or repeat adjacent sequence of a repetitive locus such as the HLA locus. Alternatively, libraries consistent with the disclosure herein are optionally sequenced as to determine sequence adjacent to a selected genomic region. Library constituents are sequenced using any number of sequencing approaches disclosed elsewhere herein or otherwise known to one of skill in the art, such as shotgun sequencing, next generation sequencing by synthesis approaches, long molecule sequencing such as PacBio, BioNano or Oxford Nanopore sequencing.

A sequence database generated hereby comprises nucleic acid sequences of a library consistent with the disclosure herein or practice of a method consistent with the disclosure herein. In some cases 10%, 20%, 30%, 40%, 50%, 60%, 70%, 80%, 85%, 90%, 91%, 92%, 93%, 94%, 95%, 96%, 97%, 98%, 99%, or more than 99%, such as 99.5%, 99.6%, 99.7%, 99.8%, 99.9%, about 100%, or 100% of the database constituents comprise both a repeat element such as a mobile element sequence and border-adjacent sequence.

In databases consistent with the disclosure herein, sequence in proximity to a mobile element border represents a greater proportion of the overall sequence of the library than in a related sample such as a genomic sample from which the library is generated. In some cases 10%, 20%, 30%, 40%, 50%, 60%, 70%, 80%, 85%, 90%, 91%, 92%, 93%, 94%, 95%, 96%, 97%, 98%, 99%, or more than 99%, such as 99.5%, 99.6%, 99.7%, 99.8%, 99.9%, about 100%, or 100% of the database constituents comprise sequence in proximity to a repeat element such as a mobile element border.

Databases consistent with the disclosure comprise sequences that comprise both a repetitive region border and border-adjacent sequence and that span at least 50, 100, 200, 300, 400, 500, 600, 700, 800, 900, 1,000, 1,500, 2,000, 2,500, 3,000, 3,500, 4,000, 5,000, 6,000, 7,000, 8,000, 9,000, 10,000, 20,000 or greater than 20,000 bases. Some databases consistent with the disclosure herein comprise a plurality of sequences that comprise both a repetitive region border and border-adjacent sequence, such that said plurality of sequences exhibit a mean sequence length of 50, 100, 200, 300, 400, 500, 600, 700, 800, 900, 1,000, 1,500, 2,000, 2,500, 3,000, 3,500, 4,000, 5,000, 6,000, 7,000, 8,000, 9,000, 10,000, 20,000 or greater than 20,000 bases. Some databases consistent with the disclosure herein comprise a plurality of sequences that comprise both a repetitive region border and border-adjacent sequence, such that said plurality of fragments exhibit a median fragment size of 50, 100, 200, 300, 400, 500, 600, 700, 800, 900, 1,000, 1,500, 2,000, 2,500, 3,000, 3,500, 4,000, 5,000, 6,000, 7,000, 8,000, 9,000, 10,000, 20,000 or greater than 20,000 bases.

Databases as disclosed herein are in some cases completely sequenced, such that database entries comprise end-to-end sequence information for library molecules from which they are generated. Alternately, in some cases some or all of a database's entries comprise paired reads, such that one member of a paired read comprises repeat element sequence such as mobile element sequence, while the other member of a paired read comprises repeat adjacent sequence, such that in some cases a mobile element border location is inferred without actually sequencing across the border of the mobile element.

Sequencing of Linearly Amplified Nucleic Acids

Methods disclosed herein optionally comprise sequencing the linearly amplified nucleic acids, such as those generated pursuant to the production of libraries as disclosed herein. In some cases, the methods comprise annealing an oligonucleotide or a hairpin oligonucleotide required for sequencing to the linearly amplified nucleic acids. In some cases, the sequencing comprises ligating an oligonucleotide or a hairpin oligonucleotide required for sequencing to the linearly amplified nucleic acids. In some cases, the methods comprise utilizing the adapter sequence or portion thereof to sequence the linearly amplified nucleic acids.

Various methods of nucleic acid sequencing are well-known and described in the art. The methods disclosed herein are consistent with a wide range of sequencing technologies.

Determination of the sequence of an linearly amplified nucleic acid is contemplated herein to be performed using a sequencing method selected from a variety of sequencing methods including, but not limited to, ion detection technology, DNA nanoball technology, nanopore-based sequencing technology, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. Optionally, high-throughput sequencing methods such as cyclic array sequencing using platforms such as Roche 454, Illumina Solexa, ABI-SOLiD, ION Torrents, Complete Genomics, Pacific Bioscience, Helicos, Polonator platforms, are utilized.

Determination of the sequence of a linearly amplified nucleic acid is optionally contemplated to be performed by a next-generation sequencing (NGS) method. NGS applies to genome sequencing, genome resequencing, transcriptome profiling (RNA-Seq), DNA-protein interactions (ChIP-sequencing), and epigenome characterization. Contemplated methods disclosed herein comprise NGS methods selected from, but are not limited to, massively parallel signature sequencing (MPSS), Polony sequencing, 454 pyrosequencing, Ion Torrent semiconductor sequencing, Heliscope single molecule sequencing, single molecule real time (SMRT) sequencing and microfluidic Sanger sequencing.

Mapping of Genomic Elements

Methods disclosed herein are optionally contemplated to comprise mapping a genomic element, for example a mobile genetic element using the sequences obtained from the methods provided herein. Alternately, the method comprises insertion of a tag, such as a nucleic acid tag, comprising a promoter, such as a T7 promoter, into the genomic element using genomic DNA editing technology, such as CRISPR. Additionally, the method comprises insertion of a hairpin tag, such as a hairpin nucleic acid tag, comprising a double stranded promoter, such as a T7 promoter, into the genomic element using genomic DNA editing technology, such as CRISPR. An RNA molecule is transcribed, from the inserted hairpin tag allowing for linear amplification of RNA having the same sequence as the DNA adjacent to the genomic element. An RNA molecule is transcribed, from the inserted tag allowing for linear amplification of RNA having the same sequence as the DNA adjacent to the genomic element. The sequence obtained from the linearly amplified nucleic acid allows one to find the corresponding location by comparing the sequence obtained to the sequence available for the reference genome, for example a human genome sequence, in the genome and thereby map the insertion of the genomic element. Optionally, the insertion of the genomic element maps to the coding sequence of a gene. Alternately, the insertion of the genomic element maps to an intron of a gene. It is also contemplated that the insertion of the genomic element maps to a promoter or enhancer sequence of a gene. Optionally, the insertion of the genomic element maps to a 5' or 3' untranslated region of a gene.

Insertion of a genomic element, for example a mobile genetic element near or into a gene, for example in the coding sequence, in an intron, into a promoter or enhancer, or into a 5' or 3' untranslated region, often causes disruption of the function of the gene. Disruption of gene function by insertion of a genetic element, for example a mobile genetic element, can occur by any one of a number of mechanisms known to one of skill in the art. Often, gene function is disrupted by insertion into the coding sequence, thereby disrupting or otherwise changing the amino acid sequence of the gene. Alternately, gene function is disrupted by insertion into an intron or 5' or 3' untranslated region, thereby affecting gene expression downstream of transcription, for example RNA splicing, RNA transport, and RNA translation. Optionally, gene function is disrupted by insertion into a promoter or enhancer element, thereby affecting assembly of gene regulatory proteins onto the chromatin and transcription of the gene.

Insertion of a genomic element and thereby disruption of function of one or more genes, often is a cause of disease. Optionally, the disease is a cancer. Alternatively, the disease is aging. It is contemplated herein that mapping the insertion of a genomic element informs a health care provider information, for example diagnostic information, that assists the healthcare provider in making decisions regarding treatment of the individual. Optionally, mapping the insertion of a genetic element provides a diagnosis for cancer. Alternatively, mapping the insertion of a genomic element provides a diagnosis for aging.

In some cases, provided herein are methods of diagnosing cancer in a subject, comprising obtaining a sample from the subject, isolating genomic DNA from the sample, contacting the genomic DNA with a composition that inserts a tag polynucleotide comprising a T7 promoter into a genomic element of the genomic DNA sample, performing in vitro transcription with a T7 RNA polymerase to obtain an RNA sample that has been linearly amplified from the genomic DNA, treating the sample with DNase to remove the genomic DNA from the sample, polyadenylating the RNA sample and reverse transcribing the RNA sample to obtain a cDNA, treating the sample with RNaseH to remove the RNA from the sample, and subjecting the resulting cDNA sample to DNA sequencing using a Next generation sequencing method resulting in a sequence that is adjacent to the genomic element. The sequence that is adjacent to the genomic element searched in a bioinformatics database such as BLAST to determine the location of the insertion of the genomic element and thereby determine the identity of any genes near the insertion.

Sequencing Challenging Genomic Regions

Provided herein are methods of sequencing regions of the genome that pose difficulties or challenges in sequencing using conventional sequencing methods, i.e. difficult to sequence polynucleotides. In some cases, difficult to sequence polynucleotides comprise low-complexity polynucleotides, repetitive polynucleotides, di-nucleotide repeat polynucleotides, tri-nucleotide repeat polynucleotides, GC-rich polynucleotides, polynucleotides with secondary structure, polynucleotides with 5'-YGN1-2AR motifs, and combinations thereof In some cases, the difficult to sequence polynucleotide comprises a trinucleotide repeat, such as a CAG repeat, a CGG repeat, a GCC repeat, a GAA repeat, or a CTG repeat. In some cases, the difficult to sequence polynucleotide comprises a gene that is difficult to sequence such as an HLA gene, including an HLA-A gene, an HLA-B gene, an HLA-C gene, an HLA-E gene, an HLA-F gene, an HLA-G gene, an HLA-DP gene, an HLA-DQ gene, or an HLA-DR gene.

In some cases, obtaining the sequence of a gene that is difficult to sequence, such as an HLA gene, allows a healthcare provider to obtain a genotype of the patient at that genomic locus, for example an HLA genotype or an HLA-type. In some cases, an HLA-type is helpful in determining compatibility for an organ or tissue transplant, for example a bone marrow transplant, heart transplant, lung transplant, liver transplant, kidney transplant, pancreas transplant, intestine transplant, thymus transplant, cornea transplant, skin transplant, heart valve transplant, nerve transplant, or vein transplant.

Alternately, nucleic acid molecules that pose sequencing challenges include CYP2D6 genes and homologues thereof. Additionally, VDJ regions of immunoglobulin genes pose sequencing challenges. Methods herein are helpful in sequencing these genes and genomic regions Definitions A partial list of relevant definitions is as follows.

"Amplified nucleic acid" or "amplified polynucleotide" includes any nucleic acid or polynucleotide molecule whose amount has been increased by any nucleic acid amplification or replication method performed in vitro as compared to its starting amount. For example, an amplified nucleic acid is optionally obtained from a polymerase chain reaction (PCR) which can, in some instances, amplify DNA in an exponential manner (for example, amplification to $2^n$ copies in n cycles) wherein most products are generated from intermediate templates rather than directly from the sample template. Amplified nucleic acid is alternatively obtained from a linear amplification, where the amount increases linearly over time and which, in some cases, produces products that are synthesized directly from the sample.

"Amplification product" refers to a product resulting from an amplification reaction such as a polymerase chain reaction or a linear amplification.

An "amplicon" is a polynucleotide or nucleic acid that is the source and/or product of natural or artificial amplification or replication events.

The term "biological sample" or "sample" generally refers to a sample or part isolated from a biological entity. The biological sample, in some cases, shows the nature of the whole biological entity and examples include, without limitation, bodily fluids, dissociated tumor specimens, cultured cells, and any combination thereof. Biological samples come from one or more individuals. One or more biological samples come from the same individual. In one non limiting example, a first sample is obtained from an individual's blood and a second sample is obtained from an individual's tumor biopsy. Examples of biological samples include but are not limited to, blood, serum, plasma, nasal swab or nasopharyngeal wash, saliva, urine, gastric fluid, spinal fluid, tears, stool, mucus, sweat, earwax, oil, glandular secretion, cerebral spinal fluid, tissue, semen, vaginal fluid, interstitial fluids, including interstitial fluids derived from tumor tissue, ocular fluids, spinal fluid, throat swab, breath, hair, finger nails, skin, biopsy, placental fluid, amniotic fluid, cord blood, emphatic fluids, cavity fluids, sputum, pus, microbiota, meconium, breast milk and/or other excretions. In some cases, a blood sample comprises circulating tumor cells or cell free DNA, such as tumor DNA or fetal DNA. The samples include nasopharyngeal wash. Examples of tissue samples of the subject include but are not limited to, connective tissue, muscle tissue, nervous tissue, epithelial tissue, cartilage, cancerous or tumor sample, or bone. Samples are obtained from a human or an animal. Samples are obtained from a mammal, including vertebrates, such as murines, simians, humans, farm animals, sport animals, or pets. Samples are obtained from a living or dead subject. Samples are obtained fresh from a subject or have undergone some form of pre-processing, storage, or transport.

Nucleic acid sample as used herein refers to a nucleic acid sample for which sequence information is to be determined, A nucleic acid sample is extracted from a biological sample above, in some cases. Alternatively, a nucleic acid sample is artificially synthesized, synthetic, or de novo synthesized in some cases. The DNA sample is genomic in some cases, while in alternate cases the DNA sample is derived from a reverse-transcribed RNA sample.

"Bodily fluid" generally describes a fluid or secretion originating from the body of a subject. In some instances, bodily fluid is a mixture of more than one type of bodily fluid mixed together. Some non-limiting examples of bodily fluids include but are not limited to: blood, urine, bone marrow, spinal fluid, pleural fluid, lymphatic fluid, amniotic fluid, ascites, sputum, or a combination thereof.

"Complementary" or "complementarity," or, in some cases more accurately "reverse-complementarity" refer to nucleic acid molecules that are related by base-pairing. Complementary nucleotides are, generally, A and T (or A and U), or C and G (or G and U). Functionally, two single stranded RNA or DNA molecules are complementary when they form a double-stranded molecule through hydrogen-bond mediated base paring. Two single stranded RNA or DNA molecules are said to be substantially complementary when the nucleotides of one strand, optimally aligned and with appropriate nucleotide insertions or deletions, pair with at least about 90% to about 95% or greater complementarity, and more preferably from about 98% to about 100%) complementarity, and even more preferably with 100% complementarity. Alternatively, substantial complementarity exists when an RNA or DNA strand will hybridize under selective hybridization conditions to its complement. Selective hybridization conditions include, but are not limited to, stringent hybridization conditions and not stringent hybridization conditions. Hybridization temperatures are generally at least about 2° C. to about 6° C. lower than melting temperatures ($T_m$).

A "barcode" or "molecular barcode" includes a material for labeling. The barcode labels a molecule such as a nucleic acid or a polypeptide. The material for labeling is associated with information. A barcode in some instances is called a sequence identifier (for example, a sequence-based barcode or sequence index). In some cases, a barcode comprises a particular nucleotide sequence. A barcode is used as an identifier. A barcode is alternatively a different size molecule or different ending points of the same molecule. Barcodes include a specific sequence within the molecule and a different ending sequence. For example, a molecule that is amplified from the same primer and has 25 nucleotide positions is different than a molecule that is amplified and has 27 nucleotide positions. The additional positions in the 27mer sequence are optionally considered a barcode. A barcode is alternatively incorporated into a polynucleotide. A barcode is, in some cases, incorporated into a polynucleotide by many methods. Some non-limiting methods for incorporating a barcode include molecular biology methods. Some non-limiting examples of molecular biology methods to incorporate a barcode are through primers (e.g., tailed primer elongation), probes (i.e., elongation with ligation to a probe), or ligation (i.e., ligation of known sequence to a molecule). In some cases, a barcode is biotinylated. A biotinylated barcode is optionally used as a means of purification. Purification of biotinylated molecules is accomplished through methods including but not limited to immunoprecipitation. In some cases, biotin is added at the target site and the sample DNA is sheared or otherwise cleaved, for example by endonucleases, yielding a sample sequence optionally at least 10 kilobases in length.

A barcode is variously incorporated into any region of a guide RNA or polynucleotide. In some cases, the region where the barcode is incorporated is known. Alternatively, the region is unknown. The barcode is contemplated to be added to any position along the guide RNA. In some cases barcode is added to the 5' end of a guide RNA. Alternatively, barcode is added to the 3' end of the guide RNA. In some cases, the barcode is added in between the 5' and 3' end of a guide RNA. A barcode is contemplated to be added with one or more other known sequences. One non-limiting example is the addition of a barcode with a sequence adapter.

Barcodes are contemplated to be associated with information. Some non-limiting examples of the type of information a barcode are associated with information include: the source of a sample; the orientation of a sample; the region or container a sample was processed in; the adjacent polynucleotide; or any combination thereof.

In some cases, barcodes are made from combinations of sequences (different from combinatorial barcoding) and are used to identify a sample or a genomic coordinate and a different template molecule or single strand the molecular label and copy of the strand was obtained from. In some cases a sample identifier, a genomic coordinate and a specific label for each biological molecule are amplified together. Barcodes, synthetic codes, or label information are obtained from the sequence context of the code (allowing for errors or error correcting), the length of the code, the orientation of the code, the position of the code within the molecule, and in combination with other natural or synthetic codes.

In some cases, incorporation of a barcode into a nucleic acid molecule indicates that the nucleic acid was present in a given sample at a given time period. In some cases, contiguous adjacent nucleic acid sequence sharing a common barcode or a common bar code pair is inferred to have been derived from a common molecule, particularly if the sample is diluted to less than an average of 2x, 1.5x, 1x, 0.7x, 0.5, or 0.3x haploid genomes prior to barcode introduction.

Barcodes are contemplated herein to be added before pooling of samples. When the sequences of the pooled samples are determined, the barcode is sequenced along with the rest of the polynucleotide. The barcode is optionally used to associate the sequenced fragment with the source of the sample.

Barcodes are alternatively used to identify the strandedness sample. In some cases, one or more barcodes are used together. Two or more barcodes are alternatively adjacent to one another, not adjacent to one another, or any combination thereof. Adapter orientation is often used to determine strandedness. For example, if an "A" adapter is always in the 5'-3' direction in a first primer extension reaction, then one infers the read starting from the A adapter would be the compliment of the strand that was initially primed.

Barcodes are contemplated herein for use in combinatorial labeling.

As indicated herein, standard single-letter amino acid residue abbreviations as known in the art are used to refer to the twenty amino acids involved in cellular ribosomally driven polypeptide synthesis.

"Combinatorial labeling" is a method herein by which two or more barcodes are used to label a molecule. The two or more barcodes label a polynucleotide. The barcodes, each, alone in some cases are associated with information. Alternatively, the combination of the barcodes together is associated with information. In some cases a combination of barcodes is used together to determine in a randomly amplified molecule that the amplification occurred from the original sample template and not a synthetic copy of that template. In some cases, the length of one barcode in combination with the sequence of another barcode is used to label a polynucleotide. In some cases, the length of one barcode in combination with the orientation of another barcode is used to label a polynucleotide. In other cases, the sequence of one barcode is used with the orientation of another barcode to label a polynucleotide. In some cases the sequence of a first and a second bar code, in combination with the distance in nucleotides between them, is used to label or to identify a polynucleotide. In some cases the sequence of a first and a second bar code, in combination with the distance in nucleotides between them and the identity of the nucleotides between them, is used to label or to identify a polynucleotide.

"Degenerate" refers to a nucleic acid or nucleic acid region that is comprised of random bases. The terms "degenerate" and "random" are used interchangeably when referring to nucleic acid sequences (e.g., "degenerate primers" or "random primers" or "degenerate probes" or "random probes"). The degenerate region is of variable length. In some cases, the degenerate region comprises some portion of the whole nucleic acid (e.g., a semi-degenerate primer). Alternatively, the degenerate region comprises the whole nucleic acid (e.g., a "degenerate primer"). A degenerate nucleic acid mix, or semi-degenerate nucleic acid mix is comprised of every possible combination of base pairs, less than every possible combination of base pairs, or some combination of base pairs, a few combinations of base pairs, or a single base pair combination. A degenerate primer mix, or semi-degenerate primer mix comprises mixes of similar but not identical primers.

"Double-stranded" refers, in some cases, to two polynucleotide strands that have annealed through complementary base-pairing, such as in a reverse-complementary orientation.

"Known oligonucleotide sequence" or "known oligonucleotide" or "known sequence" refers to a polynucleotide sequence that is known. In some cases, a known oligonucleotide sequence corresponds to an oligonucleotide that has been designed, e.g., a universal primer for next generation sequencing platforms (e.g., Illumina, 454), a probe, an adaptor, a tag, a primer, a molecular barcode sequence, an identifier. A known sequence optionally comprises part of a primer. A known oligonucleotide sequence, in some cases, is not actually known by a particular user but is constructively known, for example, by being stored as data accessible by a computer. A known sequence is optionally a trade secret that is actually unknown or a secret to one or more users but is known by the entity who has designed a particular component of the experiment, kit, apparatus or software that the user is using.

"Library" in some cases refers to a collection of nucleic acids. A library optionally contains one or more target fragments. In some instances the target fragments comprise amplified nucleic acids. In other instances, the target fragments comprise nucleic acid that is not amplified. A library optionally contains nucleic acid that has one or more known oligonucleotide sequence(s) added to the 3' end, the 5' end or both the 3' and 5' end. The library is optionally prepared so that the fragments contain a known oligonucleotide sequence that identifies the source of the library (e.g., a molecular identification barcode identifying a patient or DNA source). In some instances, two or more libraries are pooled to create a library pool. Libraries are optionally generated with other kits and techniques such as transposon mediated labeling, or "tagmentation" as known in the art. Kits are commercially available. One non-limiting example of a kit is the Illumina NEXTERA kit (Illumina, San Diego, Calif.).

"Locus specific" or "loci specific" in some cases refers to one or more loci corresponding to a location in a nucleic acid molecule (e.g., a location within a chromosome or genome). In some instances, a locus is associated with genotype. In some instances loci are directly isolated and enriched from the sample, e.g., based on hybridization and/or other sequence-based techniques, or alternatively they may are selectively amplified using the sample as a template prior to detection of the sequence. In some instances, loci are selected on the basis of DNA level variation between individuals, based upon specificity for a particular chromosome, based on CG content and/or required amplification conditions of the selected loci, or other characteristics that will be apparent to one skilled in the art upon reading the present disclosure. A locus optionally refers to a specific genomic coordinate or location in a genome as denoted by the reference sequence of that genome.

"Long nucleic acid" refers, in some cases, to a polynucleotide longer than 1, 2, 3, 4, 5, 6, 7, 8, 9, or 10 kilobases.

The term "melting temperature" or "$T_m$" commonly refers to the temperature at which a population of double-stranded nucleic acid molecules becomes half dissociated into single strands. Equations for calculating the $T_m$ of nucleic acids are well known in the art. One equation that gives a simple estimate of the $T_m$ value is as follows: $T_m$=81.5+16.6(log 10[$Na^+$])0.41(%[G+C])−675/n−1.0 m, when a nucleic acid is in aqueous solution having cation concentrations of 0.5 M or less, the (G+C) content is between 30% and 70%, n is the number of bases, and m is the percentage of base pair mismatches (see, e.g., Sambrook J et al., *Molecular Cloning, A Laboratory Manual,* 3rd Ed., Cold Spring Harbor Laboratory Press (2001)). Other references include more sophisticated computations, which take structural as well as sequence characteristics into account for the calculation of $T_m$.

"Nucleotide" refers to a base-sugar-phosphate combination. Nucleotides are monomeric units of a nucleic acid sequence (e.g., DNA and RNA). The term nucleotide includes naturally and non-naturally occurring ribonucleoside triphosphates ATP, TTP, UTP, CTG, GTP, and ITP, for example and deoxyribonucleoside triphosphates such as dATP, dCTP, dITP, dUTP, dGTP, dTTP, or derivatives thereof. Such derivatives include, for example, [aS]dATP, 7-deaza-dGTP and 7-deaza-dATP, and, for example, nucleotide derivatives that confer nuclease resistance on the nucleic acid molecule containing them. The term nucleotide as used herein also refers to dideoxyribonucleoside triphosphates (ddNTPs) and their derivatives. Illustrative examples of dideoxyribonucleoside triphosphates include, ddATP, ddCTP, ddGTP, ddITP, ddUTP and ddTTP, for example.

"Polymerase" refers to an enzyme that links individual nucleotides together into a strand, using another strand as a template.

"Polymerase chain reaction" or "PCR" refers to a technique for replicating a specific piece of selected DNA in vitro, even in the presence of excess non-specific DNA. Primers are added to the selected DNA, where the primers initiate the copying of the selected DNA using nucleotides and, typically, Taq polymerase or the like. By cycling the temperature, the selected DNA is repetitively denatured and copied. A single copy of the selected DNA, even if mixed in with other, random DNA, in some cases, is amplified to obtain thousands, millions, or billions of replicates. The polymerase chain reaction is used to detect and measure very small amounts of DNA and to create customized pieces of DNA.

The term "polynucleotides" or "nucleic acids" includes but is not limited to various DNA, RNA molecules, derivatives or combination thereof. These include species such as dNTPs, ddNTPs, DNA, RNA, peptide nucleic acids, cDNA, dsDNA, ssDNA, plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA.

A "primer" generally refers to an oligonucleotide used to, e.g., prime nucleotide extension, ligation and/or synthesis, such as in the synthesis step of the polymerase chain reaction or in the primer extension techniques used in certain sequencing reactions. A primer is alternatively used in hybridization techniques as a means to provide complementarity of a locus to a capture oligonucleotide for detection of a specific nucleic acid region.

"Primer extension product" refers to the product resulting from a primer extension reaction using a contiguous polynucleotide as a template, and a complementary or partially complementary primer to the contiguous sequence.

"Sequencing," "sequence determination," and the like generally refers to any and all biochemical methods that may be used to determine the order of nucleotide bases in a nucleic acid.

A "contig" refers to a nucleotide sequence that is assembled from two or more constituent nucleotide sequences that share common or overlapping regions of sequence homology. For example, the nucleotide sequences of two or more nucleic acid fragments are compared and aligned in order to identify common or overlapping sequences. Where common or overlapping sequences exist between two or more nucleic acid fragments, the sequences (and thus their corresponding nucleic acid fragments) are assembled into a single contiguous nucleotide sequence.

The term "biotin," as used herein, is intended to refer to biotin (5-[(3aS,4S,6aR)-2-oxohexahydro-1H-thieno[3,4-d] imidazol-4-yl]pentanoic acid) and any biotin derivatives and analogs. Such derivatives and analogs are substances which form a complex with the biotin binding pocket of native or modified streptavidin or avidin. Such compounds include, for example, iminobiotin, desthiobiotin and streptavidin affinity peptides, and also include biotin-.epsilon.-N-lysine, biocytin hydrazide, amino or sulfhydryl derivatives of 2-iminobiotin and biotinyl-E-aminocaproic acid-N-hydroxysuccinimide ester, sulfo-succinimide-iminobiotin, biotin-bromoacetylhydrazide, p-diazobenzoyl biocytin, 3-(N-maleimidopropionyl) biocytin. "Streptavidin" refers to a protein or peptide that binds to biotin and includes but is not limited to native egg-white avidin, recombinant avidin, deglycosylated forms of avidin, bacterial streptavidin, recombinant streptavidin, truncated streptavidin, and/or any derivative thereof.

A "subject" as used herein is a source of nucleic acid and in some cases refers to an organism that is currently living or an organism that at one time was living or an entity, optionally with a genome that replicates. The methods, kits, and/or compositions of the disclosure are contemplated herein to be applied to one or more single-celled or multi-cellular subjects, including but not limited to microorganisms such as bacterium and yeast; and animals including, but not limited to: humans; laboratory animals such as mice, rats, monkeys, and chimpanzees; domestic animals such as dogs and cats, and agricultural animals such as cows, horses, pigs, sheep, and goats. The methods of this disclosure are in some cases applied to germs or infectious agents, such as viruses or virus particles or one or more cells that have been infected by one or more viruses. In some cases, the subject is a fully synthetic organism.

A "support" is contemplated herein to be solid, semisolid, a bead, a surface. The support is optionally mobile in a solution or immobilized.

The term "unique identifier" includes but is not limited to a molecular bar code, or a percentage of a nucleic acid in a mix, such as dUTP.

"Repetitive sequence" as used herein refers to sequence that does not uniquely map to a single position in a nucleic acid sequence data set. Some repetitive sequence is optionally conceptualized as integer or fractional multiples of a repeating unit of a given size and exact or approximate sequence.

A "palindrome" or "palindromic sequence" as used herein refers to a nucleic acid sequence that is the same whether read 5' (five-prime) to 3' (three prime) on one strand or 5' to 3' on the complementary strand with which it forms a double helix.

An "inverted sequence" as used herein refers to a sequence that is the reverse sequence or reverse complement sequence relative to another sequence. A sequence is inverted if, upon (conceptually) rotating the molecule on which it is found by 180 degrees, the sequence as read in the same direction is the same sequence.

A "haplotype" as used herein refers to a collection of specific alleles in a cluster of tightly-linked genes on a chromosome that are likely to be inherited together.

A "sub-haplotype" as used herein refers to a subset of genes or portion of a haplotype.

The term "about" as used herein in reference to a number refers to that number plus or minus 10%.

The term "comprise" as used herein is inclusive, such that in the context of at least one element, it indicates that other unrecited elements may also be included.

As used herein, a repetitive or repeated region refers to a distinct genomic or other nucleic acid segment that recurs locally at a given locus or dispersed throughout a nucleic acid sample such as a genome sample. Exemplary repetitive segments include regions within the HLA locus, cyp2d6, VDJ regions and mobile elements such as Alu repeats and LINE elements.

Before the present methods, compositions and kits are described in greater detail, it is to be understood that this invention is not limited to particular method, composition or kit described, as such may, of course, vary. It is also to be understood that the terminology used herein is for the purpose of describing particular embodiments only, and is not intended to be limiting, since the scope of the present invention will be limited only by the appended claims as construed herein. Examples are put forth so as to provide those of ordinary skill in the art with a more complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein are optionally used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method is contemplated to be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

Turning to the figures, one sees the following:

FIG. 1 shows an exemplary human LINE1 (L1.4) repetitive element DNA sequence (SEQ ID NO: 1). PAM sequences 5'-3' in FIG. 1 are underlined.

FIG. 2 shows an exemplary consensus sequence of L1HA: Diagnostic sequence at 3' end of LINE-1 element (SEQ ID NO: 2). The PAM sequence is underlined. An example guide RNA complimentary sequence BOLD.

FIG. 3 shows an exemplary guide RNA sequence (SEQ ID NO: 3).

FIG. 4 shows an exemplary Alu-Y sequence (SEQ ID NO:4). Pam sequences are underlined in this figure.

FIG. 5 shows an exemplary CRISPR induced insertion of target specific T7 promoter sequences. High molecular weight double stranded genomic DNA is combined with CRISPR/CAS components including target specific guide RNA, CAS9 protein, donor DNA (including T7 promoter), and ligase. This figure shows that the T7 promoter is inserted specifically into target DNA sequence.

FIG. 6 shows an exemplary in vitro transcription of target DNA generates amplified RNA copies of the target template. RNA molecules are optionally fragmented and converted into short read sequencer libraries or poly A tailed and reverse transcribed into full length cDNA. This figure illustrates that full length cDNA molecules are converted into long read sequencer libraries.

Figure 7:
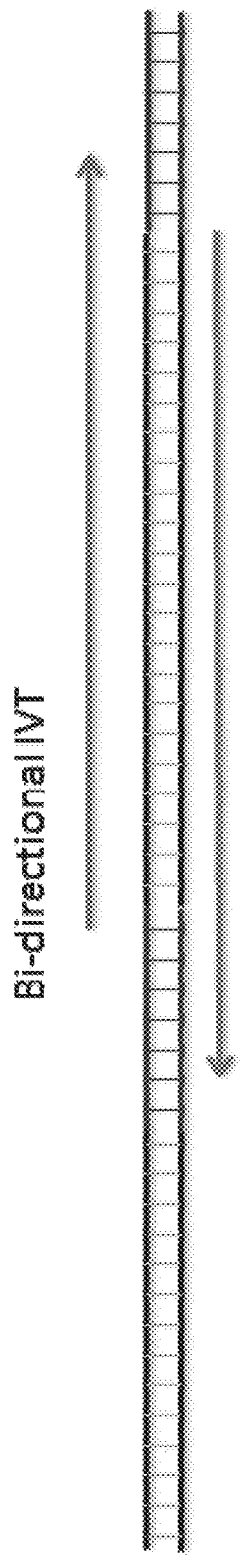
FIG. 7 shows T7 promoters specifically inserted upstream and downstream of target sequence.

FIG. 7 shows exemplary T7 promoters specifically inserted upstream and downstream of target sequence. In vitro transcription will occur in both directions covering target loci in excess of 10 kb.

Figure 8:
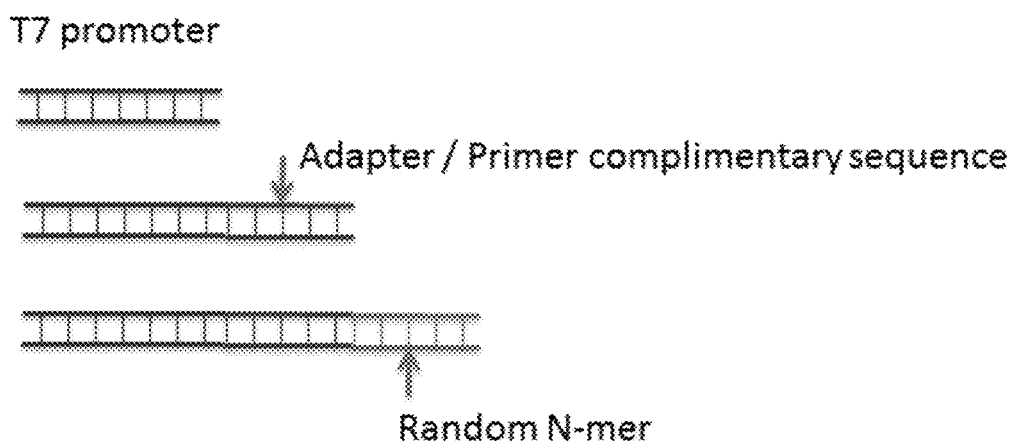
FIG. 8 shows alternative donor DNA constructs.

FIG. 8 shows alternative donor DNA constructs. These constructs may comprise promoter sequences such as a T7 promoter, adaptor/primer complementary sequences, and random sequences.

Figure 9:
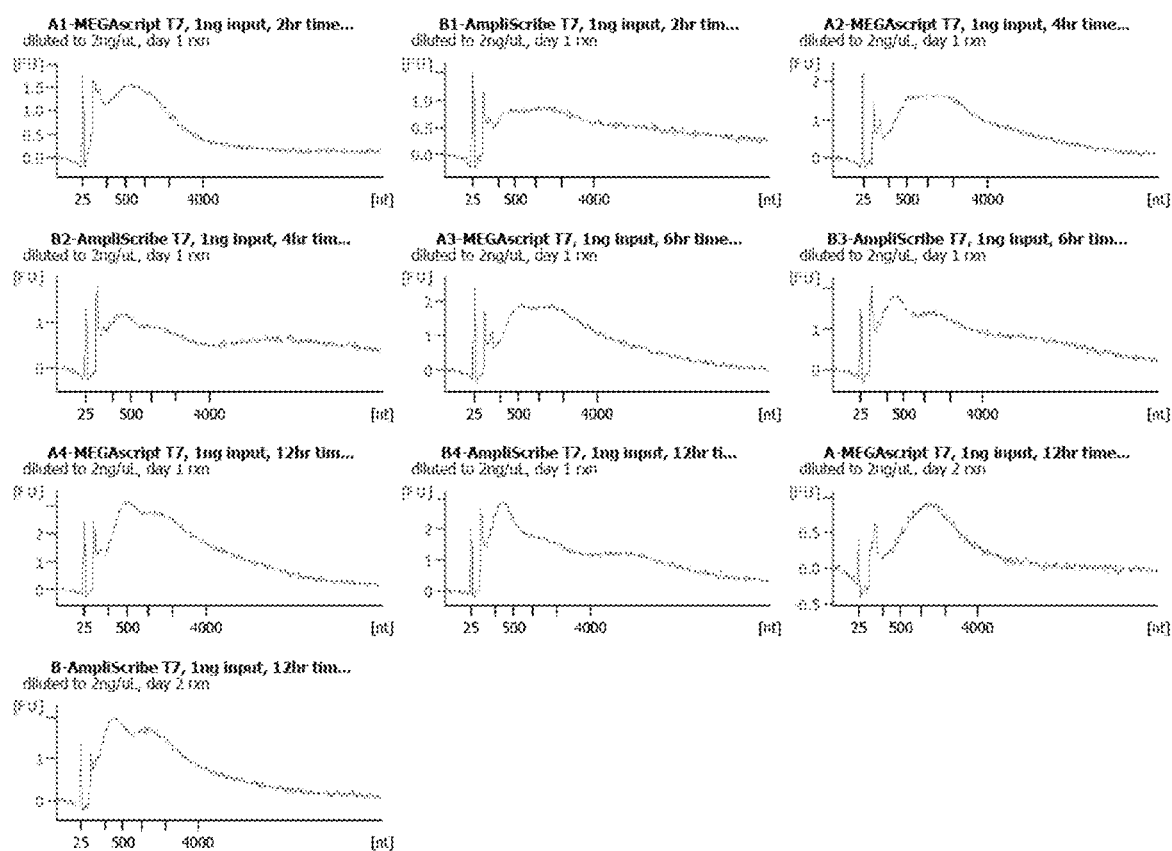
FIG. 9 shows results of linear amplification of genomic sequence adjacent to an inserted T7 RNA polymerase site in a sample.

FIG. 9 shows results of linear amplification of genomic sequence adjacent to an inserted T7 RNA polymerase site in a sample. Results are shown for two enzymes, run for 2, 4, 6, or 12 hours on 1 ng of template diluted to 2 ng/uL. For each result, the y-axis indicates fluorescence units, ranging from 0.0 to up to 1.0 or even in some cases 2.0. The x-axis represents library constituent length in nucleotides, on a logarithmic scale for which 25 ntm 500 nt and 4000 nt are labeled. The results indicate that libraries having a median constituent size of between 500 bases and 2 kb are routinely made through linear amplification directed by a RNA promoter inserted into a sample nucleic acid. In vitro transcription was performed for four separate time point intervals using MEGAscript and AmpliScribe T7 RNA polymerase kits. Reactions were run for 2, 4, 6, or 12 hour intervals. 1 ng of DNA was used per reaction. Reactions were incubated with DNAse for 1 hour subsequent to transcription. RNA was quantified using a Qubit High Sensitivity RNA Assay kit. RNA analysis was performed using a High Sensitivity Pico mRNA Bioanalyzer.

Figure 10:
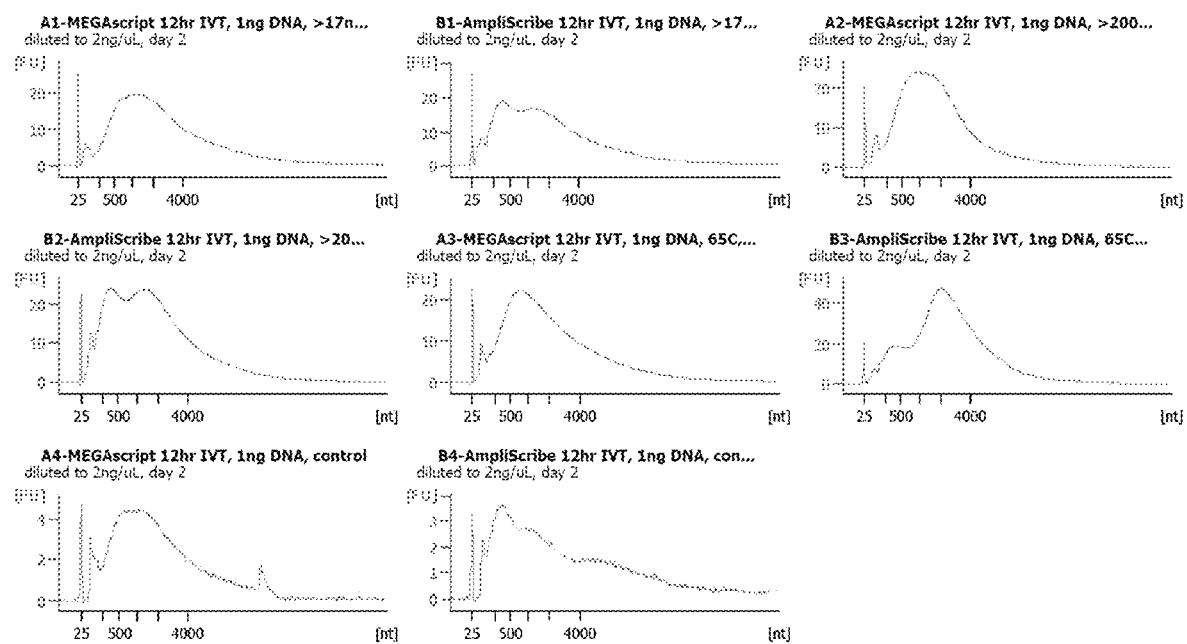
FIG. 10 shows additional results of linear amplification of genomic sequence adjacent to an inserted T7 RNA polymerase site.

Turning to FIG. 10, one sees the following. Bioanalyzer traces for size-selected RNA in vitro transcribed samples are presented. The x-axis indicates nucleotide length, [nt] on a logarithmic scale, with 25, 500 and 4000 nucleotides indicated. The y-axis indicates fluorescence units [FU]ranging from 0-20 in intervals of 10 (top and center file). 0-40 in intervals of 20 (center file, at right), or from 0-4 in intervals of 2 (bottom left) or 0-3 in intervals of 1 (bottom right). Results are presented for Ampliscribe and MEGAscript RNA polymerases. Samples were diluted to 2 ng/uL and run on day 2. The results indicate that in vitro transcribed samples are readily size selected to exclude smaller constituents.

Figure 11:
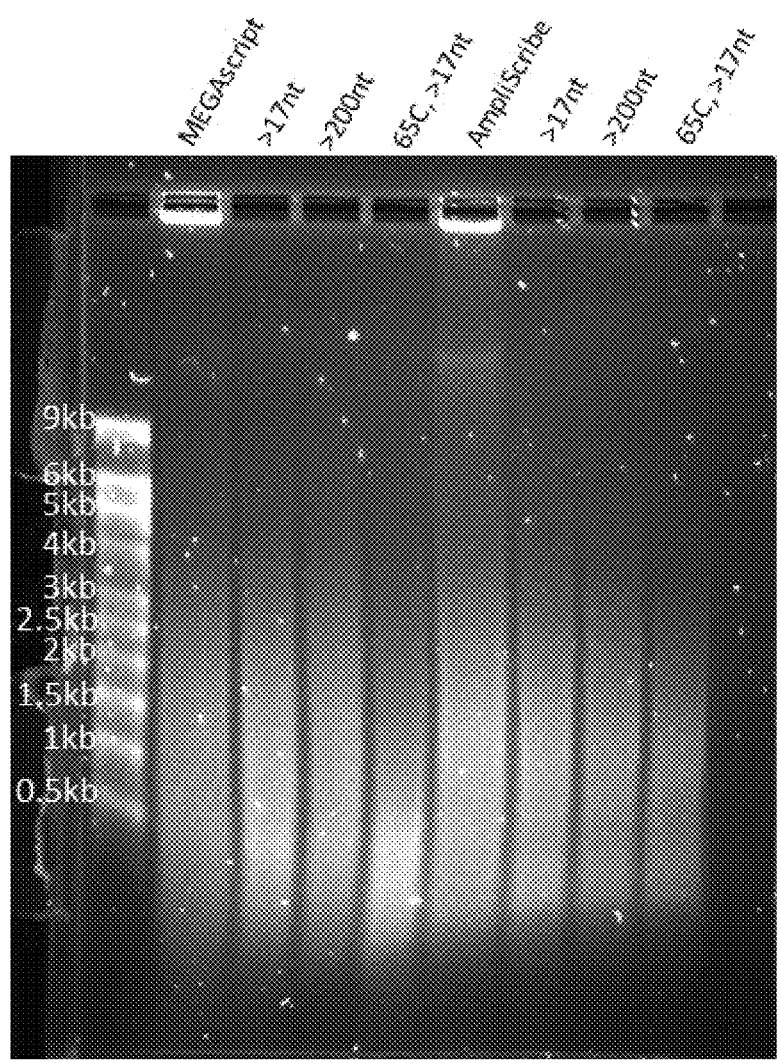
FIG. 11 shows an agarose gel of in vitro transcribed RNA.

Turning to FIG. 11, one sees the RNA of FIG. 10 run on a denaturing agarose gel. The ladder at right indicates sizes of 0.5, 1, 1.5, 2, 2.5, 3, 4, 5, 6, and 9 kb. Sample lanes are, from left, MEGAscript control, MEGAscript 17 nt exclusion, MEGAscript 200 nt exclusion, MEGAscript 65 C incubation plus 17 nt exclusion, followed by Ampliscribe control, Ampliscribe 17 nt exclusion, Ampliscribe 200 nt exclusion, and Ampliscribe 65 C incubation plus 17 nt exclusion. The results indicate that in vitro transcribed samples are readily size selected to exclude smaller constituents.

Turning to FIG. 12 one sees in the top panel a guide RNA and a CAS9 creating a double stranded break in a DNA target. In the middle panel a hairpin nucleic acid having a double stranded T7 promoter connected by a loop to a single stranded portion having reverse complementarity to the target DNA binds to the target sequence and is ligated. The hairpin nucleic acid is one continuous strand of DNA having a first reverse complementary strand of a T7 promoter, a loop, a second strand of a T7 promoter, and a portion having reverse complementarity to the target DNA. In solution, the hairpin nucleic acid folds on itself forming the hairpin as shown in the center panel. In the last panel in vitro transcription is used to create RNA copies of the target DNA locus.

Partial List of Numbered Embodiments

The disclosure herein is further clarified in reference to a partial list of numbered embodiments as follows. 1. A method of determining a sequence adjacent to a region of known sequence of a nucleic acid molecule, the method comprising a) attaching a nucleic acid fragment comprising promoter sequence at the known region of the nucleic acid molecule; b) contacting the nucleic acid fragment to an RNA polymerase directed by the promoter; and c) synthesizing a plurality of RNA molecules; wherein a consensus sequence of the plurality of RNA molecules represents the sequence adjacent to the known region of a nucleic acid molecule. 2. The method of embodiment 1, wherein the consensus sequence is at least 10 kilobases in length. 3. The method of any one of embodiments 1 or 2, comprising treating the nucleic acid molecule using a DNase subsequent to synthesizing the plurality of RNA molecules. 4. The method of any one of embodiments 1 to 3, comprising reverse-transcribing the plurality of RNA molecules. 5. The method of any one of embodiments 1 to 4, comprising determining nucleic acid sequences of the plurality of RNA molecules. 6. The method of any one of embodiments 1 to 5, wherein the consensus sequence of the plurality of RNA molecules comprises sequence of molecules synthesized directly from the nucleic acid molecule. 7. The method of any one of embodiments 1 to 6, wherein the attaching comprises inserting the nucleic acid fragment comprising promoter sequence at the known region of the nucleic acid molecule. 8. The method of any one of embodiments 1 to 7, wherein the attaching comprises inserting the nucleic acid fragment comprising promoter sequence at the region of known sequence of the nucleic acid molecule. 9. The method of any one of embodiments 1 to 8, wherein the attaching comprises sequence-specific cleavage of the region of known sequence of the nucleic acid molecule. 10. The method of any one of embodiments 1 to 9, wherein the attaching comprises contacting the known region of the nucleic acid molecule to a CRISPR nucleic acid-protein complex. 11. The method of embodiment 10, wherein the CRISPR nucleic acid-protein complex comprises a guide RNA comprising SEQ ID NO: 3. 12. The method of any one of embodiments 1 to 11, wherein the attaching comprises ligating the nucleic acid fragment comprising promoter sequence. 13. The method of any one of embodiments 1 to 12, wherein the nucleic acid fragment comprising promoter sequence comprises a viral promoter. 14. The method of embodiment 13, wherein the viral promoter binds a viral RNA polymerase and is at least one promoter selected from the list consisting of T7, T3, T7lac, SP6, pL, CMV, SV40, and CaMV35S. 15. The method of any one of embodiments 1 to 12, wherein the nucleic acid fragment comprising promoter sequence comprises a bacterial promoter. 16. The method of embodiment 15, wherein the bacterial promoter binds a bacterial RNA polymerase and is at least one promoter selected from the list consisting of araBAD, trp, lac, and Ptac. 17. The method of any one of embodiments 1 to 12, wherein the nucleic acid fragment comprising promoter sequence comprises a eukaryotic promoter. 18. The method of embodiment 17, wherein the eukaryotic promoter binds a eukaryotic RNA polymerase and is at least one promoter selected from the list consisting of EFla, PGK1, Ubc, beta actin, CAG, TRE, UAS, Ac5, Polyhedrin, CaMKIIa, ALB, GAL1, GAL10, TEF1, GDS, ADH1, Ubi, H1, and U6. 19. The method of embodiment 17, wherein the eukaryotic promoter is at least one promoter selected from the list consisting of an RNA pol I promoter, an RNA pol II promoter and an RNA pol III promoter. 20. The method of any one of embodiments 1 to 19, wherein the known region of a nucleic acid molecule comprises a repetitive element. 21. The method of embodiment 20, wherein the repetitive element comprises a mobile insertion element. 22. The method of embodiment 20, wherein the repetitive element comprises at least one of a LINE element, a SINE element, an Alu repeat, a transposon, a retrotransposon, a centromeric repeat, and a telomeric repeat. 23. The method of embodiment 20, wherein the LINE element comprises SEQ ID NO: 1. 24. A method of determining a plurality of locus-adjacent sequences of an element in a nucleic acid sample, comprising the steps of a) inserting a nucleic acid comprising a promoter into the element, b) generating a plurality of nucleic acid molecules directed by the promoter, and c) determining the sequence of the plurality of nucleic acid molecules, wherein the nucleic acid molecules are synthesized directly from the nucleic acid sample and wherein the plurality of nucleic acid molecules span locus adjacent sequences. 25. The method of embodiment 24, wherein the nucleic acid molecules comprise RNA. 26. The method of embodiment 24, wherein the nucleic acid molecules cannot prime nucleic acid synthesis. 27. The method of embodiment 24, wherein the nucleic acid sample comprises cancer cell nucleic acids. 28. The method of embodiment 24, wherein the nucleic acid sample comprises a single nuclear genome. 29. The method of embodiment 24, wherein the nucleic acid sample is obtained from a single cell. 30. The method of embodiment 24, comprising treating the nucleic acid sample using a DNase subsequent to synthesizing the plurality of RNA molecules. 31. The method of embodiment 24, comprising reverse-transcribing the plurality of RNA molecules. 32. The method of embodiment 24, wherein the plurality of nucleic acid molecules are RNA molecules. 33. The method of embodiment 24, wherein the consensus sequence of the plurality of RNA molecules comprises sequence of molecules synthesized directly from the nucleic acid molecule. 34. The method of embodiment 24, wherein the attaching comprises inserting the nucleic acid fragment comprising promoter sequence at the known region of the nucleic acid molecule. 35. The method of embodiment 24, wherein the attaching comprises inserting the nucleic acid fragment comprising promoter sequence at the known region of the nucleic acid molecule. 36. The method of embodiment 24, wherein the attaching comprises sequence-specific cleavage of the known region of the nucleic acid molecule. 37. The method of embodiment 24, wherein the attaching comprises contacting the known region of the nucleic acid molecule to a CRISPR nucleic acid-protein complex. 38. The method of embodiment 24, wherein the CRISPR nucleic acid-protein complex comprises a guide RNA comprising SEQ ID NO: 3. 39. The method of embodiment 24, wherein the attaching comprises ligating the nucleic acid fragment comprising promoter sequence. 40. The method of embodiment 24, wherein the nucleic acid fragment comprising promoter sequence comprises a viral promoter. 41. The method of embodiment 40, wherein the viral promoter is at least one promoter selected from the list consisting of T7, T3, T7lac, SP6, pL, CMV, SV40, and CaMV35S. 42. The method of embodiment 24, wherein the nucleic acid fragment comprising promoter sequence comprises a bacterial promoter. 43. The method of embodiment 42, wherein the bacterial promoter is at least one promoter selected from the list consisting of araBAD, trp, lac, and Ptac. 44. The method of embodiment 24, wherein the nucleic acid fragment comprising promoter sequence comprises a eukaryotic promoter. 45. The method of embodiment 44, wherein the eukaryotic promoter is at least one promoter selected from the list consisting of EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. 46. The method of embodiment 44, wherein the eukaryotic promoter is at least one promoter selected from the list consisting of an RNA pol I promoter, an RNA polII promoter and an RNA polIII promoter. 47. The method of embodiment 24, wherein the known region of a nucleic acid molecule comprises a repetitive element. 48. The method of embodiment 47, wherein the repetitive element comprises a mobile insertion element. 49. The method of embodiment 47, wherein the repetitive element comprises at least one of a LINE element, a SINE element, an Alu repeat, a transposon, a retrotransposon, a centromeric repeat, and a telomeric repeat. 50. The method of embodiment 47, wherein the LINE element comprises SEQ ID NO: 1. 51. A nucleic acid library comprising nucleic acids encoding border adjacent sequence for at least 90% of a repeated mobile element's borders in a nucleic acid sample. 52. The nucleic acid library of embodiment 51, wherein discrepancies between library constituents and the nucleic acid sample are independently derived. 53. The nucleic acid library of embodiment 51, wherein at least 50% of said repeated element's borders are present in at least 100 copies. 54. The nucleic acid library of embodiment 51, wherein library constituents are derived directly from the nucleic acid sample. 55. The nucleic acid library of embodiment 51, wherein library components are not clonally amplified prior to sequencing. 56. The nucleic acid library of embodiment 51, wherein the nucleic acid sample is derived from a single cell. 57. The nucleic acid library of embodiment 51, wherein the nucleic acid library is reverse transcribed from an RNA intermediate. 58. The nucleic acid library of embodiment 51, wherein the nucleic acid library comprises RNA. 59. The nucleic acid library of embodiment 51, wherein nucleic acid library constituents comprise promoter sequence. 60. The nucleic acid library of embodiment 59, wherein the RNA promoter sequence comprises at least one of a T7, T3, T7lac, SP6, pL, CMV, SV40, CaMV35S, araBAD, trp, lac, Ptac, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. 61. The nucleic acid library of embodiment 51, wherein at least one border adjacent sequence indicates a defect in a gene related to at least one of cell cycle regulation, DNA repair, and growth regulation. 62. The nucleic acid library of embodiment 51, wherein nucleic acid library comprises nucleic acids encoding border adjacent sequence for at least 95% of a repeated mobile element's borders in a nucleic acid sample. 63. The nucleic acid library of embodiment 62, wherein nucleic acid library comprises nucleic acids encoding border adjacent sequence for at least 99% of a repeated mobile element's borders in a nucleic acid sample. 64. The nucleic acid library of embodiment 51, wherein at least 50% of the library constituent nucleic acids are located on a nucleic acid within 20 kb of a mobile element border. 65. The nucleic acid library of embodiment 51, wherein at least 75% of the library constituent nucleic acids are located on a nucleic acid within 20 kb of a mobile element border in proximity to a mobile element border. 66. The nucleic acid library of embodiment 51, wherein at least 90% of the library constituent nucleic acids are located on a nucleic acid within 20 kb of a mobile element border. 67. The nucleic acid library of embodiment 51, wherein at least 50% of the library constituent nucleic acids are located on a nucleic acid within 10 kb of a mobile element border. 68. The nucleic acid library of embodiment 51, wherein at least 75% of the library constituent nucleic acids are located on a nucleic acid within 10 kb of a mobile element border in proximity to a mobile element border. 69. The nucleic acid library of embodiment 51, wherein at least 90% of the library constituent nucleic acids are located on a nucleic acid within 10 kb of a mobile element border. 70. The nucleic acid library of embodiment 51, wherein at least 50% of the library constituent nucleic acids are located on a nucleic acid within 5 kb of a mobile element border. 71. The nucleic acid library of embodiment 51, wherein at least 75% of the library constituent nucleic acids are located on a nucleic acid within 5 kb of a mobile element border in proximity to a mobile element border. 72. The nucleic acid library of embodiment 51, wherein at least 90% of the library constituent nucleic acids are located on a nucleic acid within 5 kb of a mobile element border. 73. The nucleic acid library of embodiment 51, wherein at least 50% of the library constituent nucleic acids are located on a nucleic acid within 1kb of a mobile element border. 74. The nucleic acid library of embodiment 51, wherein at least 75% of the library constituent nucleic acids are located on a nucleic acid within 1 kb of a mobile element border in proximity to a mobile element border. 75. The nucleic acid library of embodiment 51, wherein at least 90% of the library constituent nucleic acids are located on a nucleic acid within 1kb of a mobile element border. 76. The nucleic acid library of any one of embodiments 51 to 75, wherein the mean fragment length is about 500 bases. 77. The nucleic acid library of any one of embodiments 51 to 75, wherein the mean fragment length is about 1000 bases. 78. The nucleic acid library of any one of embodiments 51 to 75, wherein the median fragment length is about 500 bases. 79. The nucleic acid library of any one of embodiments 51 to 75, wherein the median fragment length is about 1000 bases. 80. A composition comprising a targeting sequence and a promoter, wherein the targeting sequence comprises a nucleic acid sequence that directs insertion of the composition into one or more specific locations in a nucleic acid sequence and the promoter comprises a nucleic acid sequence that directs synthesis of a nucleic acid from a sample sequence adjacent to the insertion of the promoter. 81. The composition of embodiment 80, wherein the targeting sequence comprises a nucleic acid sequence homologous to the specific location. 82. The composition of embodiment 80, wherein the targeting sequence comprises a nucleic acid sequence that base pairs to the specific location. 83. The composition of embodiment 80, wherein the targeting sequence comprises a nucleic acid sequence that hybridizes to the specific location. 84. The composition of any one of embodiments 80 to 83, wherein the targeting sequence comprises at least one of clustered regularly interspaced short palindromic repeats (CRISPR) sequence, a zinc finger nuclease (ZFN) sequence, and a transcription activator-like effector nucleases (TAL- ENs) sequence. 85. The composition of embodiment 84, wherein the CRISPR sequence comprises a guide RNA with a sequence comprising SEQ ID NO: 3. 86. The composition of any one of embodiments 80 to 85, wherein the promoter comprises at least one of a bacterial promoter, a viral promoter, and a eukaryotic promoter. 87. The composition of embodiment 86, wherein the bacterial promoter comprises at least one of araBAD, trp, lac, and Ptac. 88. The composition of embodiment 86, wherein the viral promoter comprises at least one of T7, T7lac, SP6, pL, CMV, SV40, and CaMV35S. 89. The composition of embodiment 86, wherein the eukaryotic promoter comprises at least one of EFla, PGK1, Ubc, beta actin, CAG, TRE, UAS, Ac5, Polyhedrin, CaMKIIa, ALB, GALL, GAL10, TEF1, GDS, ADH1, Ubi, H1, and U6. 90. The composition of any one of embodiments 80 to 89, wherein the specific location in the nucleic acid sequence comprises a low-complexity nucleic acid sequence. 91. The composition of any one of embodiments 80 to 90, wherein the specific location in the nucleic acid sequence comprises a repetitive nucleic acid sequence. 92. The composition of any one of embodiments 80 to 91, wherein the low-complexity nucleic acid sequence or the repetitive nucleic acid sequence comprises at least one of a tri-nucleotide repeat, tandem repeat, and human leukocyte antigen gene. 93. The composition of any one of embodiments 80 to 91, wherein the specific location in the nucleic acid sequence comprises a mobile genetic element. 94. The composition of embodiment 93, wherein the mobile genetic element comprises at least one of a transposon, a retrotransposon, a DNA transposon, an insertion sequence, a plasmid, a bacteriophage, a group II intron, a group I intron, an Alu element, a MIR element, an intracisternal A particle (TAP), an ETn, a virus, and a fragments thereof 95. The composition of embodiment 94, wherein the retrotransposon comprises at least one of a transposable element, a LINE, a SINE, and fragments thereof 96. The composition of embodiment 94, wherein the LINE comprises SEQ ID NO: 1. 97. The composition of embodiment 94, wherein the virus comprises a retrovirus or a fragment thereof 98. The composition of any one of embodiments 80 to 97, wherein the nucleic acid synthesis comprises at least one of RNA transcription and DNA synthesis. 99. A method of determining a nucleic acid sequence adjacent to a nucleic acid sequence of interest comprising: (a) inserting a targeting nucleic acid sequence comprising a targeting sequence and a promoter into one or more specific locations in the nucleic acid sequence of interest, (b) directing synthesis of a nucleic acid from the promoter, and (c) sequencing the synthesized nucleic acid. 100. The method of embodiment 99, wherein the targeting sequence comprises at least one of a clustered regularly interspaced short palindromic repeats (CRISPR) sequence, a zinc finger nuclease (ZFN) sequence, and a transcription activator-like effector nucleases (TALENs) sequence. 101. The composition of embodiment 100, wherein the CRISPR sequence comprises a guide RNA with a sequence comprising SEQ ID NO: 3. 102. The method of embodiment any one of embodiments 99 to 101, wherein the promoter comprises at least one of a bacterial promoter, a viral promoter, and a eukaryotic promoter. 103. The method of embodiment 102, wherein the bacterial promoter comprises at least one of araBAD, trp, lac, and Ptac. 104. The method of embodiment 102, wherein the viral promoter comprises at least one of T7, T7lac, SP6, pL, CMV, SV40, and CaMV35S. 105. The method of embodiment 102, wherein eukaryotic promoter comprises at least one of EFla, PGK1, Ubc, beta actin, CAG, TRE, UAS, Ac5, Polyhedrin, CaMKIIa, GAL1, GAL10, TEF1, GDS, ADH1, Ubi, H1, and U6. 106. The method of any one of embodiments 99 to 105, wherein the sequence of interest comprises a low-complexity nucleic acid sequence. 107. The method of any one of embodiments 99 to 106, wherein the sequence of interest comprises a repetitive nucleic acid sequence. 108. The method of any one of embodiments 99 to 107, wherein the sequence of interest comprises at least one of tri-nucleotide repeat, tandem repeat, and human leukocyte antigen gene. 109. The method of any one of embodiments 99 to 108, wherein the sequence of interest comprises a mobile genetic element. 110. The method of embodiment 109, wherein the mobile genetic element comprises a transposon, a retrotransposon, a DNA transposon, an insertion sequence, a plasmid, a bacteriophage, a group II intron, a group I intron, an Alu element, a MIR element, an intracisternal A particle (TAP), an ETn, a virus, or a fragment thereof 111. The method of embodiment 110, wherein the retrotransposon comprises at least one of transposable element, a LINE, a SINE, and fragments thereof. 112. The method of embodiment 111, wherein the LINE comprises SEQ ID NO: 1. 113. The method of embodiment 110, wherein the virus comprises at least one of a retrovirus and fragments thereof 114. The method of any one of embodiments 99 to 113, wherein nucleic acid synthesis comprises at least one of RNA transcription and DNA synthesis. 115. The method of embodiment 114, wherein RNA transcription comprises use of a RNA polymerase. 116. The method of embodiment 115, wherein the RNA polymerase comprises at least one of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase. 117. The method of any one of embodiments 99 to 114, wherein DNA synthesis comprises use of a DNA polymerase. 118. The method of embodiment 117, wherein the DNA polymerase comprises at least one of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase. 119. The method of any one of embodiments 99 to 118, wherein the nucleic acid synthesis requires a primer. 120. The method of any one of embodiments 99 to 119, wherein the synthesized nucleic acid is synthesized directly from the nucleic acid sequence of interest. 121. The method of any one of embodiments 99 to 120, wherein the nucleic acid is synthesized without introducing a mutation. 122. The method of embodiment 121, wherein the mutation is at least one of a point mutation, a deletion, an insertion, and a chimera. 123. The method of any one of embodiments 99 to 122, wherein the synthesized nucleic acid comprises DNA. 124. The method of any one of embodiments 99 to 122, wherein the synthesized nucleic acid comprises cDNA. 125. The method of embodiment 123 or embodiment 124, wherein the synthesized nucleic acid is treated with an RNase. 126. The method of any one of embodiments 99 to 122, wherein the synthesized nucleic acid is a RNA. 127. The method of embodiment 126, wherein the synthesized nucleic acid is treated with a DNase. 128. The method of any one of embodiments 99 to 127, wherein the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation. 129. The method of any one of embodiments 99 to 128, wherein the method detects a mutation in a subject. 130. The method of any one of embodiments 99 to 128, wherein the method detects a mutation in a tissue sample obtained from a subject. 131. The method of embodiment 130, wherein the tissue sample comprises at least one of tumor, blood, saliva, sputum, skin, and epithelial tissue. 132. A method of mapping a site of insertion of a DNA element in a nucleic acid sample from a subject, comprising: i) inserting a targeting nucleic acid sequence comprising a targeting sequence and a promoter by contacting the genomic DNA with the targeting sequence and one or more reagents sufficient to insert the targeting sequence into the DNA element; ii) creating an amplified nucleic acid directly from the genomic DNA by contacting the inserted targeting sequence with one or more enzymes that catalyze nucleic acid synthesis from the promoter thereby creating an amplified nucleic acid; iii) sequencing the amplified nucleic acid. 133. The method of embodiment 132, wherein the targeting sequence comprises at least one of a clustered regularly interspaced short palindromic repeats (CRISPR) sequence, a zinc finger nuclease (ZFN) sequence, and a transcription activator-like effector nucleases (TALENs) sequence. 134. The composition of embodiment 133, wherein the CRISPR sequence comprises a guide RNA with a sequence comprising SEQ ID NO: 3. 135. The method of any one of embodiments 132 to 134, wherein the promoter comprises at least one of a bacterial promoter, a viral promoter, and a eukaryotic promoter. 136. The method of embodiment 135, wherein the bacterial promoter comprises at least one of araBAD, trp, lac, and Ptac. 137. The method of embodiment 135, wherein the viral promoter comprises at least one of T7, T7lac, SP6, pL, CMV, SV40, and CaMV35S. 138. The method of embodiment 135, wherein eukaryotic promoter comprises at least one of EF1a, PGK1, Ubc, beta actin, CAG, TRE, UAS, Ac5, Polyhedrin, CaMKIIa, GAL1, GAL10, TEF1, GDS, ADH1, Ubi, H1, and U6. 139. The method of any one of embodiments 132 to 138, wherein the DNA element comprises a low-complexity nucleic acid sequence. 140. The method of any one of embodiments 132 to 139, wherein the DNA element comprises a repetitive nucleic acid sequence. 141. The method of any one of embodiments 132 to 140, wherein the DNA element comprises at least one of a tri-nucleotide repeat, and tandem repeat. 142. The method of any one of embodiments 132 to 141, wherein the DNA element comprises a mobile genetic element. 143. The method of embodiment 142, wherein the mobile genetic element comprises at least one of a transposon, a retrotransposon, a DNA transposon, an insertion sequence, a plasmid, a bacteriophage, a group II intron, a group I intron, an Alu element, a MIR element, an intracisternal A particle (TAP), an ETn, a virus, and fragments thereof. 144. The method of embodiment 143, wherein the retrotransposon comprises at least one of a transposable element, a LINE, a SINE, and fragments thereof 145. The method of embodiment 144, wherein the LINE comprises SEQ ID NO: 1. 146. The method of embodiment 143, wherein the virus comprises a retrovirus or a fragment thereof. 147. The method of embodiment 132 to 146, wherein the enzyme comprises a RNA polymerase. 148. The method of embodiment 147, wherein the RNA polymerase comprises at least one of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase. 149. The method of any one of embodiments 132 to 148, wherein the enzyme a DNA polymerase. 150. The method of embodiment 149, wherein the DNA polymerase comprises at least one of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase. 151. The method of any one of embodiments 132 to 150, wherein the nucleic acid synthesis requires a primer. 152. The method of any one of embodiments 132 to 151, wherein the synthesized nucleic acid is synthesized directly from the nucleic acid sequence of interest. 153. The method of any one of embodiments 132 to 152, wherein the nucleic acid is synthesized without introducing a mutation. 154. The method of embodiment 153, wherein the mutation is at least one of a point mutation, a deletion, an insertion, and a chimera. 155. The method of any one of embodiments 132 to 154, wherein the synthesized nucleic acid is a DNA. 156. The method of any one of embodiments 132 to 154, wherein the synthesized nucleic acid is a cDNA. 157. The method of embodiment 155 or embodiment 156, wherein the synthesized nucleic acid is treated with an RNase. 158. The method of any one of embodiments 132 to 154, wherein the synthesized nucleic acid is a RNA. 159. The method of embodiment 158, wherein the synthesized nucleic acid is treated with a DNase. 160. The method of any one of embodiments 132 to 159, wherein the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation. 161. The method of any one of embodiments 132 to 160, wherein the method detects a mutation in a subject. 162. The method of any one of embodiments 132 to 160, wherein the method detects a mutation in a tissue sample obtained from a subject. 163. The method of embodiment 162, wherein the tissue sample comprises at least one of tumor, blood, saliva, sputum, skin, and epithelial tissue. 164. A method of sequencing a repetitive genomic region comprising: i) inserting a targeting nucleic acid sequence comprising a targeting sequence and a promoter by contacting the genomic DNA with the targeting sequence and one or more reagents sufficient to insert the targeting sequence into the repetitive genomic region; ii) creating an amplified nucleic acid directly from the genomic DNA by contacting the inserted targeting sequence with one or more enzymes that catalyze nucleic acid synthesis from the promoter thereby creating an amplified nucleic acid; iii) sequencing the amplified nucleic acid. 165. The method of embodiment 164, wherein the targeting sequence comprises at least one of a clustered regularly interspaced short palindromic repeats (CRISPR) sequence, a zinc finger nuclease (ZFN) sequence, and a transcription activator-like effector nucleases (TALENs) sequence. 166. The composition of embodiment 165, wherein the CRISPR sequence comprises a guide RNA with a sequence comprising SEQ ID NO: 3. 167. The method of any one of embodiments 164 to 166, wherein the promoter comprises at least one of a bacterial promoter, a viral promoter, and a eukaryotic promoter. 168. The method of embodiment 167, wherein the bacterial promoter comprises at least one of araBAD, trp, lac, and Ptac. 169. The method of embodiment 167, wherein the viral promoter comprises at least one of T7, T7lac, SP6, pL, CMV, SV40, and CaMV35S. 170. The method of embodiment 167, wherein eukaryotic promoter comprises at least one of EF1a, PGK1, Ubc, beta actin, CAG, TRE, UAS, Ac5, Polyhedrin, CaMKIIa, GAL1, GAL10, TEF1, GDS, ADH1, Ubi, H1, and U6. 171. The method of any one of embodiments 164 to 170, wherein the repetitive genomic region comprises a low-complexity nucleic acid sequence. 172. The method of any one of embodiments 164 to 171, wherein the repetitive genomic region comprises a repetitive nucleic acid sequence. 173. The method of any one of embodiments 164 to 172, wherein the repetitive genomic region comprises at least one of a tri-nucleotide repeat and tandem repeat. 174. The method of any one of embodiments 164 to 173, wherein the repetitive genomic region comprises a mobile genetic element. 175. The method of embodiment 174, wherein the mobile genetic element comprises at least one of a transposon, a retrotransposon, a DNA transposon, an insertion sequence, a plasmid, a bacteriophage, a group II intron, a group I intron, an Alu element, a MIR element, an intracisternal A particle (TAP), an ETn, a virus, and fragments thereof. 176. The method of embodiment 175, wherein the retrotransposon comprises at least one of a transposable element, a LINE, a SINE, and fragments thereof 177. The method of embodiment 176, wherein the LINE comprises SEQ ID NO: 1. 178. The method of embodiment 175, wherein the virus comprises a retrovirus or a fragment thereof. 179. The method of embodiment 164 to 178, wherein the enzyme comprises a RNA polymerase. 180. The method of embodiment 179, wherein the RNA polymerase comprises at least one of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase. 181. The method of any one of embodiments 164 to 178, wherein the enzyme comprises a DNA polymerase. 182. The method of embodiment 181, wherein the DNA polymerase comprises at least one of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase. 183. The method of any one of embodiments 164 to 182, wherein the nucleic acid synthesis requires a primer. 184. The method of any one of embodiments 164 to 183, wherein the synthesized nucleic acid is synthesized directly from the nucleic acid sequence of interest. 185. The method of any one of embodiments 164 to 184, wherein the nucleic acid is synthesized without introducing a mutation. 186. The method of embodiment 185, wherein the mutation is at least one of a point mutation, a deletion, an insertion, and a chimera. 187. The method of any one of embodiments 164 to 186, wherein the synthesized nucleic acid is a DNA. 188. The method of any one of embodiments 164 to 186, wherein the synthesized nucleic acid is a cDNA. 189. The method of embodiment 187 or embodiment 188, wherein the synthesized nucleic acid is treated with an RNase. 190. The method of any one of embodiments 164 to 186, wherein the synthesized nucleic acid is a RNA. 191. The method of embodiment 190, wherein the synthesized nucleic acid is treated with a DNase. 192. The method of any one of embodiments 164 to 191, wherein the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation. 193. The method of any one of embodiments 164 to 192, wherein the method detects a mutation in a subject. 194. The method of any one of embodiments 164 to 192, wherein the method detects a mutation in a tissue sample obtained from a subject. 195. The method of embodiment 194, wherein the tissue sample comprises at least one of tumor, blood, saliva, sputum, skin, and epithelial tissue. 196. A method of determining a sequence adjacent to a region of known sequence of a nucleic acid molecule, the method comprising a) attaching a hairpin nucleic acid fragment comprising a double stranded promoter segment an overhanging single stranded portion that anneals to at least some of the nucleic acid molecule at the known region of the nucleic acid molecule, and a single stranded tether connecting the first strand and the second strand of the double-stranded promoter; b) contacting the nucleic acid fragment to an RNA polymerase directed by the promoter; and c) synthesizing a plurality of RNA molecules; wherein the overhanging single stranded portion basepairs with a reverse complementary portion of the region of known sequence, and wherein a consensus sequence of the plurality of RNA molecules represents the sequence adjacent to the known region of a nucleic acid molecule. 197. The method of embodiment 196, wherein the consensus sequence is at least 10 kilobases in length. 198. The method of any one of embodiments 196 or 197, comprising treating the nucleic acid molecule using a DNase subsequent to synthesizing the plurality of RNA molecules. 199. The method of any one of embodiments 196 to 198, comprising reverse-transcribing the plurality of RNA molecules. 200. The method of any one of embodiments 196 to 199, comprising determining nucleic acid sequences of the plurality of RNA molecules. 201. The method of any one of embodiments 196 to 200, wherein the consensus sequence of the plurality of RNA molecules comprises sequence of molecules synthesized directly from the nucleic acid molecule. 202. The method of any one of embodiments 196 to 201, wherein the attaching comprises inserting the nucleic acid fragment comprising a double stranded promoter sequence at the known region of the nucleic acid molecule. 203. The method of any one of embodiments 196 to 202, wherein the attaching comprises hybridizing the nucleic acid fragment comprising double stranded promoter sequence at the region of known sequence of the nucleic acid molecule. 204. The method of any one of embodiments 196 to 203, wherein the attaching comprises sequence-specific cleavage of the region of known sequence of the nucleic acid molecule. 205. The method of any one of embodiments 196 to 204, wherein the attaching comprises contacting the known region of the nucleic acid molecule to a CRISPR nucleic acid-protein complex. 206. The method of embodiment 205, wherein the CRISPR nucleic acid-protein complex comprises a guide RNA comprising SEQ ID NO: 3. 207. The method of any one of embodiments 196 to 206, wherein the attaching comprises ligating the nucleic acid fragment comprising double stranded promoter sequence. 208. The method of any one of embodiments 196 to 207, wherein the nucleic acid fragment comprising double stranded promoter sequence comprises a viral promoter. 209. The method of embodiment 208, wherein the viral promoter binds a viral RNA polymerase and is at least one promoter selected from the list consisting of T7, T3, T7lac, SP6, pL, CMV, SV40, and CaMV35S. 210. The method of any one of embodiments 196 to 207, wherein the nucleic acid fragment comprising double stranded promoter sequence comprises a bacterial promoter. 211. The method of embodiment 210, wherein the bacterial promoter binds a bacterial RNA polymerase and is at least one promoter selected from the list consisting of araBAD, trp, lac, and Ptac. 212. The method of any one of embodiments 196 to 207, wherein the nucleic acid fragment comprising the double stranded promoter sequence comprises a eukaryotic promoter. 213. The method of embodiment 212, wherein the eukaryotic promoter binds a eukaryotic RNA polymerase and is at least one promoter selected from the list consisting of EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. 214. The method of embodiment 213, wherein the eukaryotic promoter is at least one promoter selected from the list consisting of an RNA pol I promoter, an RNA pol II promoter and an RNA pol III promoter. 215. The method of any one of embodiments 196 to 214, wherein the known region of a nucleic acid molecule comprises a repetitive element. 216. The method of embodiment 215, wherein the repetitive element comprises a mobile insertion element. 217. The method of embodiment 215, wherein the repetitive element comprises at least one of a LINE element, a SINE element, an Alu repeat, a transposon, a retrotransposon, a centromeric repeat, and a telomeric repeat. 218. The method of embodiment 215, wherein the LINE element comprises SEQ ID NO: 1. 219. A method of determining a plurality of locus-adjacent sequences of an element in a nucleic acid sample, comprising the steps of a) inserting a hairpin nucleic acid comprising a double stranded promoter and a single stranded overhanging portion that hybridizes to a reverse complementary portion of the element into the element, b) generating a plurality of nucleic acid molecules directed by the promoter, and c) determining the sequence of the plurality of nucleic acid molecules, wherein the nucleic acid molecules are synthesized directly from the nucleic acid sample and wherein the plurality of nucleic acid molecules span locus adjacent sequences. 220. The method of embodiment 219, wherein the nucleic acid molecules comprise RNA. 221. The method of embodiment 219, wherein the nucleic acid molecules cannot prime nucleic acid synthesis. 222. The method of embodiment 219, wherein the nucleic acid sample comprises cancer cell nucleic acids. 223. The method of embodiment 219, wherein the nucleic acid sample comprises a single nuclear genome. 224. The method of embodiment 219, wherein the nucleic acid sample is obtained from a single cell. 225. The method of embodiment 219, comprising treating the nucleic acid sample using a DNase subsequent to synthesizing the plurality of RNA molecules. 226. The method of embodiment 219, comprising reverse-transcribing the plurality of RNA molecules. 227. The method of embodiment 219, wherein the plurality of nucleic acid molecules are RNA molecules. 228. The method of embodiment 219, wherein the consensus sequence of the plurality of RNA molecules comprises sequence of molecules synthesized directly from the nucleic acid molecule. 229. The method of embodiment 219, wherein the attaching comprises inserting the nucleic acid fragment comprising a double stranded promoter sequence at the known region of the nucleic acid molecule. 230. The method of embodiment 219, wherein the attaching comprises hybridizing the nucleic acid fragment comprising a double stranded promoter sequence at the known region of the nucleic acid molecule. 231. The method of embodiment 219, wherein the attaching comprises sequence-specific cleavage of the known region of the nucleic acid molecule. 232. The method of embodiment 219, wherein the attaching comprises contacting the known region of the nucleic acid molecule to a CRISPR nucleic acid-protein complex. 233. The method of embodiment 219, wherein the CRISPR nucleic acid-protein complex comprises a guide RNA comprising SEQ ID NO: 3. 234. The method of embodiment 219, wherein the attaching comprises ligating the nucleic acid fragment comprising the double stranded promoter sequence. 235. The method of embodiment 219, wherein the nucleic acid fragment comprising the double stranded promoter sequence comprises a viral promoter. 236. The method of embodiment 235, wherein the viral promoter is at least one promoter selected from the list consisting of T7, T3, T7lac, SP6, pL, CMV, SV40, and CaMV35S. 237. The method of embodiment 219, wherein the nucleic acid fragment comprising the double stranded promoter sequence comprises a bacterial promoter. 238. The method of embodiment 237, wherein the bacterial promoter is at least one promoter selected from the list consisting of araBAD, trp, lac, and Ptac. 239. The method of embodiment 219, wherein the nucleic acid fragment comprising the double stranded promoter sequence comprises a eukaryotic promoter. 240. The method of embodiment 239, wherein the eukaryotic promoter is at least one promoter selected from the list consisting of EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. 241. The method of embodiment 239, wherein the eukaryotic promoter is at least one promoter selected from the list consisting of an RNA pol I promoter, an RNA polII promoter and an RNA polIII promoter. 242. The method of embodiment 219, wherein the known region of a nucleic acid molecule comprises a repetitive element. 243. The method of embodiment 242, wherein the repetitive element comprises a mobile insertion element. 244. The method of embodiment 242, wherein the repetitive element comprises at least one of a LINE element, a SINE element, an Alu repeat, a transposon, a retrotransposon, a centromeric repeat, and a telomeric repeat. 245. The method of embodiment 244, wherein the LINE element comprises SEQ ID NO: 1. 246. A nucleic acid library comprising hairpin nucleic acids encoding a border adjacent sequence for at least 90% of a repeated mobile element's borders in a nucleic acid sample and a double stranded promoter sequence. 247. The nucleic acid library of embodiment 246, wherein discrepancies between library constituents and the nucleic acid sample are independently derived. 248. The nucleic acid library of embodiment 246, wherein at least 50% of said repeated element's borders are present in at least 100 copies. 249. The nucleic acid library of embodiment 246, wherein library constituents are derived directly from the nucleic acid sample. 250. The nucleic acid library of embodiment 246, wherein library components are not clonally amplified prior to sequencing. 251. The nucleic acid library of embodiment 246, wherein the nucleic acid sample is derived from a single cell. 252. The nucleic acid library of embodiment 246, wherein the nucleic acid library is reverse transcribed from an RNA intermediate. 253. The nucleic acid library of embodiment 246, wherein the nucleic acid library comprises RNA. 254. The nucleic acid library of embodiment 246, wherein the double stranded promoter sequence comprises at least one of a bacterial promoter, a viral promoter, and a eukaryotic promoter. 255. The nucleic acid library of embodiment 246, wherein the promoter sequence comprises at least one of a T7, T3, T7lac, SP6, pL, CMV, SV40, CaMV35S, araBAD, trp, lac, Ptac, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. 256. The nucleic acid library of embodiment 246, wherein at least one border adjacent sequence indicates a defect in a gene related to at least one of cell cycle regulation, DNA repair, and growth regulation. 257. The nucleic acid library of embodiment 246, wherein nucleic acid library comprises nucleic acids encoding border adjacent sequence for at least 95% of a repeated mobile element's borders in a nucleic acid sample. 258. The nucleic acid library of embodiment 62, wherein nucleic acid library comprises nucleic acids encoding border adjacent sequence for at least 99% of a repeated mobile element's borders in a nucleic acid sample. 259. The nucleic acid library of embodiment 246, wherein at least 50% of the library constituent nucleic acids are located on a nucleic acid within 20 kb of a mobile element border. 260. The nucleic acid library of embodiment 246, wherein at least 75% of the library constituent nucleic acids are located on a nucleic acid within 20 kb of a mobile element border in proximity to a mobile element border. 261. The nucleic acid library of embodiment 246, wherein at least 90% of the library constituent nucleic acids are located on a nucleic acid within 20 kb of a mobile element border. 262. The nucleic acid library of embodiment 246, wherein at least 50% of the library constituent nucleic acids are located on a nucleic acid within 10 kb of a mobile element border. 263. The nucleic acid library of embodiment 246, wherein at least 75% of the library constituent nucleic acids are located on a nucleic acid within 10 kb of a mobile element border in proximity to a mobile element border. 264. The nucleic acid library of embodiment 246, wherein at least 90% of the library constituent nucleic acids are located on a nucleic acid within 10 kb of a mobile element border. 265. The nucleic acid library of embodiment 246, wherein at least 50% of the library constituent nucleic acids are located on a nucleic acid within 5 kb of a mobile element border. 266. The nucleic acid library of embodiment 246, wherein at least 75% of the library constituent nucleic acids are located on a nucleic acid within 5 kb of a mobile element border in proximity to a mobile element border. 267. The nucleic acid library of embodiment 246, wherein at least 90% of the library constituent nucleic acids are located on a nucleic acid within 5 kb of a mobile element border. 268. The nucleic acid library of embodiment 246, wherein at least 50% of the library constituent nucleic acids are located on a nucleic acid within 1 kb of a mobile element border. 269. The nucleic acid library of embodiment 246, wherein at least 75% of the library constituent nucleic acids are located on a nucleic acid within 1 kb of a mobile element border in proximity to a mobile element border. 270. The nucleic acid library of embodiment 246, wherein at least 90% of the library constituent nucleic acids are located on a nucleic acid within 1 kb of a mobile element border. 271. The nucleic acid library of any one of embodiments 246 to 270, wherein the mean fragment length is about 500 bases. 272. The nucleic acid library of any one of embodiments 246 to 270, wherein the mean fragment length is about 1000 bases. 273. The nucleic acid library of any one of embodiments 246 to 270, wherein the median fragment length is about 500 bases. 274. The nucleic acid library of any one of embodiments 246 to 270, wherein the median fragment length is about 1000 bases. 275. A composition comprising hairpin polynucleotide comprising a single stranded targeting sequence and a double stranded promoter, wherein the targeting sequence comprises a single stranded nucleic acid sequence that binds to a reverse complementary single stranded nucleic acid sequence at one or more specific locations in a nucleic acid sequence and the double stranded promoter comprises a nucleic acid sequence that directs synthesis of a nucleic acid from a sample sequence adjacent to the insertion of the promoter. 276. The composition of embodiment 275, wherein the single stranded targeting sequence comprises a single stranded nucleic acid sequence reverse complementary to the specific location. 277. The composition of embodiment 275, wherein the single stranded targeting sequence comprises a single stranded nucleic acid sequence that base pairs to the single stranded sequence at the specific location. 278. The composition of embodiment 275, wherein the single stranded targeting sequence comprises a single stranded nucleic acid sequence that hybridizes to the single stranded sequence at the specific location. 279. The composition of any one of embodiments 275 to 278, wherein the single stranded targeting sequence comprises at least one of clustered regularly interspaced short palindromic repeats (CRISPR) sequence, a zinc finger nuclease (ZFN) sequence, and a transcription activator-like effector nucleases (TALENs) sequence. 280. The composition of embodiment 279, wherein the CRISPR sequence comprises a guide RNA with a sequence comprising SEQ ID NO: 3. 281. The composition of any one of embodiments 275 to 280, wherein the double stranded promoter comprises at least one of a bacterial promoter, a viral promoter, and a eukaryotic promoter. 282. The composition of embodiment 281, wherein the bacterial promoter comprises at least one of araBAD, trp, lac, and Ptac. 283. The composition of embodiment 281, wherein the viral promoter comprises at least one of T7, T7lac, SP6, pL, CMV, SV40, and CaMV35S. 284. The composition of embodiment 281, wherein the eukaryotic promoter comprises at least one of EFla, PGK1, Ubc, beta actin, CAG, TRE, UAS, Ac5, Polyhedrin, CaMKIIa, ALB, GAL1, GAL10, TEF1, GDS, ADH1, Ubi, H1, and U6. 285. The composition of any one of embodiments 275 to 284, wherein the specific location in the nucleic acid sequence comprises a low-complexity nucleic acid sequence. 286. The composition of any one of embodiments 275 to 285, wherein the specific location in the nucleic acid sequence comprises a repetitive nucleic acid sequence. 287. The composition of any one of embodiments 275 to 286, wherein the low-complexity nucleic acid sequence or the repetitive nucleic acid sequence comprises at least one of a tri-nucleotide repeat, tandem repeat, and human leukocyte antigen gene. 288. The composition of any one of embodiments 275 to 286, wherein the specific location in the nucleic acid sequence comprises a mobile genetic element. 289. The composition of embodiment 288, wherein the mobile genetic element comprises at least one of a transposon, a retrotransposon, a DNA transposon, an insertion sequence, a plasmid, a bacteriophage, a group II intron, a group I intron, an Alu element, a MIR element, an intracisternal A particle (IAP), an ETn, a virus, and a fragments thereof. 290. The composition of embodiment 289, wherein the retrotransposon comprises at least one of a transposable element, a LINE, a SINE, and fragments thereof. 291. The composition of embodiment 289, wherein the LINE comprises SEQ ID NO: 1. 292. The composition of embodiment 289, wherein the virus comprises a retrovirus or a fragment thereof 293. The composition of any one of embodiments 275 to 292, wherein the nucleic acid synthesis comprises at least one of RNA transcription and DNA synthesis. 294. A method of determining a nucleic acid sequence adjacent to a nucleic acid sequence of interest comprising: (a) inserting a hairpin polynucleotide comprising a single stranded targeting sequence and a double stranded promoter into one or more specific locations in the nucleic acid sequence of interest, (b) directing synthesis of a nucleic acid from the promoter, and (c) sequencing the synthesized nucleic acid. 295. The method of embodiment 294, wherein the targeting sequence comprises at least one of a clustered regularly interspaced short palindromic repeats (CRISPR) sequence, a zinc finger nuclease (ZFN) sequence, and a transcription activator-like effector nucleases (TALENs) sequence. 296. The composition of embodiment 295, wherein the CRISPR sequence comprises a guide RNA with a sequence comprising SEQ ID NO: 3. 297. The method of any one of embodiments 294 to 296, wherein the double stranded promoter comprises at least one of a bacterial promoter, a viral promoter, and a eukaryotic promoter. 298. The method of embodiment 297, wherein the bacterial promoter comprises at least one of araBAD, trp, lac, and Ptac. 299. The method of embodiment 297, wherein the viral promoter comprises at least one of T7, T7lac, SP6, pL, CMV, SV40, and CaMV35S. 300. The method of embodiment 297, wherein eukaryotic promoter comprises at least one of EF1a, PGK1, Ubc, beta actin, CAG, TRE, UAS, Ac5, Polyhedrin, CaMKIIa, GAL1, GAL10, TEF1, GDS, ADH1, Ubi, H1, and U6. 301. The method of any one of embodiments 294 to 300, wherein the sequence of interest comprises a low-complexity nucleic acid sequence. 302. The method of any one of embodiments 294 to 301, wherein the sequence of interest comprises a repetitive nucleic acid sequence. 303. The method of any one of embodiments 294 to 302, wherein the sequence of interest comprises at least one of tri-nucleotide repeat, tandem repeat, and human leukocyte antigen gene. 304. The method of any one of embodiments 294 to 303, wherein the sequence of interest comprises a mobile genetic element. 305. The method of embodiment 304, wherein the mobile genetic element comprises a transposon, a retrotransposon, a DNA transposon, an insertion sequence, a plasmid, a bacteriophage, a group II intron, a group I intron, an Alu element, a MIR element, an intracisternal A particle (IAP), an ETn, a virus, or a fragment thereof 306. The method of embodiment 305, wherein the retrotransposon comprises at least one of transposable element, a LINE, a SINE, and fragments thereof. 307. The method of embodiment 306, wherein the LINE comprises SEQ ID NO: 1. 308. The method of embodiment 305, wherein the virus comprises at least one of a retrovirus and fragments thereof. 309. The method of any one of embodiments 294 to 308, wherein nucleic acid synthesis comprises at least one of RNA transcription and DNA synthesis. 310. The method of embodiment 309, wherein RNA transcription comprises use of a RNA polymerase. 311. The method of embodiment 310, wherein the RNA polymerase comprises at least one of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase. 312. The method of any one of embodiments 294 to 311, wherein DNA synthesis comprises use of a DNA polymerase. 313. The method of embodiment 312, wherein the DNA polymerase comprises at least one of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase. 314. The method of any one of embodiments 294 to 313, wherein the nucleic acid synthesis requires a primer. 315. The method of any one of embodiments 294 to 314, wherein the synthesized nucleic acid is synthesized directly from the nucleic acid sequence of interest. 316. The method of any one of embodiments 294 to 315, wherein the nucleic acid is synthesized without introducing a mutation. 317. The method of embodiment 316, wherein the mutation is at least one of a point mutation, a deletion, an insertion, and a chimera. 318. The method of any one of embodiments 294 to 317, wherein the synthesized nucleic acid comprises DNA. 319. The method of any one of embodiments 294 to 318, wherein the synthesized nucleic acid comprises cDNA. 320. The method of embodiment 318 or embodiment 319, wherein the synthesized nucleic acid is treated with an RNase. 321. The method of any one of embodiments 294 to 317, wherein the synthesized nucleic acid is an RNA. 322. The method of embodiment 321, wherein the synthesized nucleic acid is treated with a DNase. 323. The method of any one of embodiments 294 to 322, wherein the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation. 324. The method of any one of embodiments 294 to 323, wherein the method detects a mutation in a subject. 325. The method of any one of embodiments 294 to 324, wherein the method detects a mutation in a tissue sample obtained from a subject. 326. The method of embodiment 325, wherein the tissue sample comprises at least one of tumor, blood, saliva, sputum, skin, and epithelial tissue. 327. A method of mapping a site of insertion of a DNA element in a nucleic acid sample from a subject, comprising: i) inserting a hairpin polynucleotide comprising a single stranded targeting sequence and a double stranded promoter by contacting the genomic DNA with the targeting sequence and one or more reagents sufficient to insert the targeting sequence into the DNA element; ii) creating an amplified nucleic acid directly from the genomic DNA by contacting the inserted targeting sequence with one or more enzymes that catalyze nucleic acid synthesis from the double stranded promoter thereby creating an amplified nucleic acid; iii) sequencing the amplified nucleic acid. 328. The method of embodiment 327, wherein the targeting sequence comprises at least one of a clustered regularly interspaced short palindromic repeats (CRISPR) sequence, a zinc finger nuclease (ZFN) sequence, and a transcription activator-like effector nucleases (TALENs) sequence. 329. The composition of embodiment 328, wherein the CRISPR sequence comprises a guide RNA with a sequence comprising SEQ ID NO: 3. 330. The method of any one of embodiments 327 to 329, wherein the double stranded promoter comprises at least one of a bacterial promoter, a viral promoter, and a eukaryotic promoter. 331. The method of embodiment 330, wherein the bacterial promoter comprises at least one of araBAD, trp, lac, and Ptac. 332. The method of embodiment 330, wherein the viral promoter comprises at least one of T7, T7lac, SP6, pL, CMV, SV40, and CaMV35S. 333. The method of embodiment 330, wherein eukaryotic promoter comprises at least one of EF1a, PGK1, Ubc, beta actin, CAG, TRE, UAS, Ac5, Polyhedrin, CaMKIIa, GAL1, GAL10, TEF1, GDS, ADH1, Ubi, H1, and U6. 334. The method of any one of embodiments 327 to 333, wherein the DNA element comprises a low-complexity nucleic acid sequence. 335. The method of any one of embodiments 327 to 334, wherein the DNA element comprises a repetitive nucleic acid sequence. 336. The method of any one of embodiments 327 to 335, wherein the DNA element comprises at least one of a tri-nucleotide repeat, and tandem repeat. 337. The method of any one of embodiments 327 to 336, wherein the DNA element comprises a mobile genetic element. 338. The method of embodiment 337, wherein the mobile genetic element comprises at least one of a transposon, a retrotransposon, a DNA transposon, an insertion sequence, a plasmid, a bacteriophage, a group II intron, a group I intron, an Alu element, a MIR element, an intracisternal A particle (TAP), an ETn, a virus, and fragments thereof 339. The method of embodiment 338, wherein the retrotransposon comprises at least one of a transposable element, a LINE, a SINE, and fragments thereof. 340. The method of embodiment 339, wherein the LINE comprises SEQ ID NO: 1. 341. The method of embodiment 338, wherein the virus comprises a retrovirus or a fragment thereof 342. The method of embodiment 327 to 341, wherein the enzyme comprises a RNA polymerase. 343. The method of embodiment 342, wherein the RNA polymerase comprises at least one of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase. 344. The method of any one of embodiments 327 to 343, wherein the enzyme a DNA polymerase. 345. The method of embodiment 344, wherein the DNA polymerase comprises at least one of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase. 346. The method of any one of embodiments 327 to 345, wherein the nucleic acid synthesis requires a primer. 347. The method of any one of embodiments 327 to 346, wherein the synthesized nucleic acid is synthesized directly from the nucleic acid sequence of interest. 348. The method of any one of embodiments 327 to 347, wherein the nucleic acid is synthesized without introducing a mutation. 349. The method of embodiment 348, wherein the mutation is at least one of a point mutation, a deletion, an insertion, and a chimera. 350. The method of any one of embodiments 327 to 349, wherein the synthesized nucleic acid is a DNA. 351. The method of any one of embodiments 327 to 349, wherein the synthesized nucleic acid is a cDNA. 352. The method of embodiment 350 or embodiment 351, wherein the synthesized nucleic acid is treated with an RNase. 353. The method of any one of embodiments 327 to 349, wherein the synthesized nucleic acid is an RNA. 354. The method of embodiment 353, wherein the synthesized nucleic acid is treated with a DNase. 355. The method of any one of embodiments 327 to 354, wherein the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation. 356. The method of any one of embodiments 327 to 355, wherein the method detects a mutation in a subject. 357. The method of any one of embodiments 327 to 355, wherein the method detects a mutation in a tissue sample obtained from a subject. 358. The method of embodiment 357, wherein the tissue sample comprises at least one of tumor, blood, saliva, sputum, skin, and epithelial tissue. 359. A method of sequencing a repetitive genomic region comprising: i) inserting a hairpin targeting nucleic acid sequence comprising a single stranded targeting sequence and a double stranded promoter by contacting the genomic DNA with the targeting sequence and one or more reagents sufficient to insert the single stranded targeting sequence into a reverse complementary sequence at the repetitive genomic region; ii) creating an amplified nucleic acid directly from the genomic DNA by contacting the inserted targeting sequence with one or more enzymes that catalyze nucleic acid synthesis from the double stranded promoter thereby creating an amplified nucleic acid; iii) sequencing the amplified nucleic acid. 360. The method of embodiment 359, wherein the targeting sequence comprises at least one of a clustered regularly interspaced short palindromic repeats (CRISPR) sequence, a zinc finger nuclease (ZFN) sequence, and a transcription activator-like effector nucleases (TALENs) sequence. 361. The composition of embodiment 360, wherein the CRISPR sequence comprises a guide RNA with a sequence comprising SEQ ID NO: 3. 362. The method of any one of embodiments 359 to 361, wherein the double stranded promoter comprises at least one of a bacterial promoter, a viral promoter, and a eukaryotic promoter. 363. The method of embodiment 362, wherein the bacterial promoter comprises at least one of araBAD, trp, lac, and Ptac. 364. The method of embodiment 362, wherein the viral promoter comprises at least one of T7, T7lac, SP6, pL, CMV, SV40, and CaMV35S. 365. The method of embodiment 362, wherein eukaryotic promoter comprises at least one of EF1a, PGK1, Ubc, beta actin, CAG, TRE, UAS, Ac5, Polyhedrin, CaMKIIa, GAL1, GAL10, TEF1, GDS, ADH1, Ubi, H1, and U6. 366. The method of any one of embodiments 359 to 365, wherein the repetitive genomic region comprises a low-complexity nucleic acid sequence. 367. The method of any one of embodiments 359 to 366, wherein the repetitive genomic region comprises a repetitive nucleic acid sequence. 368. The method of any one of embodiments 359 to 367, wherein the repetitive genomic region comprises at least one of a tri-nucleotide repeat and tandem repeat. 369. The method of any one of embodiments 359 to 368, wherein the repetitive genomic region comprises a mobile genetic element. 370. The method of embodiment 369, wherein the mobile genetic element comprises at least one of a transposon, a retrotransposon, a DNA transposon, an insertion sequence, a plasmid, a bacteriophage, a group II intron, a group I intron, an Alu element, a MIR element, an intracisternal A particle (TAP), an ETn, a virus, and fragments thereof 371. The method of embodiment 370, wherein the retrotransposon comprises at least one of a transposable element, a LINE, a SINE, and fragments thereof 372. The method of embodiment 371, wherein the LINE comprises SEQ ID NO: 1. 373. The method of embodiment 370, wherein the virus comprises a retrovirus or a fragment thereof 374. The method of embodiment 359 to 373, wherein the enzyme comprises a RNA polymerase. 375. The method of embodiment 374, wherein the RNA polymerase comprises at least one of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase. 376. The method of any one of embodiments 359 to 373, wherein the enzyme comprises a DNA polymerase. 377. The method of embodiment 376, wherein the DNA polymerase comprises at least one of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase. 378. The method of any one of embodiments 359 to 377, wherein the nucleic acid synthesis requires a primer. 379. The method of any one of embodiments 359 to 378, wherein the synthesized nucleic acid is synthesized directly from the nucleic acid sequence of interest. 380. The method of any one of embodiments 359 to 379, wherein the nucleic acid is synthesized without introducing a mutation. 381. The method of embodiment 380, wherein the mutation is at least one of a point mutation, a deletion, an insertion, and a chimera. 382. The method of any one of embodiments 359 to 381, wherein the synthesized nucleic acid is a DNA. 383. The method of any one of embodiments 359 to 381, wherein the synthesized nucleic acid is a cDNA. 384. The method of embodiment 382 or embodiment 383, wherein the synthesized nucleic acid is treated with an RNase. 385. The method of any one of embodiments 359 to 381, wherein the synthesized nucleic acid is an RNA. 386. The method of embodiment 385, wherein the synthesized nucleic acid is treated with a DNase. 387. The method of any one of embodiments 359 to 386, wherein the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation. 388. The method of any one of embodiments 359 to 387, wherein the method detects a mutation in a subject. 389. The method of any one of embodiments 359 to 387, wherein the method detects a mutation in a tissue sample obtained from a subject. 390. The method of embodiment 389, wherein the tissue sample comprises at least one of tumor, blood, saliva, sputum, skin, and epithelial tissue.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Target Specific Amplification of HLA Genes

HLA regions are notoriously hard to assemble with short read sequencers. They are both highly polymorphic and highly repetitive. Guide RNA designed upstream of the HLA-A gene promoter in example coordinates chr6:29,940,000-29,942,000 will have the potential to generate T7 transcribed RNA products spanning the entire HLA gene at about 5 kb of sequence.

In order to sequence the HLA gene, a plasmid is designed to include the targeted sequence from the HLA promoter with a T7 promoter inserted. The targeted sequence is selected to work most effectively with Cas9 in the CRISPR system. Once the plasmid containing the target sequence and the T7 promoter is designed and prepared, a guide RNA is transcribed and resulting guide RNA is incubated with the genomic DNA sample and isolated Cas9 enzyme. Alternatively, the guide RNA is synthesized or generated from a double stranded linear template. The resulting product, a tagged genomic DNA sample that has a T7 promoter inserted in the promoter region of the HLA-A gene, is then purified. The tagged genomic DNA sample is incubated with nucleotides and a T7 RNA polymerase which creates an RNA transcript from the HLA-A gene. Each transcript is made directly from the tagged genomic DNA sample and no errors such as insertions, deletions, or point mutations are made. The RNA sample is then purified from the tagged genomic DNA sample and polyadenylated. A cDNA is made from the RNA sample in a reverse transcriptase reaction and oligo-dT. The RNA is removed from the cDNA using RNase H and the cDNA is used in sequencing reactions to determine the sequence of the HLA-A gene with high accuracy possible in this method. The sequence of the HLA-A gene provides information about the subject from whom the genomic DNA sample was taken and thereby provides an accurate HLA typing at the HLA-A gene.

Example 2

Identification of Somatic Mobile Elements such as LINE-1 Rearrangements in Tumors LINE -1 rearrangements are estimated to rearrange genomic material once in every 20 cell divisions. The mechanism behind transposition may include the copy and paste of genomic DNA sequence outside of the canonical LINE-1 element sequence and insert that sequence in a new position. Published examples of this "tag along" genomic material is in some cases as long as 10 kilobases. Short read sequences do not have the ability to map these events as mapping based assembly will not position short reads corresponding to shuffled genomic material in a new location that is in conflict with the reference genome used for short read assembly. The ability to sequence through a contiguous molecule of lengths greater than 10 kilobases and into the flanking genomic sequence has the ability to identify and quantify these events. A guide RNA with complimentary target sequence to conserved regions of the human LINE-1 element enables T7 based transcription from the conserved LINE-1 diagnostic sequence out toward the flanking sequence. A comparison of tumor and normal sequencing of the products reveals somatic LINE-1 rearrangements with unparalleled accuracy. Multiple T7 insertions along both 3' and 5' ends as well as throughout the conserved LINE-1 element sequence adds the ability to identify full length somatic L1 transposition in tumors. It is estimated that 60% of tumors have somatic L1 events.

In order to map the sites of LINE-1 rearrangements in tumors, a plasmid is constructed to contain a targeted sequence complementary to a sequence in the LINE-1 element and a T7 promoter. The targeted sequence is selected to work most effectively with Cas9 in the CRISPR system. A guide RNA is made from the plasmid, the guide RNA containing the targeted sequence and the T7 promoter. The guide RNA is incubated with the genomic DNA sample from the tumor and isolated Cas9 enzyme. The resulting product, a tagged genomic DNA sample that has a T7 promoter inserted into the targeted LINE-1 sequence, is purified. The tagged genomic DNA sample is incubated with nucleotides and a T7 RNA polymerase which creates an RNA transcript from the LINE-1 element. Each transcript is made directly from the tagged genomic DNA sample and no errors such as insertions deletions, or point mutations are made. The RNA sample is then purified from the tagged genomic DNA sample and polyadenylated. A cDNA is made from the RNA sample in a reverse transcriptase reaction and oligo-dT. The RNA is removed from the cDNA using RNaseH and the cDNA is used in sequencing reactions to determine the sequence of the genomic DNA adjacent to the LINE-1 element and thereby the location of the LINE-1 element. The location of the element and any additional LINE-1 elements in the tumor sample gives diagnostic information to the physician such as specific treatments that may work to cure the tumor.

Example 3

Determining Length of Tri-Nucleotide Repeat Length in Huntington's Disease

Huntington's disease is a neurodegenerative genetic disorder that affects muscle coordination, cognitive ability, and behavior. A well-documented mutation in the Huntingtin gene is responsible for the disease, which is inherited in an autosomal dominant fashion. The mutation is an expansion, from one generation in a family to the next, of a CAG trinucleotide repeat stretch found in the coding sequence of the gene. This CAG trinucleotide encodes the amino acid glutamine, so expansion of the CAG repeat results in expansion of a polyglutamine stretch in the resulting protein. Obtaining an exact sequence of the expanded polynucleotide region presents challenges. As the size of the repeat region affects the disease status of the patient it is desirable to determine the sequence and therefore the size of the repeat region.

In order to determine the size of the CAG repeat, a plasmid is constructed to contain a targeted sequence complementary to a sequence in the Huntingtin gene and a T7 promoter. The targeted sequence is selected to work most effectively with Cas9 in the CRISPR system. A guide RNA is made from the plasmid, the guide RNA containing the targeted sequence and the T7 promoter. The guide RNA is incubated with the genomic DNA sample from the tumor and isolated Cas9 enzyme. The resulting product, a tagged genomic DNA sample that has a T7 promoter inserted into the targeted Huntingtin sequence, is purified. The tagged genomic DNA sample is incubated with nucleotides and a T7 RNA polymerase which creates an RNA transcript from the Huntingtin gene. Each transcript is made directly from the tagged genomic DNA sample and no errors such as insertions deletions, or point mutations are made. The RNA sample is then purified from the tagged genomic DNA sample and polyadenylated. A cDNA is made from the RNA sample in a reverse transcriptase reaction and oligo-dT. The RNA is removed from the cDNA using RNaseH and the cDNA is used in sequencing reactions to determine the sequence of the CAG repeat in the Huntingtin gene. The number of CAG repeats in the Huntingtin gene gives diagnostic information to the physician and the patient regarding the expected severity of disease.

Example 4

Using CRISPR/CAS to Insert Hairpin Tags into the Genome

A Cyp2d6 gene is selected for sequencing using CRISPR/CAS to create a double stranded break at a target site in the genome at the genomic locus of the gene. The double stranded break is made into a sticky end by treating the DNA sample with an exonuclease exposing one strand of the target site. The tagged nucleic acid has a portion with a nucleic acid sequence complementary to the exposed strand, a T7 promoter, and a portion that is self-complementary and forms a hairpin. DNA ligase ligates the tagged nucleic acid to the target site thereby incorporating a T7 promoter near the Cyp2d6 gene. The hairpin tag is efficient at ligating the tag to the target site and the site is ready for targeted RNA transcription of the Cyp2d6 gene. The tag allows the Cyp2d6 gene to be uniquely tagged for sequencing, differentiating from the Cyp2d6 pseudogene.

Example 5

Size Selection of In Vitro Transcribed RNA

In vitro transcription was performed on 1 ng DNA samples comprising T7 promoter inserted DNA. Reactions were run for 12 hours. Both MEGAscript T7 and AmpliScribe T7 were used to drive transcription. Reactions were incubated with DNAse for 1 hour subsequent to transcription. RNA was quantified using a Qubit High Sensitivity RNA Assay kit. RNA analysis was performed using a High Sensitivity Pico mRNA Bioanalyzer.

Size exclusion included sub-17 nt size exclusion; sub-200 nt size exclusion' incubation for 10 minutes at 65° C. followed by sub-17 nt size exclusion; and unexcluded control. Products were run on formaldehyde (denaturing) agarose gel.

Results are depicted in TABLE 1, below.

TABLE 1

| Sample | RNA (ng) | % yield |
|---|---|---|
| MEGAscript > 17 nt | 716 | 85 |
| Ampliscribe > 17 nt | 714 | 78 |
| MEGAscript > 200 nt | 637 | 76 |
| Ampliscribe > 200 nt | 658 | 72 |
| MEGAscript 65 C., > 17 nt | 690 | 82 |
| Ampliscribe 65 C., > 17 nt | 573 | 62 |
| MEGAscript control | 838 | 100 |
| Ampliscribe control | 918 | 100 |

Results are graphically presented in FIG. 10.

Bead-based size selection was also accomplished. In vitro transcription was performed on 1 ng DNA samples comprising T7 promoter inserted DNA. Reactions were run for 12 hours. Both MEGAscript T7 and AmpliScribe T7 were used to drive transcription. Reactions were incubated with DNAse for 1 hour subsequent to transcription. Reactions were incubated as follows: 50uL starting volume, 2ng RNA output, with 0.5×, 0.6×, 0.8×, 1×, 2×, 3×, and control (unselected). RNA was quantified using a Qubit High Sensitivity RNA Assay kit. RNA analysis was performed using a High Sensitivity Pico mRNA Bioanalyzer.

Example 6

Insertion of a Hairpin Adapter to a Target DNA Site

A Cyp2d6 gene is selected for sequencing using CRISPR/CAS to create a double stranded break at a target site in the genome at the genomic locus of the gene. The double stranded break is made into a sticky end by treating the DNA sample with an exonuclease exposing one strand of the target site. The tagged hairpin adapter nucleic acid has a portion with a nucleic acid sequence complementary to the exposed strand, a double stranded T7 promoter having a portion that is self-complementary that forms a hairpin. DNA ligase ligates the tagged nucleic acid to the target site thereby incorporating a T7 promoter near the Cyp2d6 gene. The hairpin tag is efficient at ligating the tag to the target site and the site is ready for targeted RNA transcription of the Cyp2d6 gene. The double stranded T7 promoter is efficient in RNA transcription of the Cyp2d6 gene. The tag allows the Cyp2d6 gene to be uniquely tagged for sequencing, differentiating from the Cyp2d6 pseudogene.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of determining a first nucleic acid sequence comprising: (a) inserting a targeting nucleic acid sequence comprising a targeting sequence and a promoter in a second nucleic acid sequence that is upstream of or downstream of the first nucleic acid sequence, (b) directing synthesis of a linear amplified nucleic acid from the promoter using genomic nucleic acid as template, wherein the linear amplified nucleic acid comprises an amplified nucleic acid sequence of the first nucleic acid sequence that is amplified upon insertion of the targeting nucleic acid sequence and (c) sequencing the synthesized linear amplified nucleic acid;
wherein the second nucleic acid sequence is a genomic sequence that comprises a mobile genetic element, a repetitive nucleic acid sequence, a polymorphism, or a mutation; and
wherein the first nucleic acid sequence is a genomic sequence that is amplified upon insertion of the targeting nucleic acid sequence in the second nucleic acid sequence.

2. The method of claim 1, wherein the targeting sequence comprises at least one sequence selected from the list of a clustered regularly interspaced short palindromic repeats (CRISPR) recognition sequence, a zinc finger nuclease (ZFN) recognition sequence, and a transcription activator-like effector nucleases (TALENs) recognition sequence.

3. The composition of claim 2, wherein the CRISPR recognition sequence comprises SEQ ID NO: 3.

4. The method of claim 1, wherein the promoter comprises at least one promoter selected from the list of a bacterial promoter, a viral promoter, and a eukaryotic promoter.

5. The method of claim 1, wherein the first nucleic acid sequence comprises a nucleic acid mutation.

6. The method of claim 5, wherein the mutation is at least one of a point mutation, a deletion, an insertion, and a chimera.

7. The method of claim 1, wherein the second nucleic acid sequence comprises a repetitive nucleic acid sequence.

8. The method of claim 7, wherein the second nucleic acid sequence comprises at least one of tri-nucleotide repeat, tandem repeat, and human leukocyte antigen gene.

9. The method of claim 1, wherein the second nucleic acid sequence comprises a mobile genetic element.

10. The method of claim 9, wherein the mobile genetic element comprises a transposon, a retrotransposon, a DNA transposon, an insertion sequence, a plasmid, a bacteriophage, a group II intron, a group I intron, a long interspersed nuclear element (LINE), an Alu element, a MIR element, an intracisternal A particle (IAP), an ETn, a virus, or a fragment thereof.

11. The method of claim 1, wherein nucleic acid synthesis comprises at least one of RNA transcription and DNA synthesis.

12. The method of claim 11, wherein RNA transcription comprises use of at least one RNA polymerase selected from the group consisting of a T7 RNA polymerase, a T3 RNA polymerase, a SP6 RNA polymerase, a RNA polymerase I, a RNA polymerase II, a RNA polymerase III, a RNA polymerase IV, a RNA polymerase V, and a single subunit RNA polymerase.

13. The method of claim 11, wherein the DNA synthesis comprises use of at least one DNA polymerase selected from the group consisting of a T7 DNA polymerase, a T3 DNA polymerase, a SP6 DNA polymerase, a DNA polymerase I, a DNA polymerase II, a DNA polymerase III, a Taq DNA polymerase, and a Pfu DNA polymerase.

14. The method of claim 1, wherein the nucleic acid synthesis requires a primer.

15. The method claim 1, wherein the synthesis of the linear amplified nucleic acid is initiated directly from the second nucleic acid and continued through the first nucleic acid, and wherein the linear amplified nucleic acid comprises at least a complete sequence of the first nucleic acid, and, optionally, a partial nucleic acid sequence of the second nucleic acid that is downstream of the promoter.

16. The method of claim 1, wherein the linear amplified nucleic acid is not amplifying a polymerase induced mutation.

17. The method of claim 1, wherein the sequencing comprises at least one of Sanger sequencing, Next-generation sequencing, pyrosequencing, Massively parallel signature sequencing, single molecule real-time sequencing, ion torrent sequencing, sequencing by synthesis, and sequencing by ligation.

18. The method of claim 1, wherein the method detects a mutation in a subject.

19. The method of claim 1, wherein the method detects a mutation in a tissue sample obtained from a subject.

20. The method of claim 19, wherein the tissue sample comprises at least one of tumor, blood, saliva, sputum, skin, or epithelial tissue.

21. The method of claim 1, wherein the second nucleic acid sequence comprises at least a tri-nucleotide repeat element, or a tandem repeat element, and wherein the second nucleic acid sequence comprises a non-variant non-repeat sequence within which the targeting nucleic acid sequence comprising a targeting sequence and a promoter is inserted; and wherein the synthesis of the linear amplified nucleic acid from the promoter amplifies the sequence comprising the at least a tri-nucleotide repeat, or the tandem repeat element.

22. The method of claim 1, wherein the first nucleic acid sequence is within 20 kb from the border of the second nucleic acid sequence.

23. The method of claim 1, wherein synthesized linear amplified nucleic acid sequence is at least 1000 bases long.

* * * * *